(12) United States Patent
Taylor

(10) Patent No.: US 8,286,847 B2
(45) Date of Patent: Oct. 16, 2012

(54) APPARATUS FOR LAPAROSCOPIC OR ENDOSCOPIC PROCEDURES

(75) Inventor: Eric J. Taylor, Middletown, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 1287 days.

(21) Appl. No.: 11/580,602

(22) Filed: Oct. 13, 2006

(65) Prior Publication Data

US 2007/0084899 A1 Apr. 19, 2007

Related U.S. Application Data

(60) Provisional application No. 60/726,589, filed on Oct. 14, 2005.

(51) Int. Cl.
*A61B 17/068* (2006.01)
(52) U.S. Cl. ............... 227/176.1; 227/175.1; 227/19
(58) Field of Classification Search .... 227/175.1–182.1, 227/19; 277/634, 36
See application file for complete search history.

(56) References Cited

U.S. PATENT DOCUMENTS

| | | | | |
|---|---|---|---|---|
| 2,041,781 A * | 5/1936 | Sager | ............................... | 384/16 |
| 2,368,744 A * | 2/1945 | Carey | ............................ | 277/453 |
| 2,444,703 A * | 7/1948 | Jones | ............................ | 137/340 |
| 2,447,663 A * | 8/1948 | Payne | ............................ | 277/388 |
| 2,815,967 A * | 12/1957 | Payne et al. | .................... | 277/315 |
| 2,884,267 A * | 4/1959 | Kosatka | ......................... | 277/372 |
| 3,059,936 A * | 10/1962 | Barrett | .......................... | 277/391 |
| 3,336,034 A * | 8/1967 | Smith | ............................ | 277/359 |
| 3,485,142 A * | 12/1969 | James et al. | .................. | 92/169.1 |
| 3,587,405 A * | 6/1971 | Holmes | ............................ | 92/5 R |
| 3,884,238 A * | 5/1975 | O'Malley et al. | ............. | 606/107 |
| 4,036,505 A * | 7/1977 | Floyd et al. | ..................... | 277/405 |
| 4,449,717 A * | 5/1984 | Kitawaki et al. | ............... | 277/568 |
| 4,526,388 A * | 7/1985 | Marshall | ........................ | 277/565 |
| 4,560,176 A * | 12/1985 | Hoff | ................................. | 277/505 |
| 4,672,965 A * | 6/1987 | Baum | ............................ | 606/169 |
| 4,724,840 A | 2/1988 | McVay et al. | | |
| 4,972,867 A * | 11/1990 | Ruesch | ....................... | 137/15.11 |
| 4,986,827 A * | 1/1991 | Akkas et al. | .................. | 606/107 |
| 5,058,861 A * | 10/1991 | Baumann | .................... | 251/335.3 |
| 5,176,677 A | 1/1993 | Wuchinich | | |
| 5,234,039 A * | 8/1993 | Aoshima et al. | ............... | 141/312 |
| 5,318,221 A | 6/1994 | Green et al. | | |
| 5,346,230 A * | 9/1994 | Schumacher et al. | ......... | 277/551 |
| 5,474,303 A * | 12/1995 | Coles | ............................. | 277/317 |
| 5,897,119 A * | 4/1999 | McMillen | ...................... | 277/562 |
| 2004/0026873 A1 * | 2/2004 | Davey | ............................ | 277/608 |
| 2006/0103075 A1 * | 5/2006 | Zahn | .............................. | 277/436 |

FOREIGN PATENT DOCUMENTS

DE 42 20 644 1/1994

OTHER PUBLICATIONS

European Search Report (EP 06 02 1544).

\* cited by examiner

*Primary Examiner* — Lindsay Low

(57) ABSTRACT

A surgical apparatus for performing endoscopic or laparoscopic surgical procedures is disclosed. The apparatus includes a frame and a bellows seal which provides a seal between the frame and a clamping mechanism and the frame and a firing mechanism. The bellows seal is positioned within the frame such that the bellows seal expands outwardly upon advancement of a clamp member of the clamping mechanism to provide a seal within the frame or to increase the capacity of the seal within the frame.

22 Claims, 44 Drawing Sheets

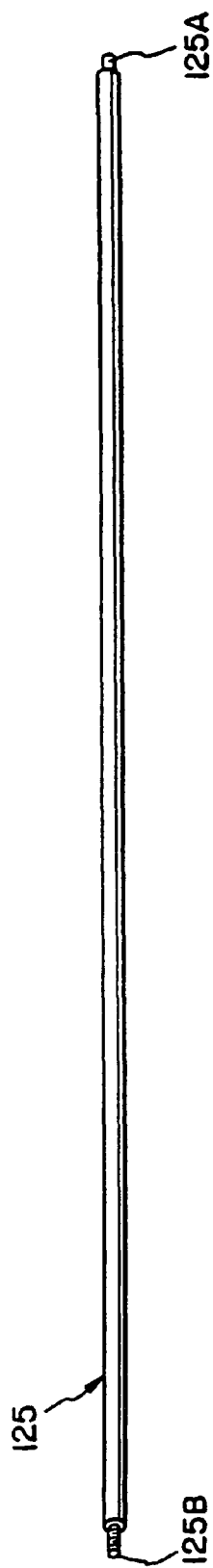
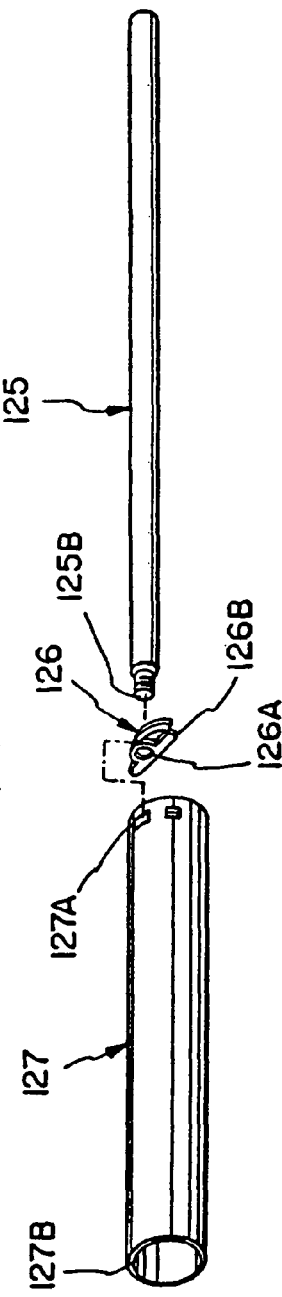

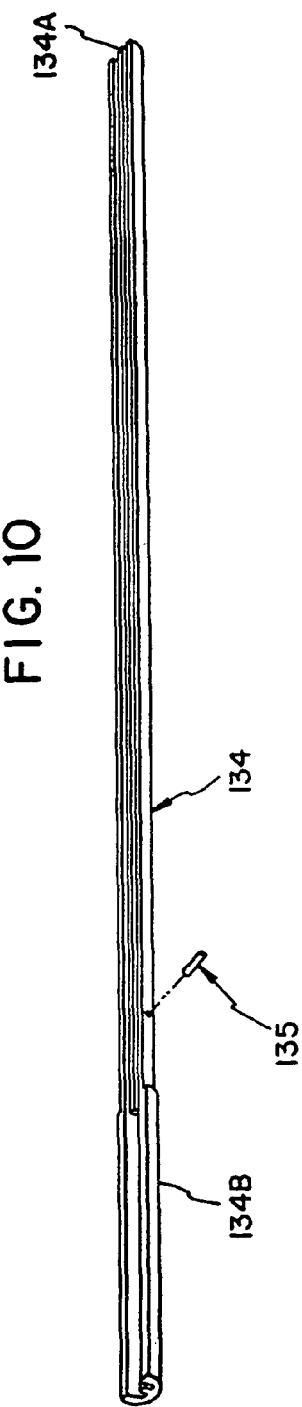
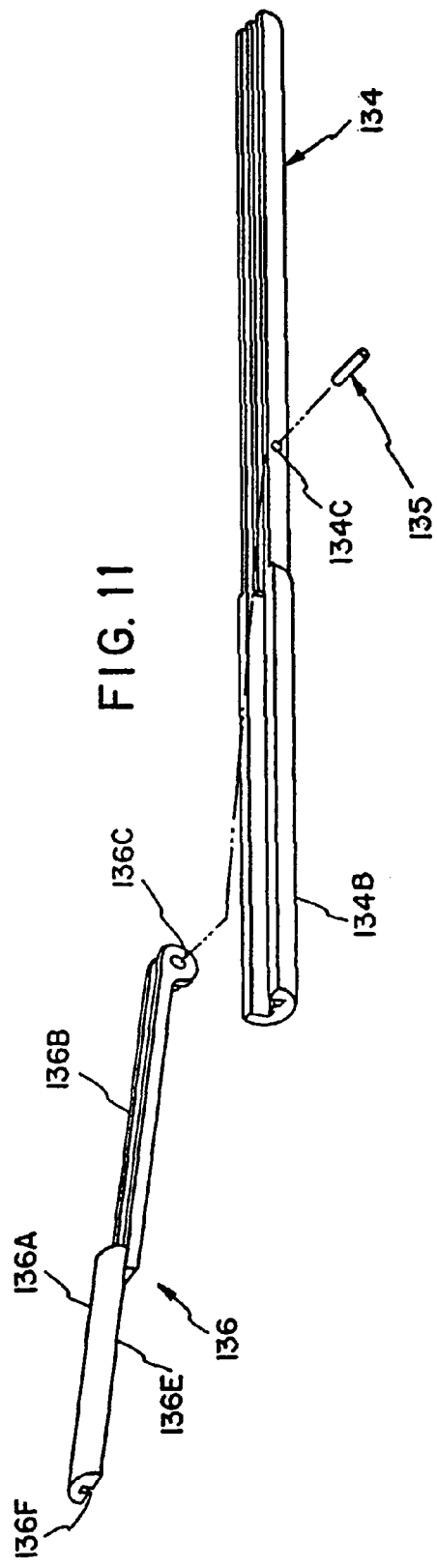

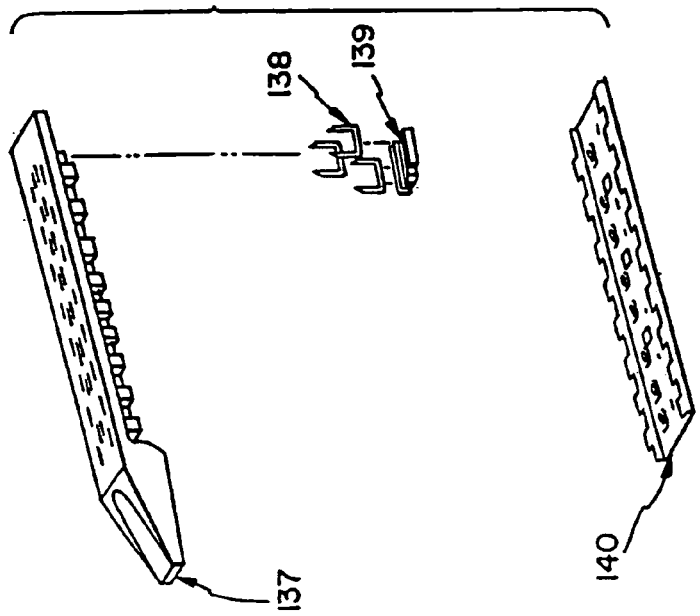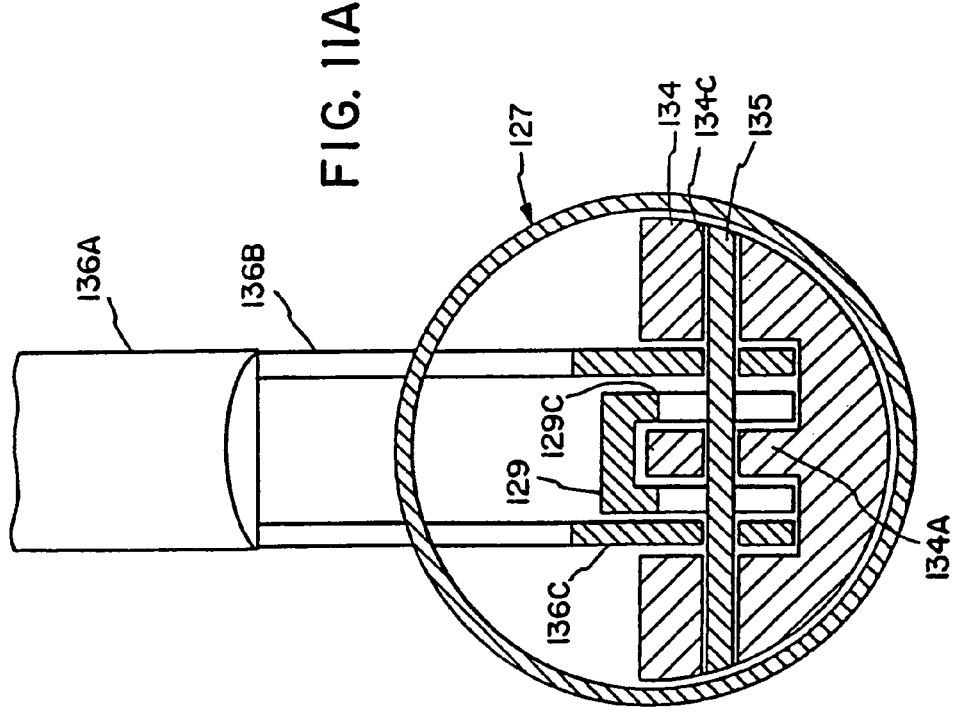

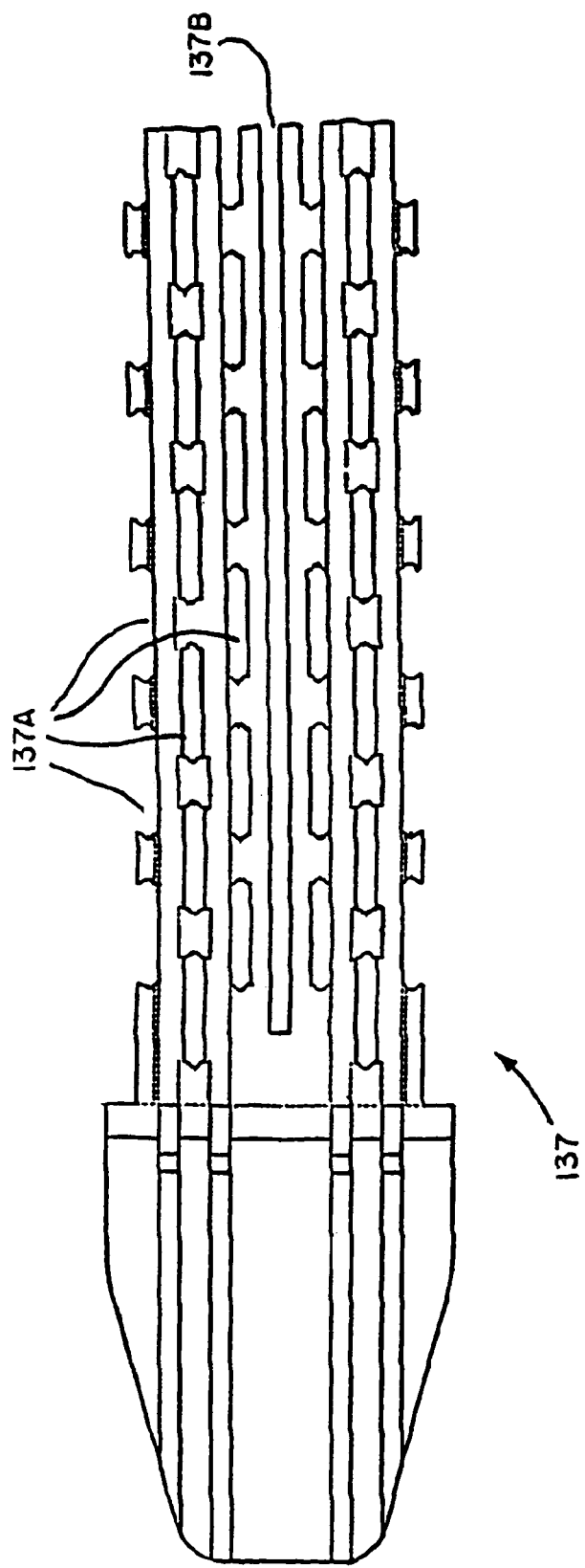

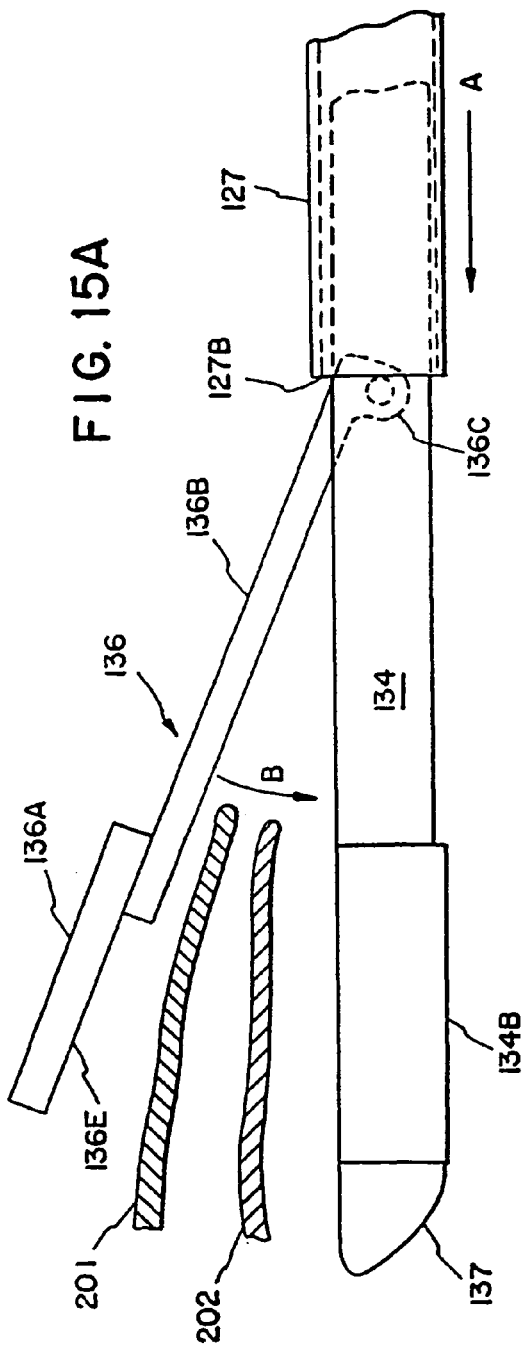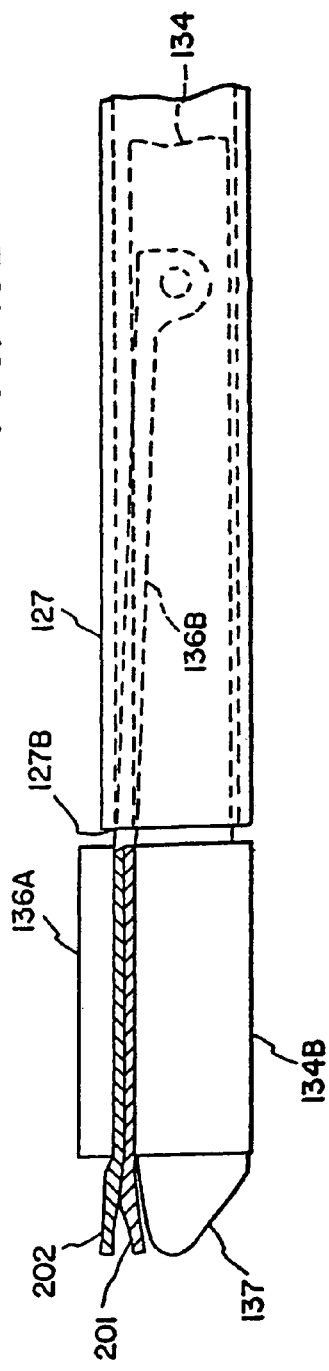

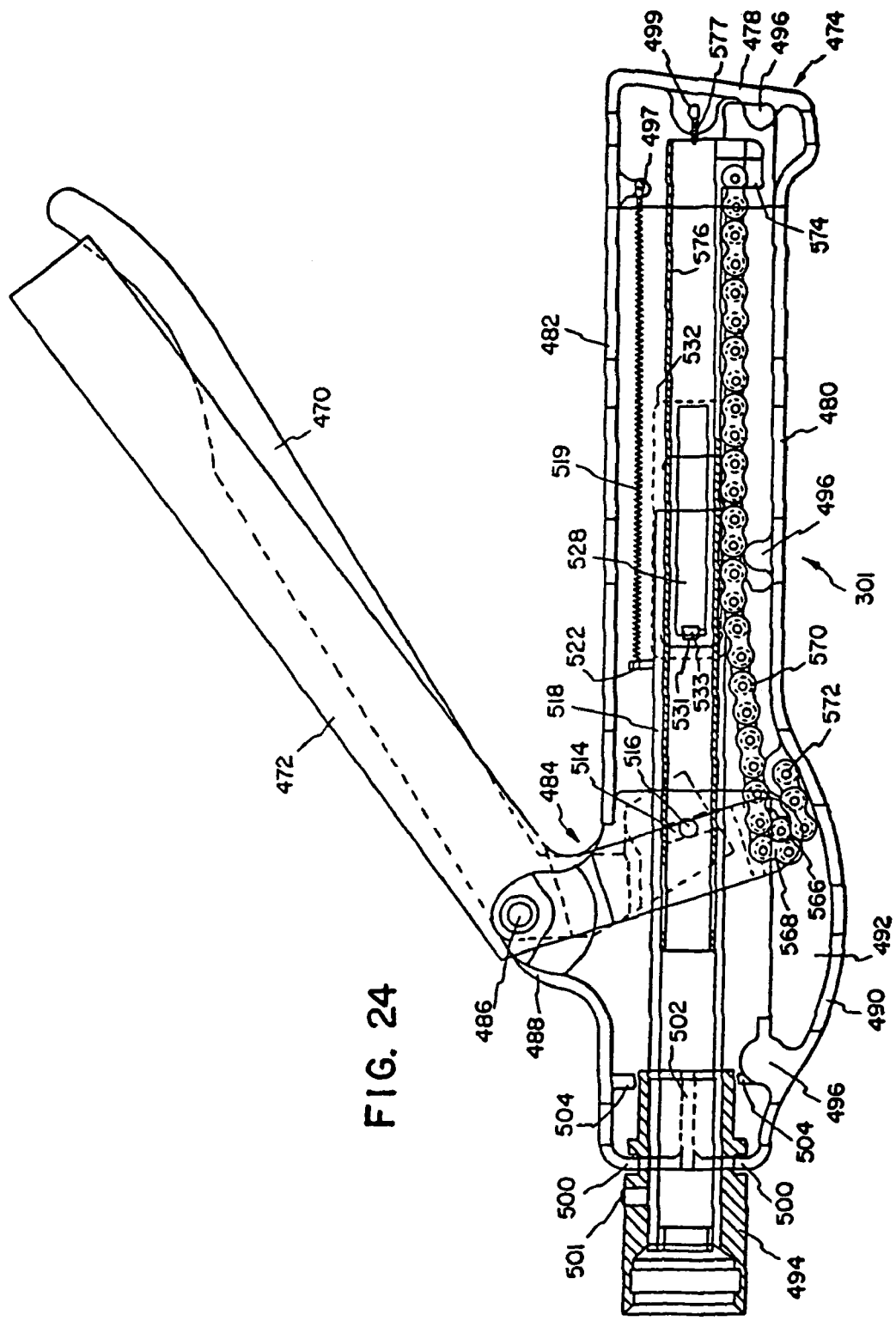

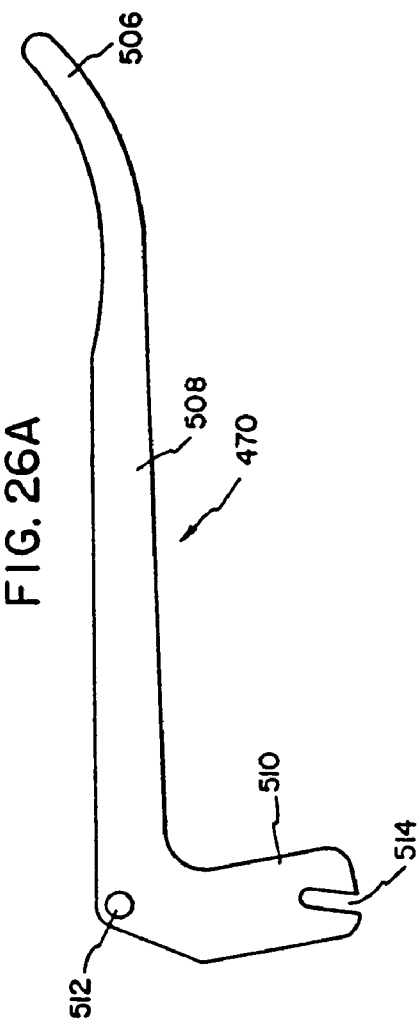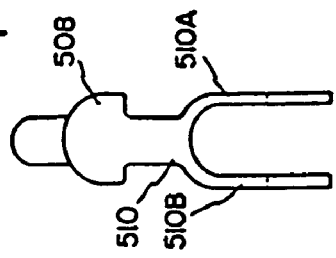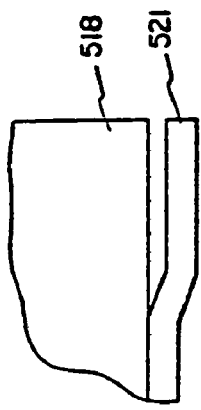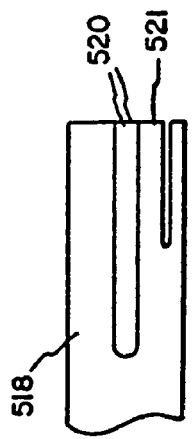

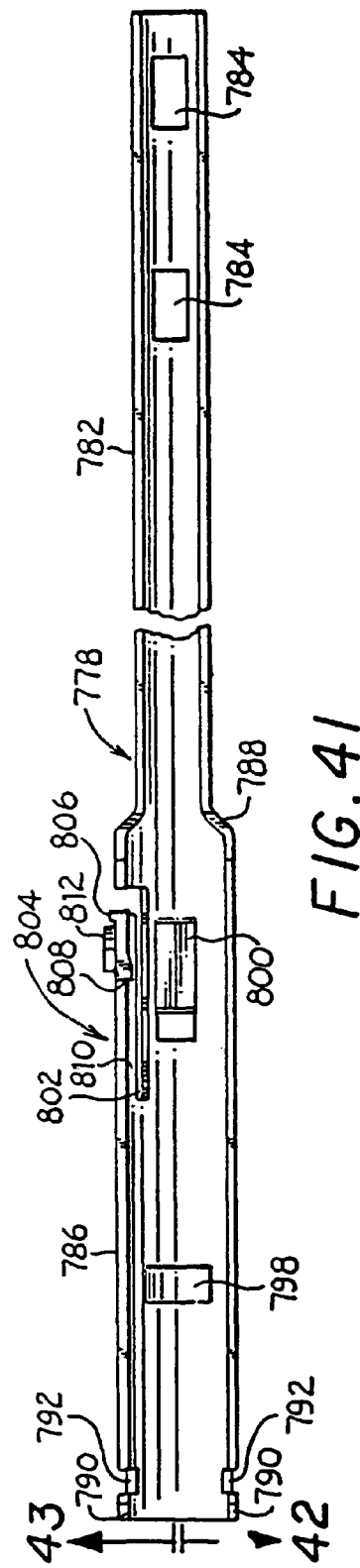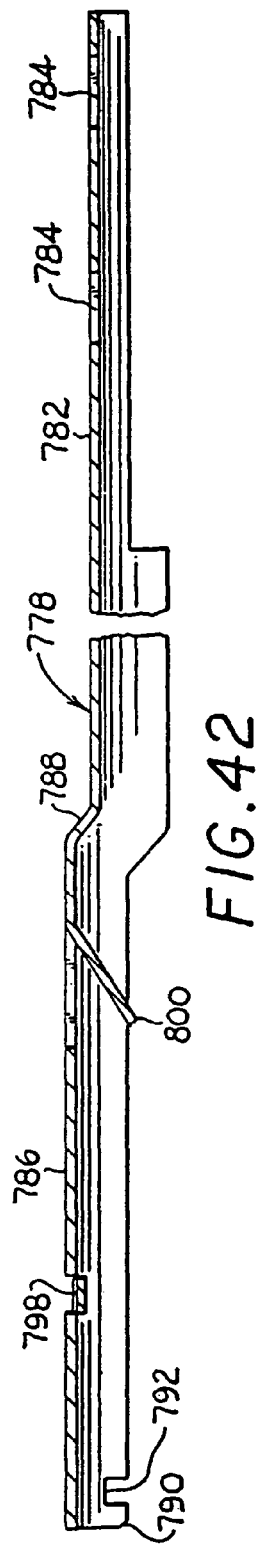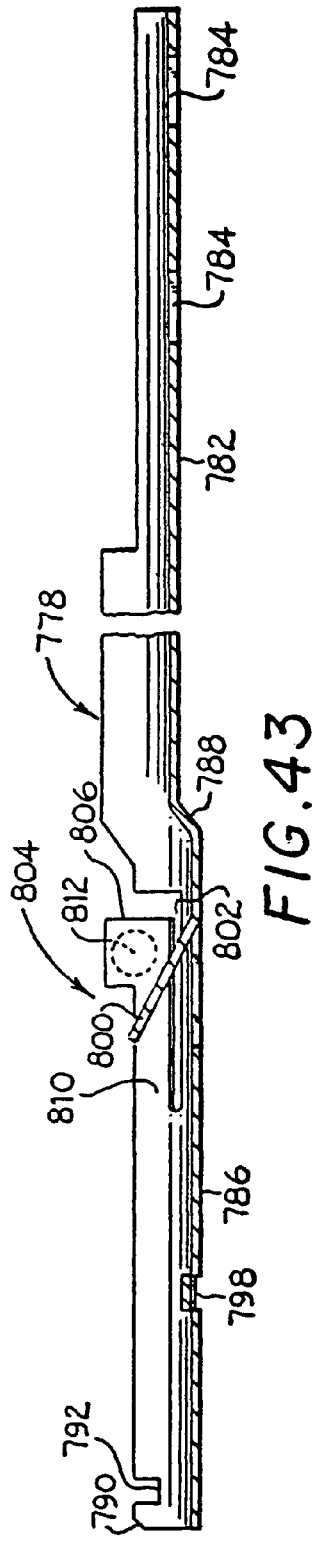

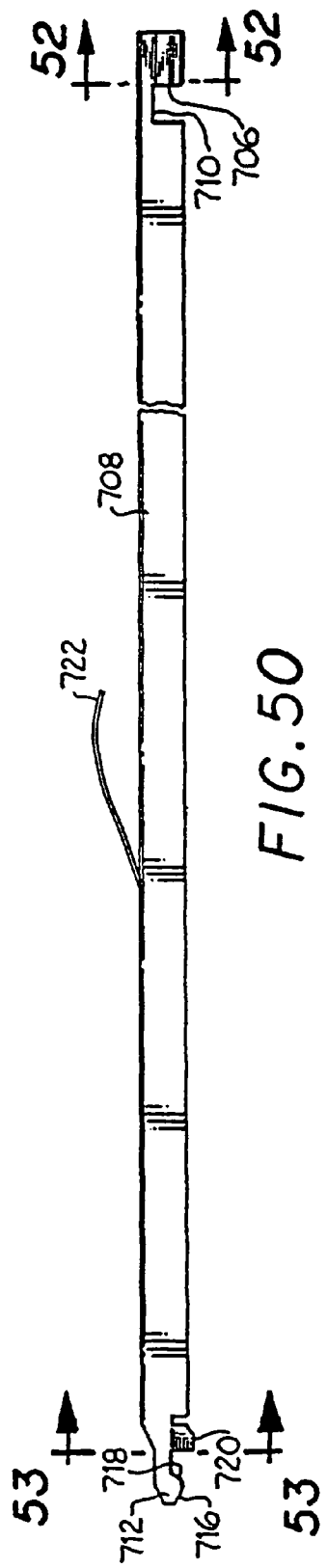
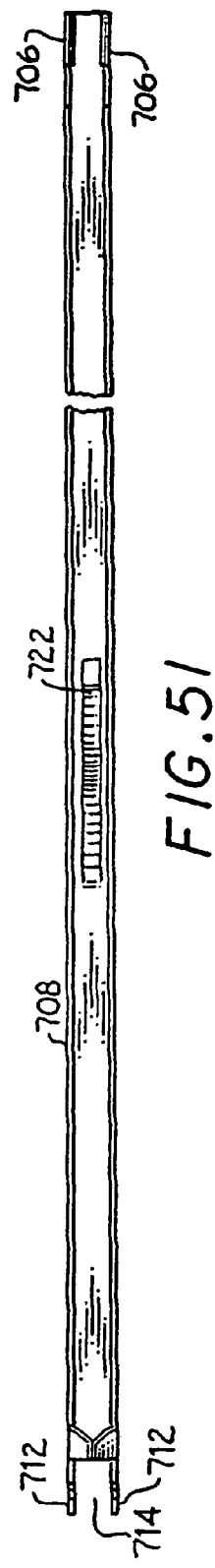
FIG.50
FIG.51
FIG.53
FIG.52

APPARATUS FOR LAPAROSCOPIC OR ENDOSCOPIC PROCEDURES

This application claims priority to U.S. provisional application Ser. No. 60/726,589, filed Oct. 14, 2005 which is incorporated herein in its entirety by reference.

U.S. Pat. No. 5,318,221 is incorporated herein in its entirety by reference.

BACKGROUND OF THE INVENTION

1. Technical Field

The present disclosure relates to an endoscopic or laparoscopic surgical apparatus, and more particularly to an endoscopic or laparoscopic stapling apparatus.

2. Background of Related Art

Endoscopic and laparoscopic surgical procedures have become quite common and are preferred over open surgical procedures because of their less intrusive nature and the benefits associated therewith, i.e., reduced patient trauma, faster recovery time, etc. Typically, when an endoscopic surgical procedure is performed on the abdomen, the abdomen is insufflated to improve accessibility to the surgical site. As such, endoscopic surgical apparatus have been provided with sealing structure to prevent insufflation gases from exiting the abdomen through the apparatus. Although, this sealing structure has proven effective, further improvements would be desirable.

SUMMARY

A surgical apparatus is provided for driving surgical fasteners into body tissue. The apparatus includes a frame, an endoscopic portion defining a longitudinal axis and extending distally from the frame, and a tool assembly supported on the distal end of the endoscopic portion. The tool assembly has a first jaw pivotably supported in relation to a second jaw. The first jaw is movable in relation to the second jaw between open and closed positions. A first mechanism extends between the tool assembly and the frame and includes a clamp tube positioned at least partially within the frame. The clamp tube is movable from a retracted position to an advanced position to move the first jaw in relation to the second jaw from the open position to the closed position. A second mechanism extends between the frame and the tool assembly and includes an extension tube which is movable from a retracted position to an advanced position to actuate the tool assembly. A bellows seal has a distal end and a proximal end and a central bellows portion. The bellows seal defines a throughbore. The distal end of the bellows seal is positioned to sealingly engage an outer surface of the extension tube and the proximal end of the bellows seal is positioned to sealingly engage the clamp tube. As the clamp tube is moved from the retracted position to the advanced position, the bellows seal is compressed and expanded outwardly to seal against an internal surface of the frame.

In one embodiment, the frame includes an internal flange which is positioned to engage the bellows seal as the clamp tube is moved from its retracted position to its advanced position. In one embodiment, the bellows seal does not engage the internal surface of the frame until the clamp tube is moved towards its advanced position. Alternately, the bellows seal can be in a light interference condition with the internal surface of the frame to provide a seal with the frame when the clamp tube is in its retracted position, and wherein movement of the clamp tube towards its advanced position increases the capacity of the seal.

In one embodiment, the first jaw includes an anvil member and the second jaw includes a cartridge assembly. The cartridge assembly includes a plurality of staples.

In one embodiment, the frame supports a clamp handle which is operably associated with the first mechanism and a handle assembly which is operably associated with the second mechanism.

In one embodiment, the frame supports a clamp handle which is operably associated with the first mechanism and a handle assembly which is operably associated with the second mechanism.

In one embodiment, the clamp tube is configured to engage an external surface of the anvil member to move the anvil member and the cartridge assembly from the open position to the closed position.

In one embodiment, the endoscopic portion is rotatably supported on the frame.

BRIEF DESCRIPTION OF THE DRAWINGS

Various embodiments of the presently disclosed apparatus for laparoscopic or endoscopic procedures are disclosed herein with reference to the drawings, wherein:

FIGS. 6 and 7 show the collar shaft and collar;

FIGS. 10 and 11 illustrate the housing and anvil;

FIG. 11A illustrates a sectional view of the housing and collar;

FIG. 12 illustrates an exploded view of the cartridge, staple drive member and staples;

FIG. 14 illustrates the surface of the cartridge which comes in contact with body tissue;

FIGS. 15A and 15B illustrate the clamping action of the instrument;

FIG. 24 illustrates a sectional side view of a handle and frame portion in accordance with the first alternative embodiment;

FIGS. 26A and 26B illustrate side and distal end views, respectively, of the inner handle of the first alternative embodiment;

FIGS. 27A, 27B, 27C, 27D and 27E illustrate bottom plan, front side, sectional front side and two partial rear side views, respectively, of the frame clamp tube;

FIGS. 34 and 34A illustrate an exploded perspective view of the frame and actuating assembly of the stapler apparatus in accordance with the second alternative embodiment of the invention;

FIGS. 34 and 35A illustrates an exploded perspective view of the frame and actuating assembly of the stapler apparatus in accordance with the second alternative embodiment of the invention;

FIGS. 35 and 35A illustrate an exploded perspective view of elements of the tube assembly of the stapler apparatus in accordance with the second alternative embodiment of the invention;

FIGS. 41-43 illustrate top and side views of the support structure;

FIGS. 50-53 illustrate side, bottom and cross-sectional views of the channel of the stapler apparatus in accordance with the second alternative embodiment of the invention;

DETAILED DESCRIPTION OF THE EMBODIMENTS

Figure 1:
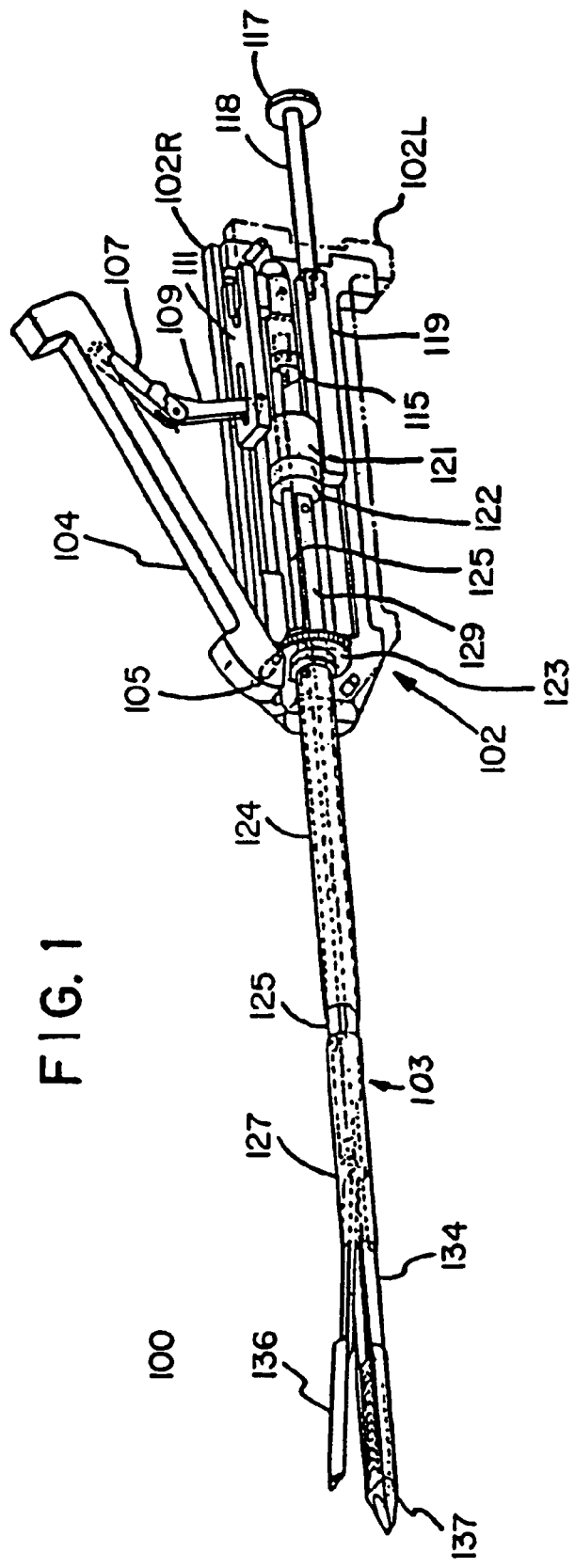
FIG. 1 illustrates a perspective cutaway view of the invention.

Embodiments of the presently disclosed apparatus for endoscopic or laparoscopic procedures will now be described in detail with reference to the drawings wherein like reference numerals designate identical or corresponding elements in each of the several views.

The surgical apparatus described herein includes a frame and handle portion supporting an endoscopic portion, i.e., an extended tube-like portion having a relatively narrow diameter, on the order of about 10 millimeters, for insertion into a small opening in or tube inserted into the body, such as in the abdominal cavity. The endoscopic portion defines a longitudinal axis and has a length appropriate for reaching the operation site in the interior of the body. The apparatus may be used in conjunction with endoscopes (devices for visually examining the interior of the body, for example, by means of fiber optics). The endoscopic portion of the apparatus is inserted through the small opening or wound, manipulated to the operation site, and the instrument is actuated. The endoscopic portion has a fastening and cutting portion including an elongated housing which carries a fastening and cutting portion including an elongated housing which carries a fastening and cutting portion to the operation site. The fastening and cutting portion includes jaws defined by a staple carrying cartridge (typically located at the distal end of the housing), an anvil and further includes a knife. Actuating the operating portion must be accomplished via intermediate components disposed on or within a narrow longitudinally extending tubular structure. The bulk of the primary operating components are housed on or within a frame, which is located outside the human (or animal) body being operated upon.

The instrument of the present invention has three basic actions or functions.

First, the endoscopic portion is introduced into the body and positioned with the jaws aligned at the stapling site to receive the target tissue. This may involve rotation of the endoscopic portion relative to the body, either by rotating the stapling instrument, as a whole, by rotating the endoscopic portion relative to the frame as permitted in the preferred embodiments, or a combination of both actions.

Second, the instrument has a means for securing the target body tissue between the cartridge assembly and the anvil. This is accomplished by a clamping action. With the target tissue clamped between the anvil and the cartridge assembly, a camming means which surrounds the housing and anvil member is employed to close the jaws of the apparatus and clamp the tissue between the anvil and the tissue contacting surface of the cartridge.

The third action is that of applying the staples to the body tissue. A longitudinally extending channel is employed to deliver longitudinal motion to pusher cam bars and a tissue cutting knife. The cam bars contact pusher elements which drive the staples through the body tissue against the fastener forming or forming surface of the anvil. After the instrument has been fired, the clamping action of the jaws is released and the instrument may be withdrawn from the body. The following details will provide an in-depth understanding of the various elements, operations and functions of the present invention.

FIG. 1 shows a cutaway perspective view of the instrument of the present invention 100, which generally comprises a frame 102 supporting an endoscopic portion 103, means for actuating the instrument to clamp body tissue, and means for firing the instrument to drive staples into the body tissue and form an incision in the tissue between staple rows.

Figure 2:
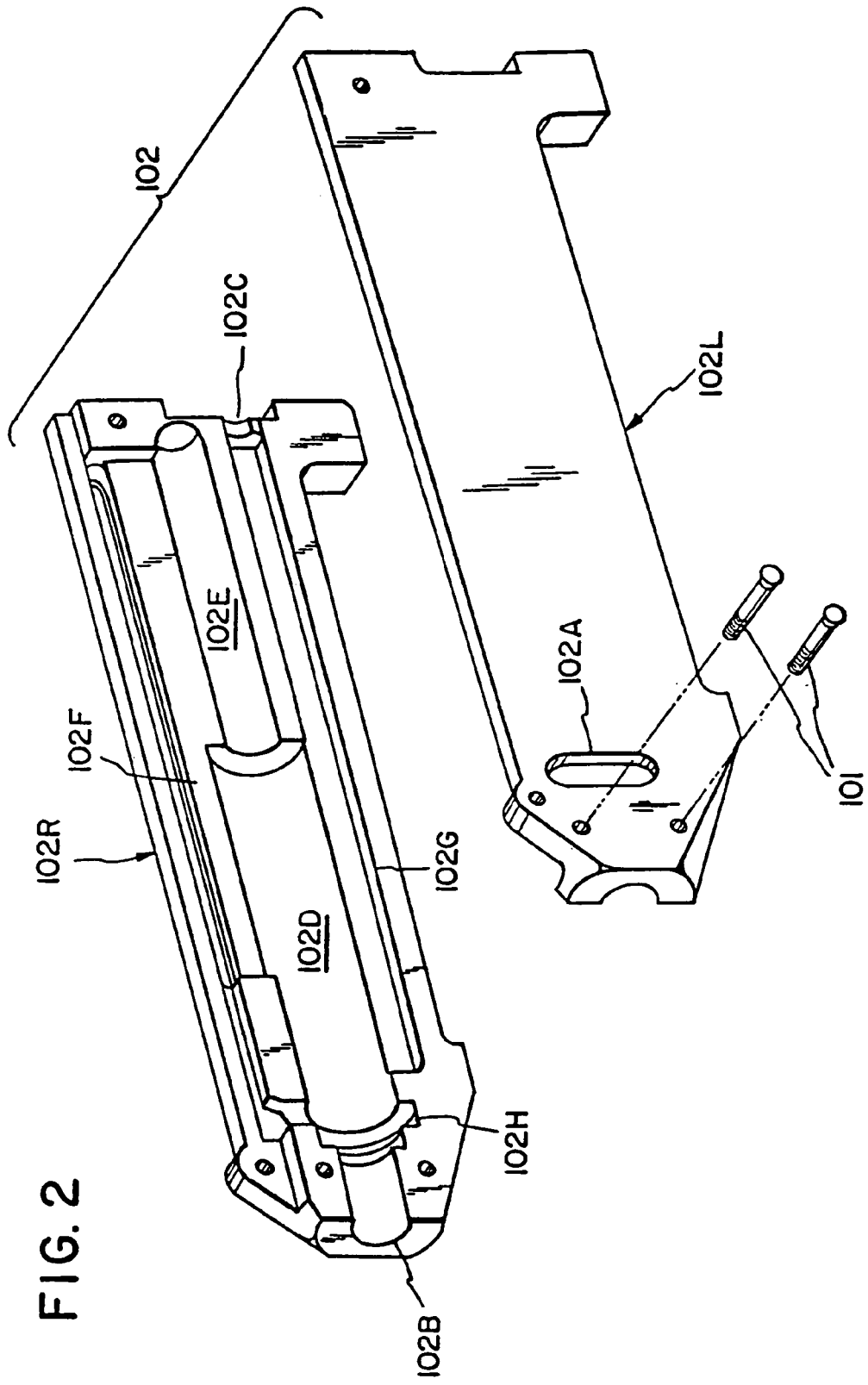
FIG. 2 illustrates an exploded view of the frame.

More particularly, referring now to FIGS. 1 and 2, frame 102 has two parts: a left portion 102L and a right portion 102R. These portions are optimally fastened together by means of fastening screws 101, although rivets, welds or other means of joining the two frame parts may also be used. The left portion 102L has a vertical elongated slot 102A to allow access to a thumbwheel 123 (See FIGS. 1 and 4). Frame 102 is elongated and has an interior surface defining a distal opening 102B, proximal opening 102C, and interior distal cylindrical chamber 102D, an interior proximal cylindrical chamber 102E, a circumferential thumbwheel mounting groove 102H, an upper guideway 102F, and a lower guideway 102G. The frame is of an overall size and shape convenient for being held in the hand.

Figure 3:
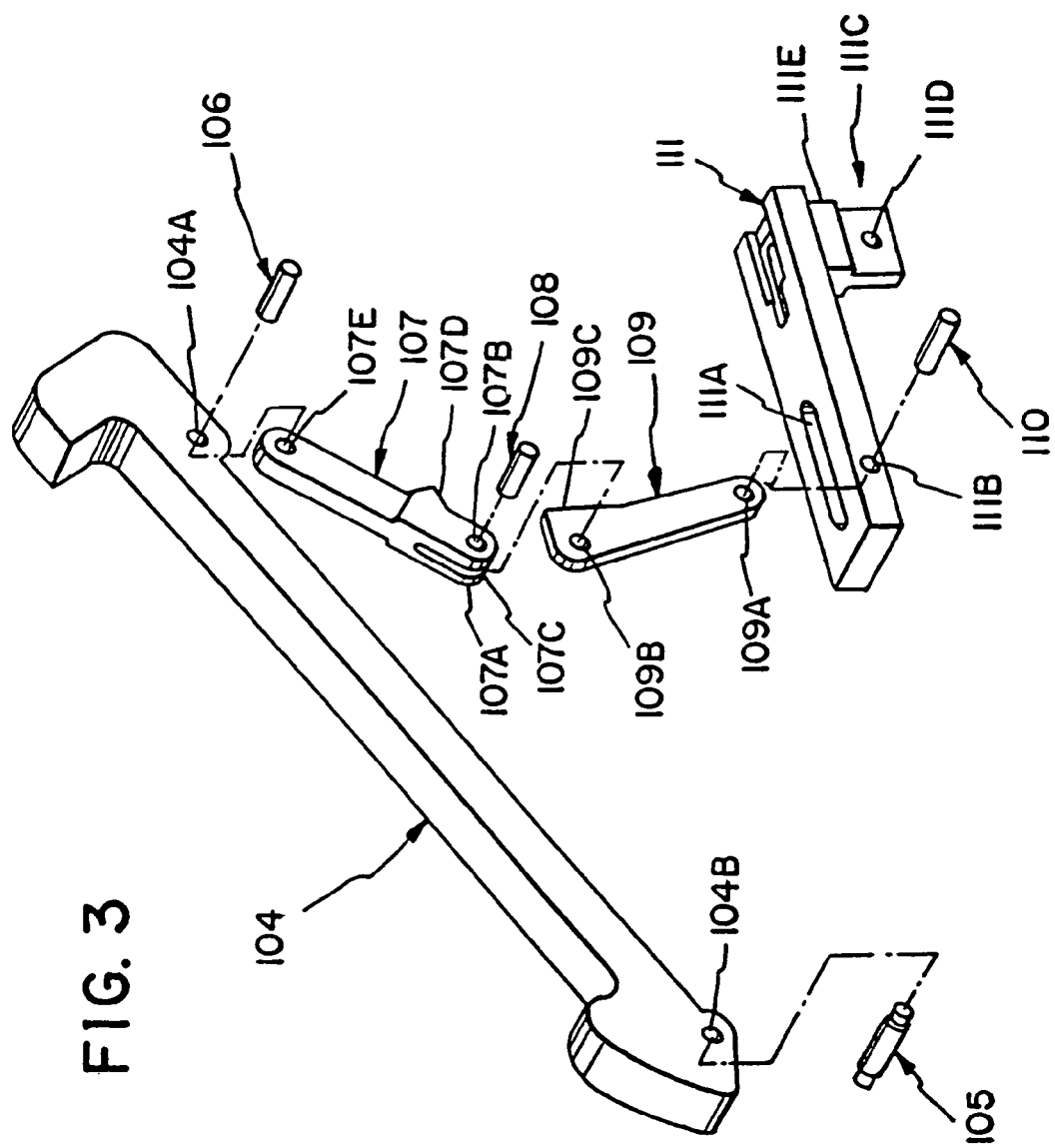
FIG. 3 illustrates an exploded view of the toggle lever actuating means.

Referring additionally now to FIG. 3, toggle lever 104 transfers motion to the toggle links discussed below and thereby provides a means to activate the clamping action of the apparatus in response to manual pressure from the surgeon or other operator of the instrument. Toggle lever 104 is an elongated piece having a distal end pivotally mounted in proximity to the distal end of the frame by means of lever pivot pin 105, which is disposed through transversely aligned aperture 104B in the distal end of the toggle lever 104. Toggle lever 104 further has a proximal end pivotally connected to toggle link 107 by means of toggle link pin 106 which is disposed through aperture 104A in the toggle lever. In response to pressure, the toggle lever 104 rotates around the axis defined by toggle lever pin 105, and transfers movement to the toggle links.

Toggle link 107 is an elongated member having a rounded first end with fork member 107A, which defines a longitudinal slot 107C, a transversely aligned aperture 107B for receiving toggle link pin 108, and a backstop surface 107D. The rounded second end of toggle link 107 has a transversely aligned aperture 107E for receiving toggle link pin 106. Toggle link 107 transfers movement from the toggle lever to toggle link 109.

Toggle link 109 is an elongated relatively thin, flat piece having a rounded first end with transversely aligned aperture 109A for receiving pin 110, and a partially rounded second end having transversely aligned aperture 109B for receiving toggle link pin 108, and a rotation limiting member 109C.

The first end of toggle link 109 is mounted in slot 111A of the collar moving pivot 111 by means of pin 110 which is disposed through aperture 109A. The second end of toggle link 109 is pivotally mounted in slot 107C in the fork member 107A of toggle link 107 by means of pin 108. Rotation limiter 109C is a flat angular member projecting proximally from the second end of the toggle link 109. The rotation limiter is adapted to abut the corresponding backstop surface 107D in toggle link 107 such that the joint between toggle links 107 and 109 is prevented from further bending in the distal direction. The rotation limiter 109C thus acts as a locking feature, preventing the toggle lever 104 from being depressed, and thereby preventing the clamping function to be actuated. When the coupling is bent in the proximal direction, however, the toggle lever 104 can be fully depressed so as to actuate the apparatus by moving collar moving pivot 111.

Collar moving pivot 111 is a substantially rectangular shaped piece slidably mounted in the upper guideway 102F of the frame 102. Collar moving pivot has a longitudinal slot 111A and a transversely aligned aperture 111B in proximity to the distal end of the collar proving pivot. The slot 111A is for receiving the first end of toggle link 109, and the aperture 111B is for receiving pin 110 for pivotally mounting said toggle link 109. Collar moving pivot 111 has a depending plate 111C, which has a relatively wide spacer portion 111E and transversely aligned aperture 111D for receiving pin 113 (FIG. 4).

Figure 4:
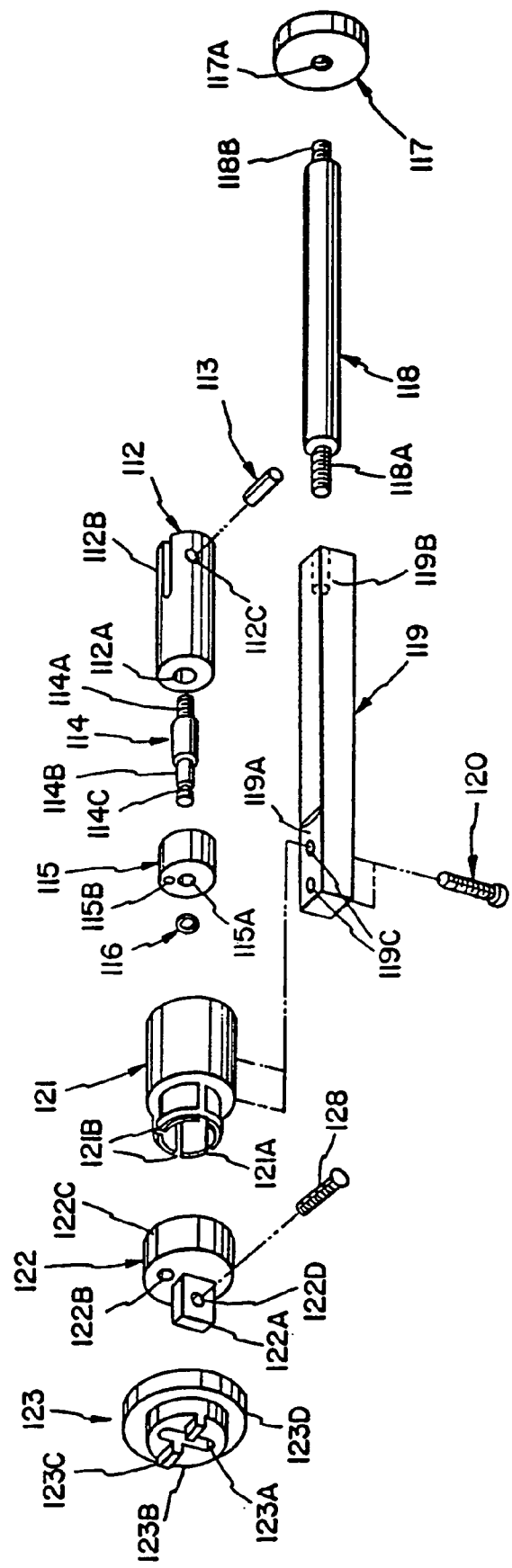
FIG. 4 illustrates an exploded view of the interior actuating means.

Depending portion 111C is mounted in slot 112B of the collar pivot holder 112 (FIG. 4). Pin 113 disposed through aperture 112C in the collar pivot holder and 111D in the collar moving pivot, links these two pieces. Collar moving pivot 111 provides a means to convert the rotational motion of the toggle links to linear movement in the longitudinal direction.

Figure 4A:
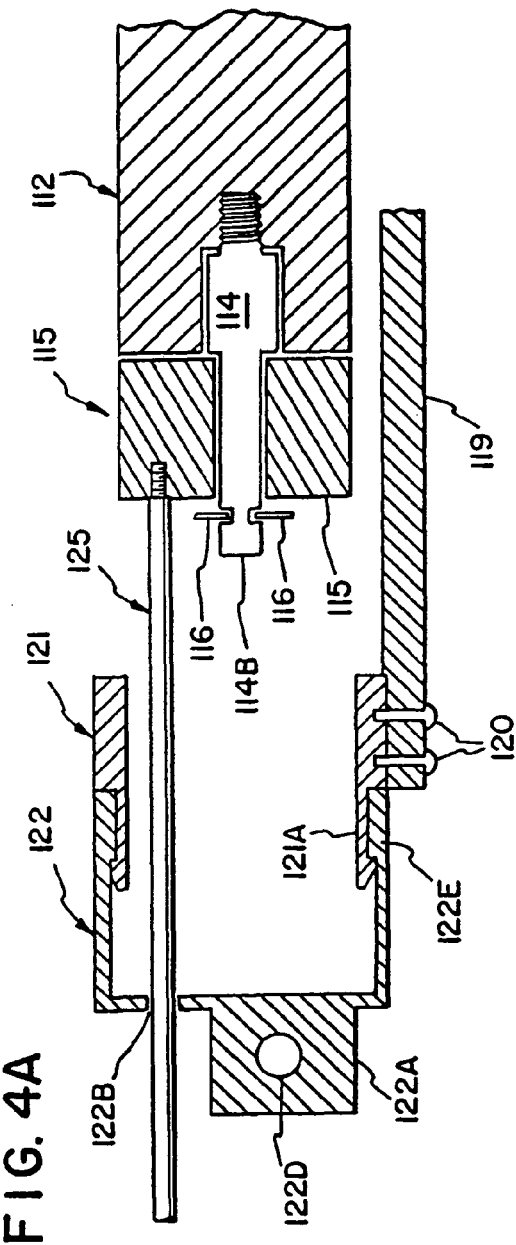
FIG. 4A illustrates a sectional side view of the collar pivot holder, collar pivot support, collar pivot wheel, channel pin holder and channel pivot.

Referring additionally to FIGS. 4 and 4A, collar pivot holder 112 is a substantially cylindrical piece which is located below the collar moving pivot 111, and which is slidably mounted in the proximal cylindrical chamber 102E. Collar pivot holder 112 has a distal end with an internally threaded axial hole 112A, and a proximal end with a longitudinal slot 112B for receiving depending plate 111C of the collar moving pivot, and transverse aperture 112C adapted to receive pin 113 for mounting the depending plate 111C.

Collar pivot holder 112 provides a means to transmit longitudinal movement from the collar moving pivot to the collar pivot wheel 115, which is connected by means of the collar pivot support 114.

Collar pivot support 114 has a longitudinally projecting threaded bolt portion 114A at its proximal end for mounting into the hole 112A of the collar pivot holder 112. At its distal end, collar pivot support has a longitudinally projecting pin 114B with a circumferential notch 114C for engaging E-ring retainer 116. Pin 114 is disposed through axial aperture 115A of the collar pivot wheel 115, and the distal end of the pin with notch 114C projects out through the distal end of said aperture 115A where E-ring retainer 116 is clipped onto said notch thereby maintaining collar pivot wheel 115 on pin 114B. Collar pivot support 114 not only provides a means for connecting collar pivot wheel 115 and collar pivot holder 112 so that longitudinal motion may be transferred, but also provides an axis (pin 114B) around which collar pivot wheel 115 may freely rotate.

Collar pivot wheel 115 is a substantially cylindrical piece slidably mounted in the proximal cylindrical chamber 102E of body 102. Concentric aperture 115A extends from the proximal to distal end of said collar pivot wheel for receiving pin 114B. Collar pivot wheel 115 further has eccentric hole 115B in its distal end for receiving mounting bolt 125A of the collar shaft 125 (FIG. 6). Collar pivot wheel 115 is movable both longitudinally within proximal cylindrical chamber 102E, and rotationally around pin 114B. Collar pivot wheel 115 transfers longitudinal motion to the collar shaft 125 for the purpose of clamping the jaws of the apparatus.

Channel pin holder 121 is a substantially cylindrical shaped piece slidably mounted in the distal cylindrical chamber 102D, and having a hollow axial interior. At its distal end, channel pin holder has a male snap-in plug 121A with contraction slots 121B for mounting into the proximal end of channel pivot 122. Channel pin holder 121 is mountable by means of screws 120 onto firing support shaft 119 and provides a means for transferring longitudinally movement from the firing support shaft 119 to the channel pivot for the purpose of firing the surgical fasteners. Channel pin holder 121 moves only longitudinally. The snap-in plug 121A serves as an axis around which the channel pivot 122 may rotate.

Firing support shaft 119 is an elongated substantially rectangular piece slidably mounted in the lower guideway 102G. Concave surface portion 119A at the distal end of the firing support shaft 119 is for mounting the channel pin holder 121, and has a curvature corresponding to the outside surface of the channel pin holder 121. Screws 120 are disposed through transverse apertures 119C in the firing support shaft 119, and into holes in the bottom of channel pin holder 121 for mounting said channel pin holder 121 to the firing support shaft 119. At its proximal end, firing support shaft 119 has a longitudinally extending threaded hole 119B for receiving threaded screw portion 118A of the plunger 118.

Firing support shaft transfers longitudinal movement from the plunger 118 to the channel pin holder 121 for firing the fasteners.

Plunger 118 is a rod having threaded screw mounting portions at both the distal and proximal ends. The distal screw portion 118A is for mounting to the threaded hole 119B in the firing support shaft 119. The proximal screw portion 118B is for mounting a push button 117 by means of central threaded aperture 117A in the push button. The plunger rod extends proximally outside the proximal opening 102C in the body 102.

Figure 8:
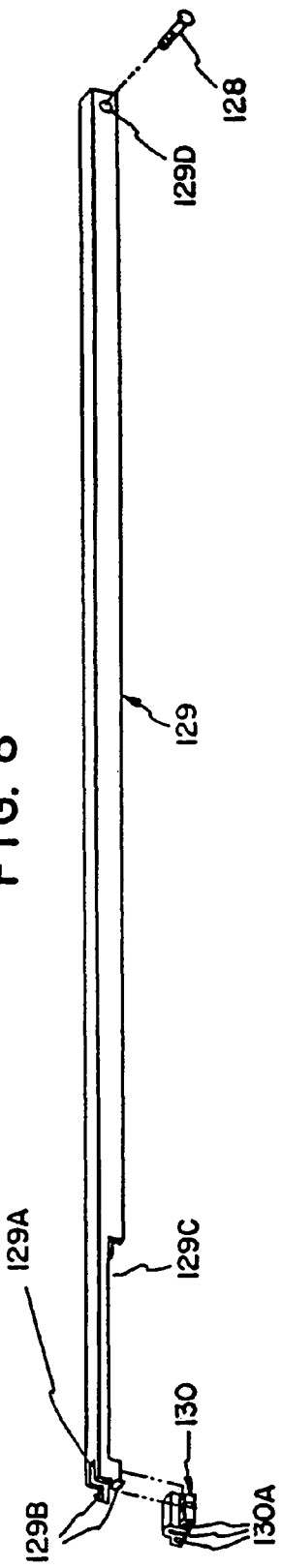
FIGS. 8 and 9 illustrate the cam bar channel, cam bars, knife and cam bar adapter.

Channel pivot 122 is a substantially cylindrical piece located within the distal cylindrical chamber 102D of frame 102. At its proximal end, channel pivot 122 has opening 122C to serve as a receptacle for snap-in portion 121A of the collar pin holder 121 upon which the channel pivot 122 is rotatably mounted. As can be seen from FIG. 4A, receptacle portion 122C has a circumferential lip 122E to interlock with the snap-in portion 121A. At its distal end channel pivot 122 has a stud 122A for mounting the proximal end of cam bar channel 129 (FIG. 8). Mounting screw 128 is disposed through transverse aperture 122D to secure the cam bar channel 129. Collar shaft 125 is disposed through aperture 122B.

Channel pivot 122 provides a means for transferring longitudinal movement from the channel pin holder 122 to the cam bar channel 129 for the purpose of firing the surgical fasteners. Channel pivot 122 also provides a means to rotate the cam bar channel 129 and collar shaft 125 around the longitudinal axis of the instrument.

Thumbwheel 123 is a disk shaped piece rotatably mounted in a circumferential thumbwheel mounting notch 102H. Thumbwheel 123 has a distally extending cylindrical projection 123B, rectangular slot 123A, detents 123C transverse to slot 123A, projecting distally from the cylindrical projection 123B, and a circumferential surface 123D which partially projects through elongated notch 102A. Thumbwheel 123 can be rotated by manually applying a turning force to the portion of the circumferential surface 123D which projects through the elongated notch. Upon being rotated thumbwheel 123 will thereupon turn the cover, cam bar channel, collar shaft, around the longitudinal axis of the instrument for the purpose of imparting rotation to the endoscopic portion of the apparatus distal to the frame.

Figure 5:
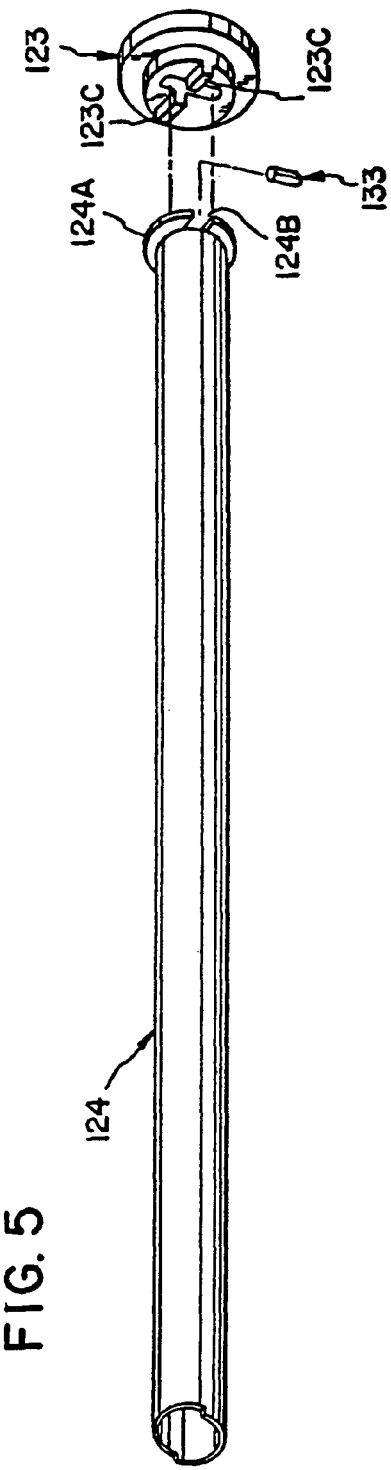
FIG. 5 shows the tubular cover.
Figure 5A:
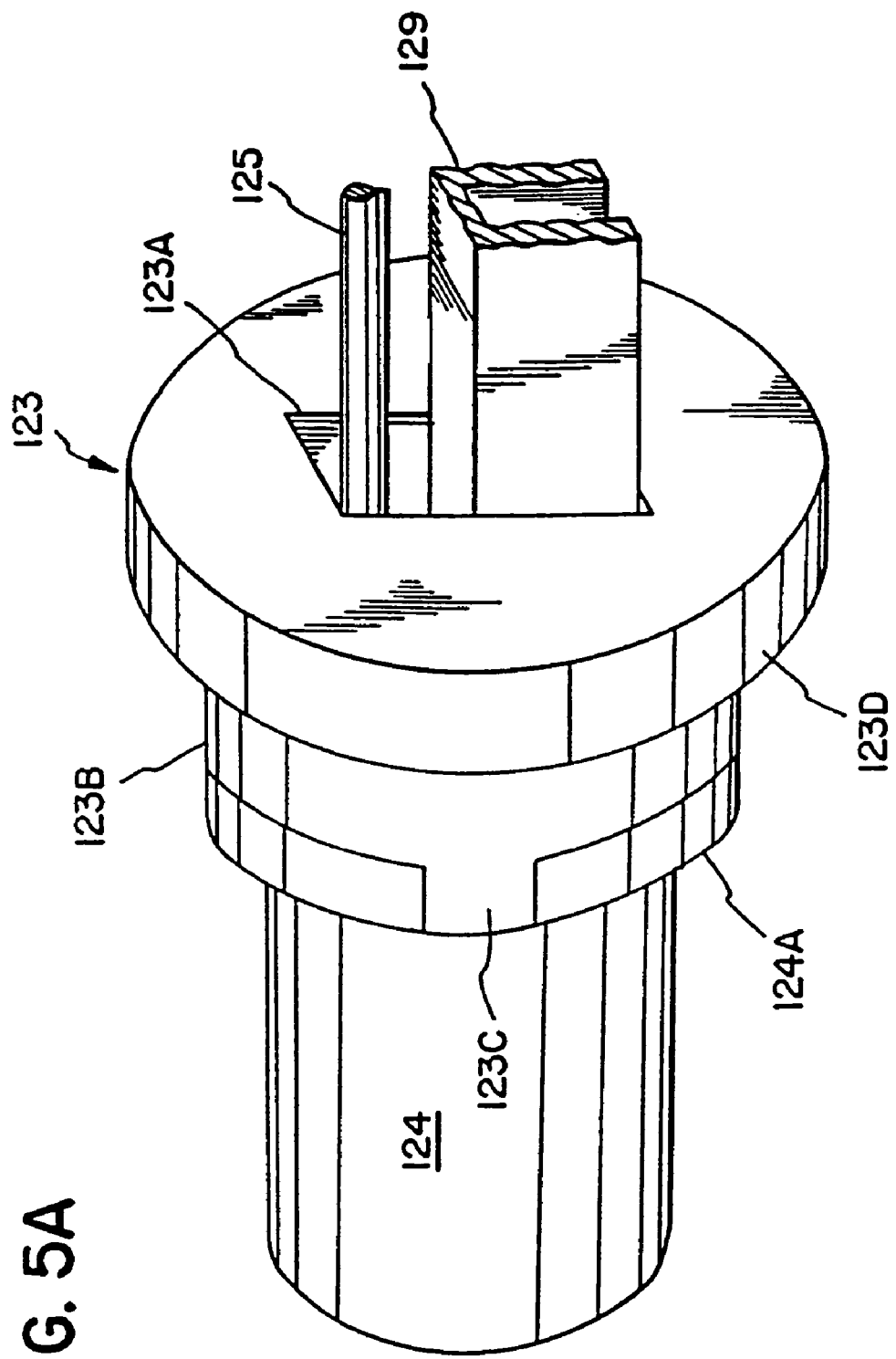
FIG. 5A illustrates the connection between the cover and thumbwheel.

Referring additionally now to FIGS. 5 and 5A, cover 124 is a relatively long tubular piece having a diameter appropriate for use in endoscopic surgical procedures and projecting distally through the distal opening 102B of the frame in alignment with the longitudinal axis of the instrument. At its proximal end, cover 124 has a flange 124A which has notches 124B to cooperatively engage detents 123C of the thumbwheel 123. Flange 124A is mounted flush against cylindrical projection 123B of the thumbwheel. Cover 124 is rotatably mounted as to turn in conjunction with the rotation of the thumbwheel. Collar shaft 125 and cam bar channel 129 extend longitudinally through the interior of the cover 124. Cover 124 provides a means for enclosing the collar shaft 125 and cam bar channel 129 to prevent them from contacting extraneous body tissue while the instrument is being used.

Referring additionally to FIGS. 6 and 7, collar shaft 125 is a relatively long rod in parallel alignment with the longitudinal axis of the instrument and having a proximal end with a threaded screw portion 125A for mounting to the collar pivot wheel 115, as discussed above, and a distal end with a screw portion 125B for mounting to the tapped hole 126A in collar plug 126. Via collar plug 126, collar shaft 125 transmits longitudinal motion to the collar 124 for the purpose of closing the jaws of the instrument to secure the target body tissue. Collar shaft 125 moves longitudinally, and it may be turned around the instrument axis although it does not rotate relative to its own axis.

Collar plug 126 provides a means for connecting collar shaft 125 to collar 127. Collar plug 126 has a threaded aperture 126A for mounting screw portion 125B of the collar shaft 125, and distal radial projections 126 which mount in circumferential slots 127A in the collar 127.

Collar 127 is a substantially tubular piece located distally to the cover 124 and aligned with the longitudinal axis of the instrument. Collar 127 has circumferential slots 127A in proximity to the proximal end of the collar 127, and a distal camming edge 127B. As seen in FIG. 15A, distal camming edge 127B provides a means for closing the jaws of the instrument to secure the target body tissue. This is discussed in more detail below.

Referring additionally now to FIG. 8, cam bar channel 129 is an elongated piece having an inverted U-shaped cross section and which is slidably mounted in housing 134. At its proximal end, cam bar channel 129 has a transverse aperture 129D for receiving fastening screw 128. The proximal end of the cam bar channel 129 is mounted to the rectangular mounting stud 122A of channel pivot 122 (FIG. 4). At its distal end, cam bar channel 129 has a gripping fork 129B and slot 129A. Gripping fork 129B and slot 129A provide a means of engaging and holding cam bar adapter 130. Longitudinal notches 129C allow the cam bar channel to move without interference from anvil pivot pin 135 (FIG. 11), as discussed below. Cam bar channel 129 transmits longitudinal motion from channel pivot 122 to the cam bars 131 and knife 132 for performing the tissue fastening operation.

Figure 9:
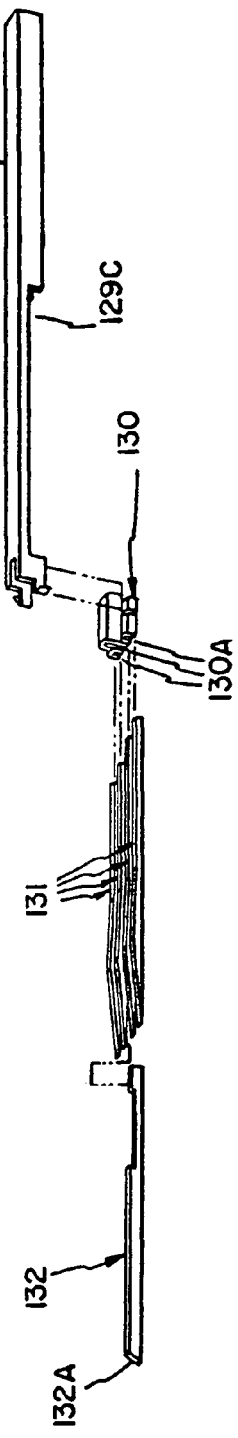

Referring to FIGS. 8 and 9, cam bar adapter 130 is mounted to the gripping fork 129B of the cam bar channel 129 and provides a means for holding the cam bars 131 and knife 132. Cam bars 131 are parallelly and longitudinally aligned. Their proximal ends are mounted in the longitudinal slots 130A of cam bar adapter 130. Knife 132, parallelly and longitudinally aligned with the cam bars 131, is also mounted to a slot 130A in the cam bar adapter 130. Knife 132 has a cutting edge 132A on its distal end.

Referring additionally now to FIGS. 10, 11, and 11A housing 134 is an elongated piece which is aligned with the longitudinal axis of the instrument. Housing 134 has a proximal end mounted to the cylindrical projection 123B of thumbwheel 123 by means of pin 133 (FIG. 5). At its distal end, housing 134 has a relatively wider section 134B for engaging and holding a cartridge assembly 137. Transverse aperture 134C receives anvil pivot pin 135. Housing 134 also has a longitudinally extending center guide rail 134A around which cam bar channel 129 is slidably mounted.

Anvil member 136 is an elongated piece which is pivotally mounted to the housing 134. At its distal end anvil member 136 has an anvil plate 136A with a tissue contacting surface 136E with staple forming depressions 136D (see FIG. 13). Anvil member 136 comprises arms 136B and, at the proximal end, a hinge 136C for pivotal mounting to housing 134 by means of anvil pivot pin 135 disposed through the hinge 136C and aperture 134C. Anvil member 136 is rotatable between an open position (see FIG. 15A) and a closed position (see FIG. 15B) where the anvil forming surface is brought into close cooperative alignment with the cartridge assembly 137. Anvil plate 136A also has a longitudinal center groove 136F to permit passage of knife 132. Anvil member 136 provides one of the jaws of the instrument for clamping and securing the body tissue to the fastened. Preferably, anvil 136 is provided with one or more tissue stops 140 which engage corresponding depressions, openings or indentations in housing 134 (see FIGS. 11, 15A). Tissue stops 140 help prevent over-insertion of tissue into the jaws.

Figure 13:
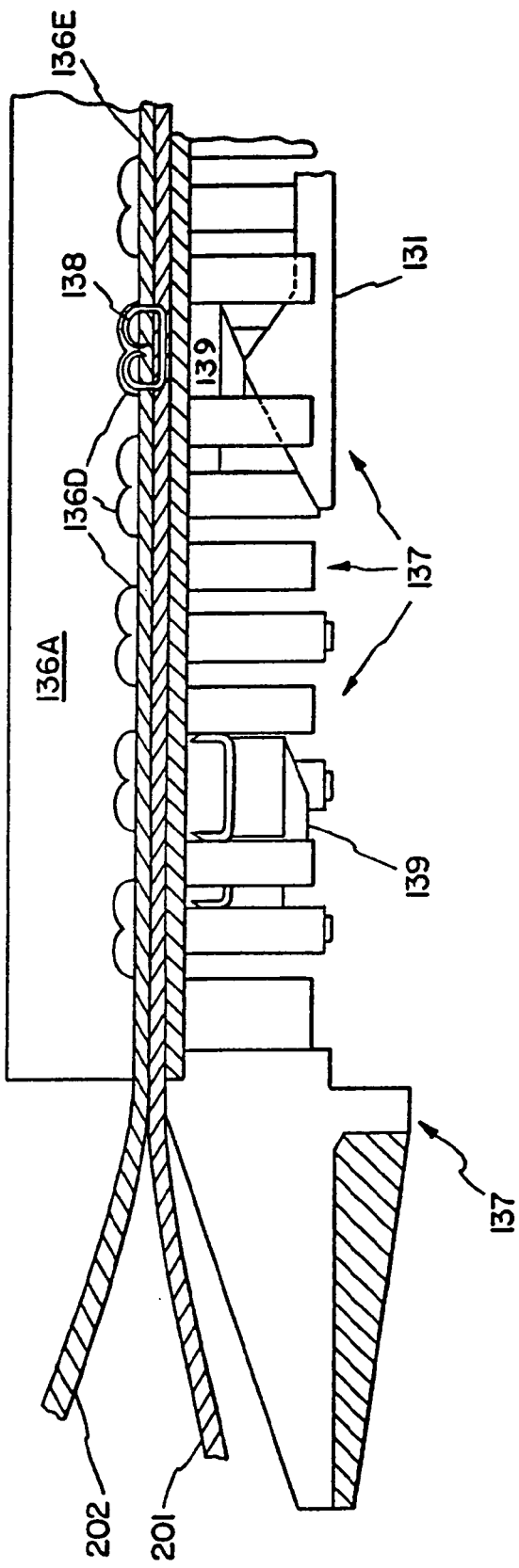
FIG. 13 illustrates a side view of the cartridge.
Figure 16:
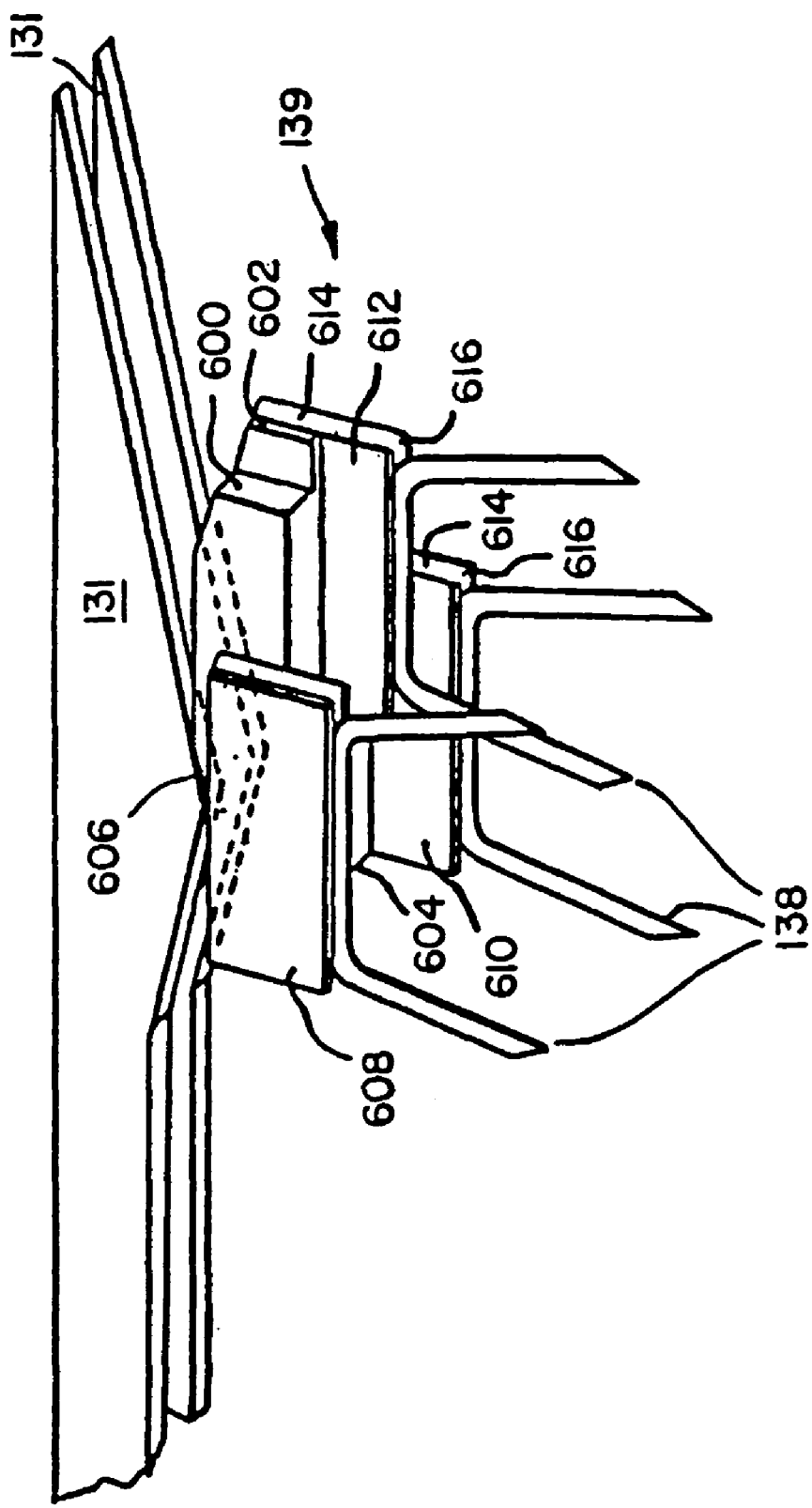
FIG. 16 illustrates a three staple drive member that can be used with the present invention.

Referring additionally now to FIGS. 12, 13 and 14, the cartridge assembly comprises a cartridge 137 with alignment plate 140, pusher elements or staple drivers 139, and surgical fasteners or staples 138. The staples 138 and pushers 139 are disposed within grooved slots 137A such that as the cam bars 131 move distally and longitudinally through the cartridge 137, pushers 139 are driven up through the grooved slots 137A driving staples 138 through the body tissue layers 201 and 202 which are to be joined, and into anvil plate 136A where the legs of the staples are crimped in staple forming depressions 136D. Alignment plate 140 serves as a cover to keep the staple drivers aligned within cartridge 137. Preferably, cartridge 137 contains two rows of staple pusher elements, with each staple pusher element acting on three staples. One such staple pusher element 139 is illustrated in FIG. 16. The preferred staple drive member there illustrated includes a body portion 600 having a distal end 602, a proximal end 604 with at least one camming surface 606, and three substantially rectangular pusher plates 608, 610, 612 aligned in the direction of cam motion. Pusher plates 608, 610 are laterally aligned on either side of body portion 600 and have an end coterminous with the body portion proximal end 604. The middle pusher plate 612 has an end coterminous with the body portion distal end 602. None of the pusher plates extend the full length of the body portion. Preferably, each pusher plate also includes guide rails 614 and a staple cradling notch 616. Guide rails 614 are received by and slide in corresponding slot portions of the cartridge. As shown in FIG. 16, each staple drive member is preferably driven by a double cam bar.

A wide variety of staple designs, shapes, sizes and arrangements may be used in the hereinafter described embodiments of the present instrument. For example, the staple pitch, i.e. the midpoint distance between corresponding staples, may be varied along with variations in staple length and the arrangement of the staples in the cartridge 137 in order to accommodate different applications.

FIG. 14 illustrates the surface of the cartridge 137 which comes in contact with body tissue. Grooved slots 137A terminate in openings through which the staples 138 are ejected. Groove 137B guides the movement of knife 132 through the cartridge.

As will be appreciated from the layout of slots or grooves 137A shown in FIG. 14, the preferred arrangement including two rows of staple drive member, each acting on three staples, results in six rows of staples with three overlapping staggered staple rows on each side of knife groove 137B. Placing three staggered overlapping rows of staples on either side of the incision obtains improved tissue holding strength and hemostasis.

A first alternative embodiment of the invention is illustrated in FIGS. 17-31. In the embodiment there shown the endoscopic portion 300 of the instrument is detachable from the frame and handle portion 301 of the instrument (see FIGS. 17 and 24). Endoscopic portion 300 preferably constitutes a disposable unit, the frame and handle portion of the instrument being reusable with replacement endoscopic portions.

Figure 17:
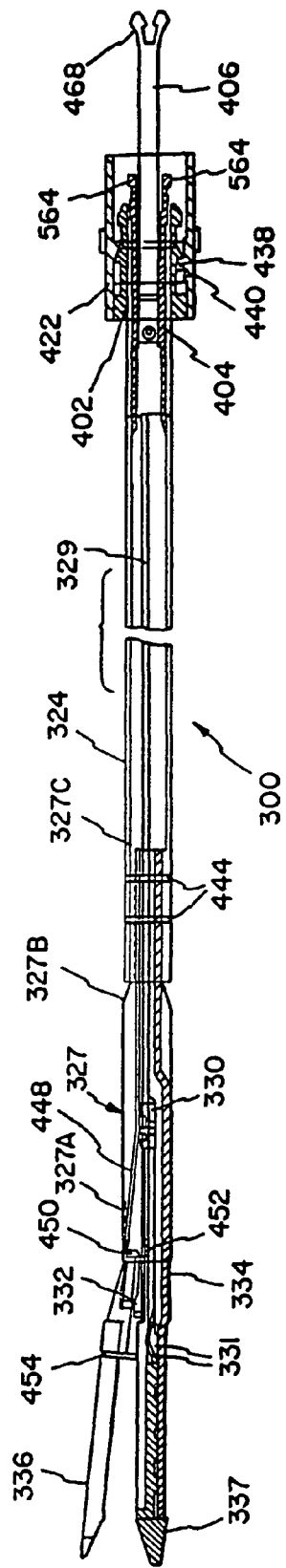
FIG. 17 illustrates a sectional view of the endoscopic portion of the instrument in accordance with a first alternative embodiment of the invention.

Referring now to FIG. 17, a sectional side view of endoscopic portion 300, the endoscopic portion has a housing 324 mounted at the proximal end to a collet 402. At the distal end of the endoscopic portion, housing 324 supports a cartridge housing 334 and an anvil 336. In this embodiment, a clamping tube 327 has a clamping portion 327A of substantially the same outer diameter as housing 325, a tapered section 327B and a shaft portion 327C having a narrow diameter configured and dimensioned to slide axially within housing 324. The proximal end of the narrow diameter shaft section 327C is fixedly mounted to a clamp tube snap 404. A cartridge 337 is mounted to cartridge housing 334 and engages cam bars 331 and a knife 332. As shown in FIG. 17, cam bars 331 preferably are staggered longitudinally relative to one another in order to improve the balance of forces generated in driving the preferred three staple drive members to eject three staggered parallel rows of staples on either side of the incision formed by knife 332. Similar to the first described embodiment, cam bars 331 and knife 332 engage and are supported by a cam bar adapter 330 which, in turn, engages the distal end of a cam bar channel 329. The proximal end of cam bar channel 329 is fixedly mounted to a channel adapter 406.

Figure 18:
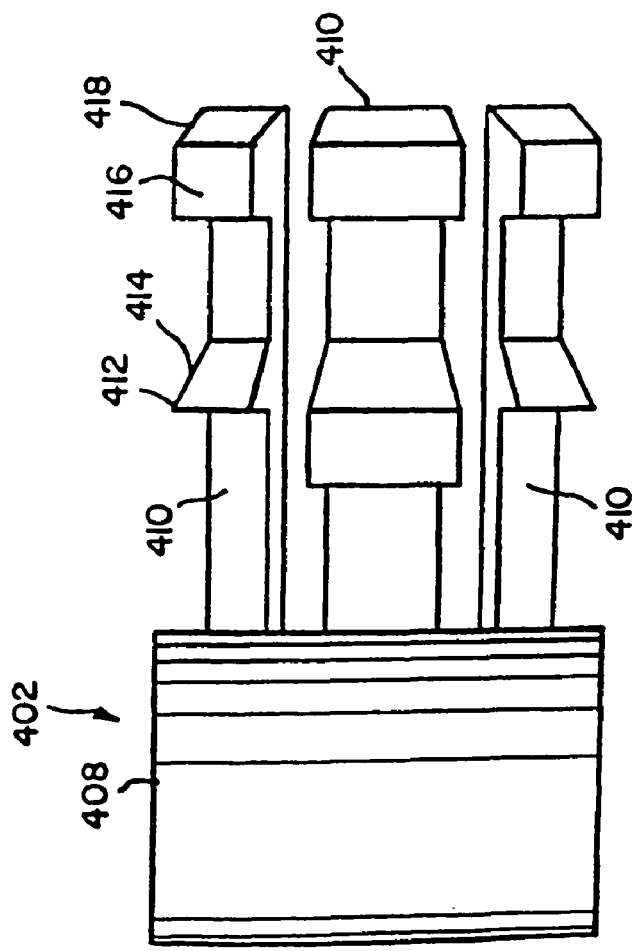
FIG. 18 illustrates a side view of the collet in accordance with the first alternative embodiment of the invention.
Figure 20:
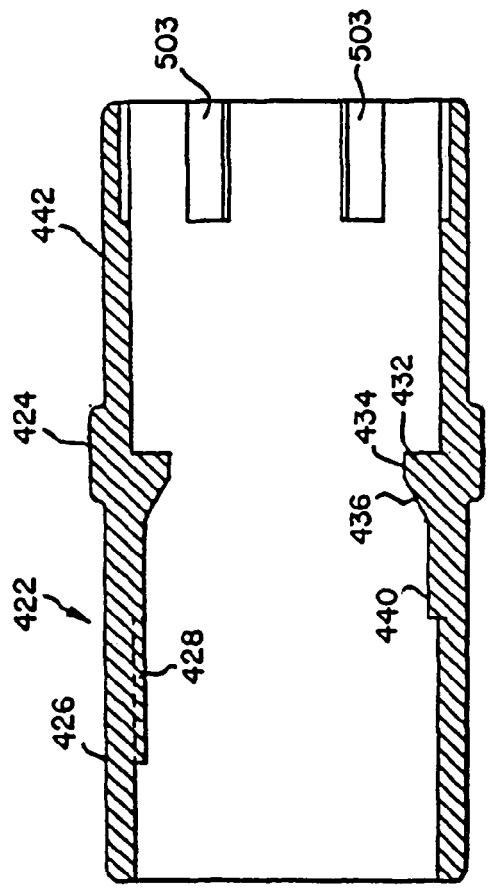
FIG. 20 illustrates a sectional side view of the sleeve in accordance with the first alternative embodiment of the invention.

As shown in FIG. 18, collet 402 is substantially cylindrical in shape having a cylindrical support section 408 at the distal end thereof and a plurality of collet fingers 410 extending longitudinally in the proximal direction. Each collet finger 410 has an outwardly projecting midsection portion 412 with an inclined surface 414 projecting axially inward in the proximal direction. Each collet finger also has an outwardly projecting proximal flange portion 416 terminating at an inclined surface 418 extending axially inward in the proximal direction.

Figure 19:
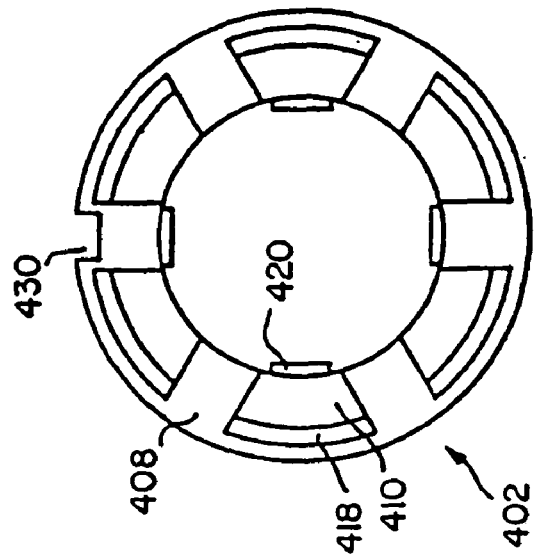
FIG. 19 illustrates a proximal end view of the collet of FIG. 18.

FIG. 19 is a proximal end view of collet 402, illustrating six collet fingers 410 configured as sections of a cylinder. Collet 402 and, more specifically, collet fingers 410 are preferably made of plastic and may be flexed inwardly from their normal, or rest position. Fingers 410 have memory and return to their rest position when the flexing force is released.

The inner diameter of cylindrical support section 408 is configured to accept the proximal end of housing 324. The proximal end of housing 324 is fixed to cylindrical support section 408 by any appropriate means, including but not limited to friction fit and/or engagement of one or more projections or ribs 420 on the inner surface of cylindrical support section 408 (see FIG. 19) with corresponding openings or slots on the housing 324.

Referring again to FIG. 17, collet 402 is disposed within and engages an outer sleeve 422 such that sleeve 422 is rotationally immovable relative to the collet but is longitudinally movable relative to the collet with a limited range of motion. As shown more particularly in FIG. 20, sleeve 422 has an outer gripping surface including a gripping ring 424.

Sleeve 422 has a distal portion 426 including an inwardly extending longitudinal rib 428 which engages a longitudinal slot 430 on the outer surface of the collet cylindrical support section 408 (see FIG. 19). As will be apparent, engagement of rib 428 and slot 430 prevents rotational movement of the sleeve 422 relative to the collet and vice versa. Sleeve 422 also has an inwardly projecting flange 432 at the sleeve midsection. Flange 432 has an area 434 of minimum diameter which corresponds to and engages the outer diameter surface of collet fingers 408 between outwardly projecting flanges 412, 416 (see FIG. 17). Flange 432 also has an inclined surface 436 projecting axially inward in the proximal direction. Inclined surface 436 substantially corresponds to and engages inclined surface 414 on collet fingers 410 (see FIGS. 17 and 18). In order to limit the range of longitudinal motion of sleeve 422 relative to collet 402, proximal and distal limiting stops 438, 440 are provided. Proximal limiting stop 438 engages the distal flat surface of the outwardly projecting midsection 412 of one or more collet fingers 410, thereby limiting longitudinal motion of the sleeve in the proximal direction. Distal limiting stop 440 abuts the proximal flat surface of collet cylindrical support section 408, thereby limiting the longitudinal motion of the sleeve in the distal direction.

Between these two extreme positions, limited longitudinal motion of the sleeve in the distal direction from the position illustrated in FIG. 17 is permitted, such that inclined surfaces 414, 436 exert axially inward force on collet fingers 410. In this manner, collet fingers 410 and, more particularly, the proximal ends of collet fingers 410, may be flexed inwardly from their rest or memory position for reasons to be discussed hereinafter.

The proximal section 442 of sleeve 422 has an inner diameter which is configured and dimensioned to accept and surround a corresponding outer tube projection on the frame with unencumbered rotational motion between the sleeve and the frame.

Referring again to FIG. 17, radial housing support pins 444 extend through the cylindrical interior of housing 324 near the distal end thereof. Pins 444 extend through longitudinal slots 446 on clamping tube 327 (see FIG. 21) and a similar slot in channel 329 (not shown). The proximal end of cartridge housing 334 is fixedly mounted to housing 324 by housing support pins 444. At the distal end, cartridge housing 334 supports cartridge 337. Housing support pins 444 also affix the proximal end of an anvil leaf spring 448 to housing 324. The distal end of spring 448 supports anvil 336. As shown in FIG. 17, anvil spring 448 acts as a leaf spring to bias the anvil into the open position there shown.

Preferably, at least one pair of corresponding anvil alignment guides, shown as alignment pin and slot 450, 452 are provided on the anvil and cartridge. Alignment guides 450, 452 ensure proper alignment of the anvil and cartridge tissue contacting surfaces so that staples ejected from the cartridge accurately engage corresponding staple forming grooves in the anvil. Also preferred are one or more tissue stops 454 to ensure proper placement of the body tissue between the jaws without over-insertion of the tissue beyond the tissue contacting surfaces of the anvil and cartridge.

Clamp tube 327 surrounds the proximal portion of the anvil, anvil spring and cartridge housing in a manner similar to the first described embodiment, and moves longitudinally between the open position shown in FIG. 17 to a distal, closed position clamping the upper jaw closed against the lower jaw (see FIGS. 15A and 15B). In the latter position body tissue is clamped between the anvil and cartridge in the manner illustrated in FIG. 13.

Figure 21:
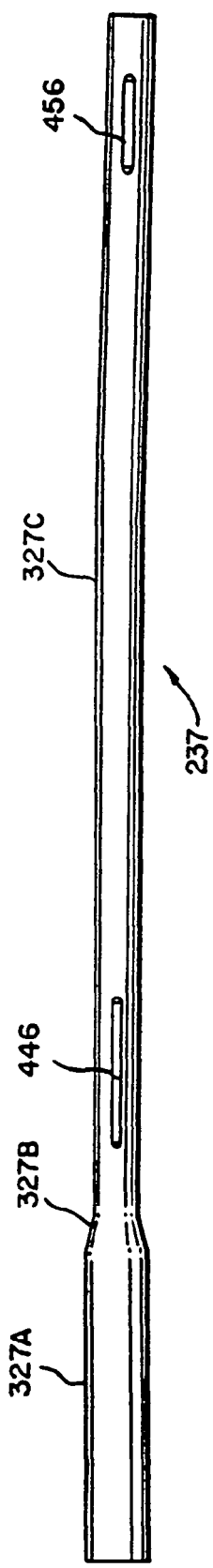
FIG. 21 illustrates a top plan view of the clamp tube of the first alternative embodiment of the invention.

As shown in FIGS. 17 and 21, clamp tube 327 has a clamping portion 327A with an outer diameter substantially the same as housing 324. At the proximal end of clamping portion 327A clamp tube 327 has a tapered section 327B which joins clamping portion 327A to narrow diameter shaft portion 327C. Clamping portion 327A and shaft potion 327C are substantially cylindrical. Shaft portion 327C has an outer diameter smaller than the inner diameter of cylindrical housing 324, thereby permitting longitudinal movement of the clamping tube relative to the housing. As shown in FIG. 21, shaft portion 327C includes longitudinal slots 446, 456. As previously described, housing support pins 444 extend through slots 446. It will be noted that slots 446 are configured to permit sufficient longitudinal movement of clamp tube 327 and channel 329 relative to housing 324 to close the instrument jaws and fire the instrument. Pins 444 isolate the anvil and cartridge housing assemblies relative to housing 324, and prevent longitudinal or rotational movement of the anvil or cartridge assemblies relative to the housing. Pins 444 also prevent rotational movement of the collar tube or channel relative to housing 324.

Figure 22:
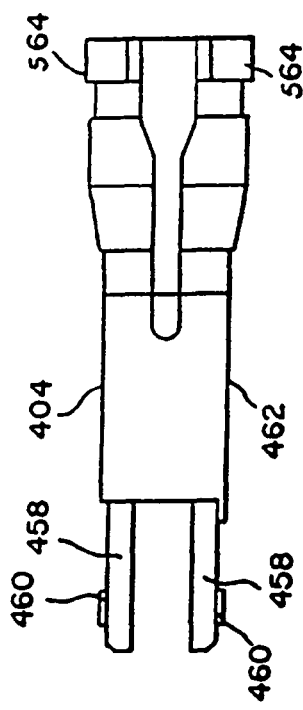
FIG. 22 illustrates a top plan view of the clamp tube snap of the first alternative embodiment of the invention.

The proximal end of clamp tube 327 is connected to the distal end of clamp tube snap 404 (see FIGS. 17 and 22). As shown in FIG. 22, clamp tube snap 404 includes two distal legs 458 which extend into the proximal end of clamp tube 324. Outwardly extending pins 460 isolate clamp tube 324 and clamp tube snap 404 relative to one another. Clamp tube snap 404 further includes a substantially cylindrical midsection 462 and clamp snap fingers 464. It will further be appreciated that inward deflection of collet fingers 410 by distal movement of sleeve 422 also inwardly deflects clamp snap fingers 464 from their rest position in FIG. 17.

Figure 23:
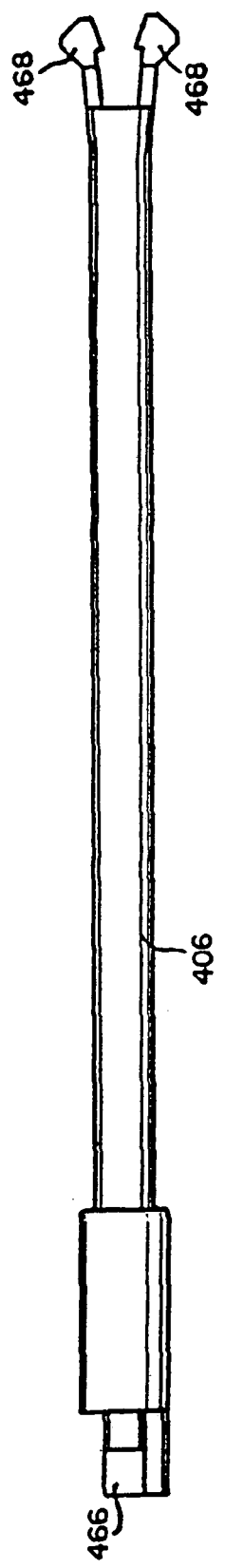
FIG. 23 illustrates a side view of the channel adapter of the first alternative embodiment of the invention.

Channel 329 is disposed within clamp tube 327 and is longitudinally movable therein for imparting longitudinal motion to cams 331 and knife 332. Referring to FIGS. 17 and 23, the proximal end of channel 329 is fixed to the distal end of channel adaptor 406, such as by tabs 466 on channel adaptor 406 engaging corresponding slots on channel 329 (not shown). The shaft of channel adaptor 406 extends longitudinally through the center of clamp tube snap 404 and terminates with a female snap-in receptor defined by prongs 468.

The preferred frame for this embodiment is shown in FIGS. 24-31.

Figure 25A:
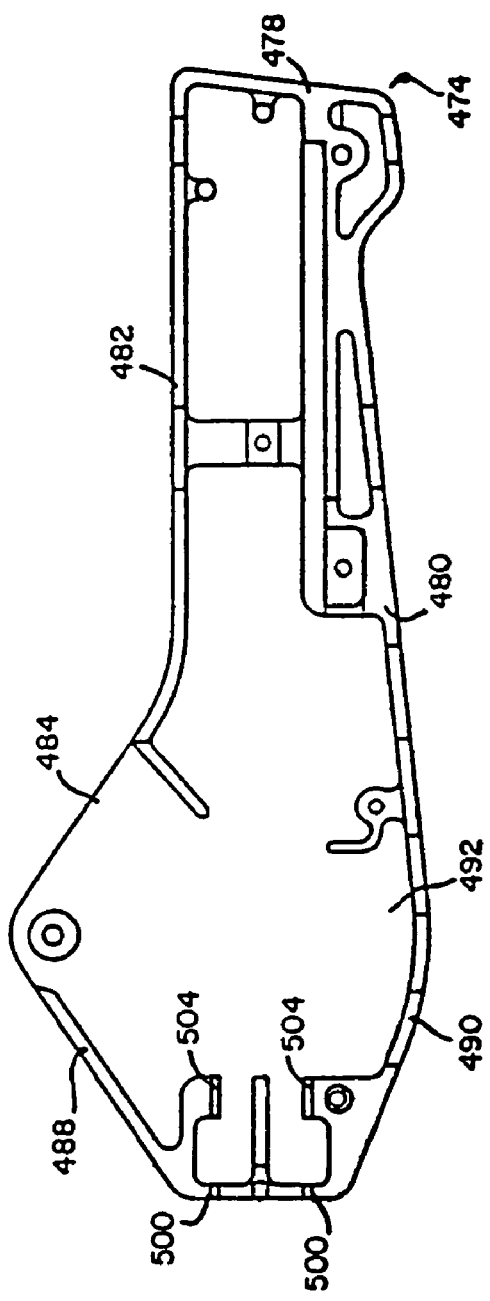
FIG. 25A illustrates a sectional view of the frame in accordance with the first alternative embodiment.
Figure 25B:
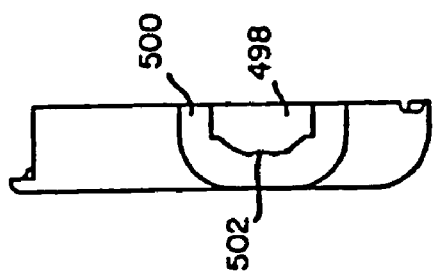
FIG. 25B illustrates a distal end view of the frame half illustrated in FIG. 25A.

As shown in FIGS. 24, 25A and 25B, the frame and handle assembly in this embodiment is configured with a double handle. In this embodiment, inner handle 470 controls the tissue clamping action of the instrument jaws, and outer handle 472 controls firing of the instrument. Frame 474, which may be molded and/or machined in whole or in part, is substantially rectangular with a closed proximal end 478, a lower gripping surface 480 and an upper, handle receiving surface 482. An opening 484 is provided to receive handles 470, 472 mounted to hinge pin 486. Handles 470, 472 may be biased in the open position, illustrated in FIG. 24, as by spring loading. The distal portion of opening 484 is defined by an upwardly extending lip 488. The lower surface of the frame includes a protruding bulbous region 490 distal to gripping surface 480. As explained in greater detail below, bulbous region 490 defines an interior cavity 492 sufficient to permit arcuate travel of the handles. The distal end of frame 474 terminates at a substantially flat surface having a distal opening 498 (see FIG. 25B). Preferably, frame 474 is cast and/or machined in two left and right halves fastened together by screws or rivets 496, 497, 499. Each frame half includes a distal inwardly projecting flange 500 and a longitudinal rib 502 which define distal opening 498 (see FIG. 25B). Inwardly projecting flange 500, in conjunction with the exterior walls of frame 474 and interior walls 504, define a distal frame chamber 506 to receive and support the proximal end of an outer tube 494.

Referring now to FIGS. 24, 26A and 26B, inner handle 470 includes a gripping tab portion 506 at the proximal end of an inner handle arm 508 and a lever arm portion 510. A hinge pin aperture 512 is provided at the distal end of arm 508 to receive hinge pin 486, such that inner handle 470 rotates about hinge pin 486 to obtain leveraging mechanical advantage at lever arm 510. As shown in FIG. 26B, a distal end view of the inner handle, lever arm portion 510 is formed in a substantially U-shaped configuration with a pair of lever arm forks 510A, 510B. Referring again to FIG. 26A, each leveraging fork includes and elongated slot 514 for receiving frame clamp tube pins 516 projecting from either side of a frame clamp tube 518 straddled by lever arm fords 510A, 510B.

Figure 27A:
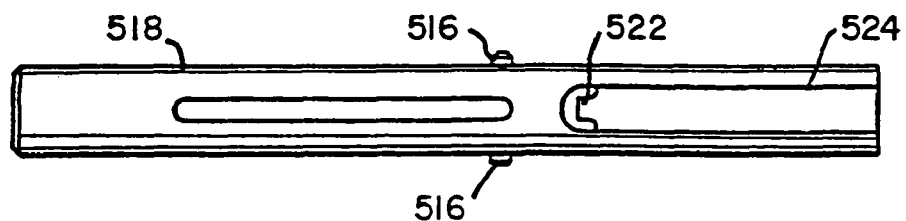
Figure 27B:
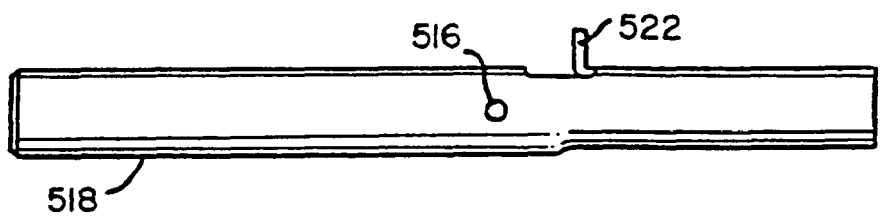
Figure 27C:
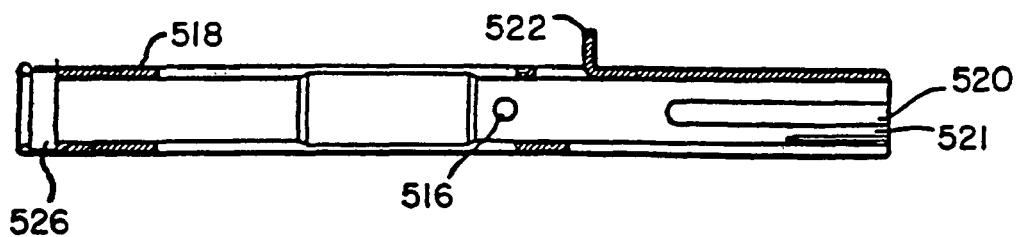

Frame clamp tube 518 is best described by reference to FIGS. 27A through 27E. FIG. 27A is a bottom view of frame clamp tube 518 showing clamp tube pins 516 projecting outwardly to either side to engage slots 514 on the inner handle lever arm portion. An elongated U-shaped slot 524 is provided for reasons explained later. As shown in FIG. 27B, a front side view of tube 518, a spring retaining pin 522 is formed and protrudes outwardly from the frame clamp tube. As shown in FIG. 27C, a side cross-section view of the frame clamp tube, the distal end of frame clamp tube 518 includes a circumferential recess 526 configured and dimensioned to receive clamp tube snap 564. FIG. 27D is a partial rear side view of the clamp tube showing the proximal end of the clamp tube. As there shown, the rear side of the clamp tube 518 includes a leaf spring slot 520 and a leaf spring cam 521. FIG. 27E is a partial rotated view of tube 518 showing cam 521. As shown, cam 521 is formed by bending a section of the tube wall to protrude outward from the circumference of the tube. Frame clamp tube 518 is longitudinally movable from the proximal position shown in FIG. 24 to a distal position to close the instrument jaws. The distal end of a clamp tube spring 519 engages spring retaining pin 522 and the proximal end of clamp tube spring 519 engages the screw mount 497. Thus, clamp tube spring 519 retains the frame clamp tube in the proximal position until force is exerted to move the tube to the distal position. As shown in FIG. 24, the distal end of frame clamp tube 518 is disposed within outer tube 494. In the proximal clamp tube position there illustrated, the distal end of the frame clamp tube is substantially aligned with the distal end of the cylindrical barrel of outer tube 494.

Figure 29:
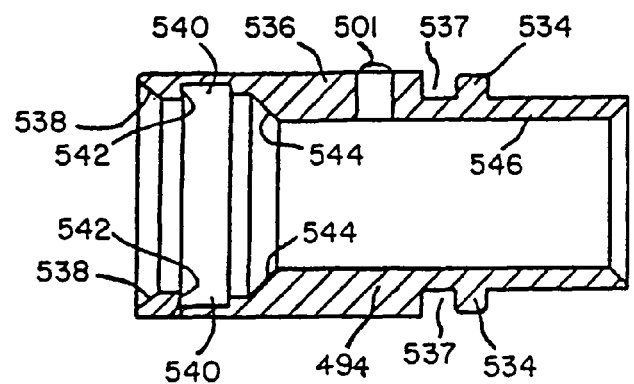
FIG. 29 illustrates a sectional side view of the outer tube of the first alternative embodiment.

Referring now to FIGS. 24 and 29, outer tube 494 is substantially cylindrical and engages the distal opening in frame 474. The proximal, frame engaging portion of outer tube 494 includes an annular flange 534 which, together with a distal outer tube body section 536, define an annular groove 537 for receiving inward flange 500 at the distal end of frame 474. Longitudinal ribs 502 on the frame (shown in phantom) engage the exterior outer tube surface to stabilize outer tube 494 relative to frame 474. Outer tube 494 is fixed relative to frame 474, as by compression fit and/or locking engagement of one or more corresponding sets of pins and holes, etc. Thus, outer tube 494 projects from the distal end of frame 474 but is fixed relative to the frame. The projecting distal end of outer tube 494 is configured and dimensioned to engage collet 402 on the endoscopic portion of the instrument (see FIG. 17). The outer diameter of body section 536 is configured and dimensioned to be inserted into sleeve 422, with collet fingers 410 simultaneously urged within outer tube 494 by inwardly inclined rim 538. As shown in FIG. 29, body section 536 includes collet finger recesses 540 having slightly inclined distal walls 542. Body section 536 further includes transition walls 544 between the collet finger receiving portion and the cylindrical barrel section 546. Cylindrical barrel section 546 has a uniform diameter from the proximal termination point of inclined walls 544 to the proximal end of outer tube 494. As stated, cylindrical barrel section 546 receives frame clamp tube 518 in concentric longitudinal sliding relation (see FIG. 24). The protruding distal portion of outer tube 494 also includes a small bump, protrusion or detent pin 501 for engaging one of detent slots 503 on the inner surface of sleeve 522 (see FIG. 20), such that sleeve 522 may be rotated between distinct detent positions relative to outer tube 494.

Figure 30B:
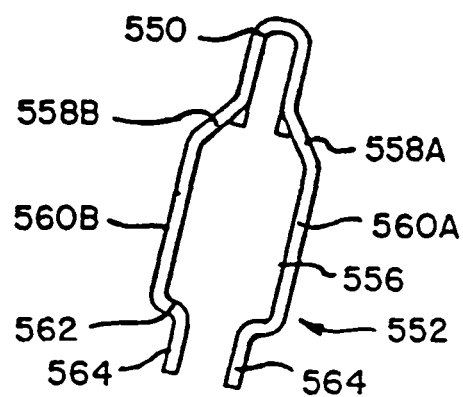
FIGS. 30A and 30B illustrate side and distal end views, respectively, of the outer handle of the first alternative embodiment.
Figure 30A:
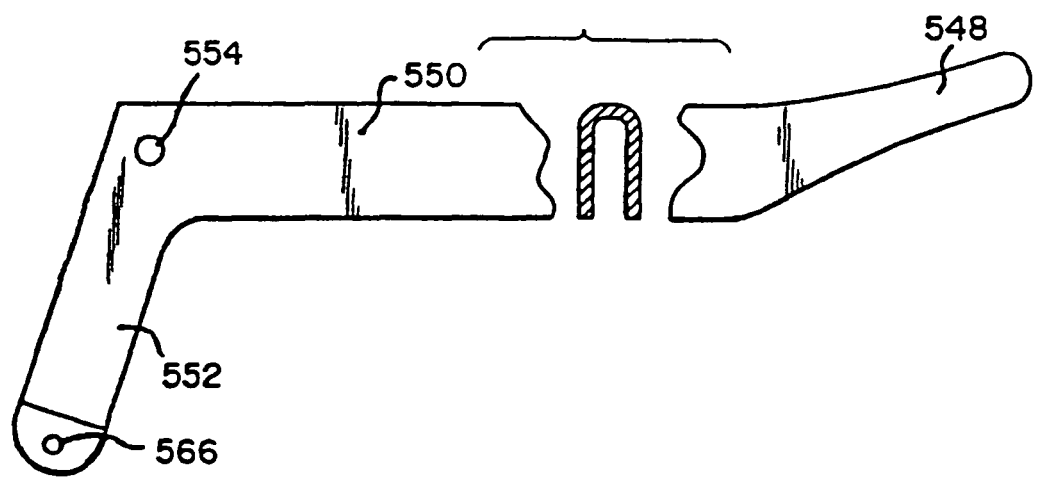

Outer handle 472 includes a proximal tab portion 548, a longitudinal arm portion 550, and a lever arm portion 552 (see FIGS. 24, 30A and 30B). The proximal end of longitudinal arm portion 552 terminates in tab 548, and the distal end of arm portion 550 includes a hinge pin aperture 554 for receiving hinge pin 486 (see FIG. 24).

As shown in FIGS. 30A and 30B, outer handle arm 518 is of substantially U-shaped configuration such that inner handle arm 508 may be received within the open interior of longitudinal arm section 550. Outer handle lever arm portion 552 is configured and dimensioned to have an open interior section 556 which surrounds the inner handle lever arm portion and clamp tube assembly. Open interior section 556 permits unrestricted longitudinal movement of the frame clamp tube in response to inner handle 470 independent from the action of the outer handle. To obtain open interior section 556, outer handle lever arm portion 552 includes outwardly flared regions 558A, 558B, substantially parallel body walls 560A, 560B and a neck region 562 terminating at distal end portions 564. Referring to FIG. 30A, each distal end portion 564 includes a sprocket wheel pin receiving aperture 566.

Referring again to FIG. 24, a sprocket wheel 568 is mounted on sprocket wheel pin 566 and engages a chain 570. One end of chain 570 is fixed to frame 474, as by being secured to a pin mount 572. The other end of chain 570 is fixed to a chain engaging tab 574. Chain engaging tab 574 is attached as a downwardly extending tab at the proximal end of a drive tube 576. Drive tube 576 is disposed within frame clamp tube 518 and slides freely relative thereto. As will be appreciated, when outer handle 472 is closed toward the upper frame surface 482 outer handle lever portion 552 is rotated in the distal direction. This motion causes sprocket wheel 568 to follow an arcuate path, within the open bottom region 592 of the frame, drawing chain 570 and, consequently, drive tube 576 in the distal direction. It will be noted that elongated opening 524 on the bottom of frame clamp tube 518 accommodates chain 570 to ensure free movement of the chain and frame clamp tube relative to each other. In addition, a drive tube spring 577 engages frame screw mount 499 and a pin (not shown) within drive tube 576 to retain the drive tube in the proximal position shown until the instrument is fired.

Figure 31:
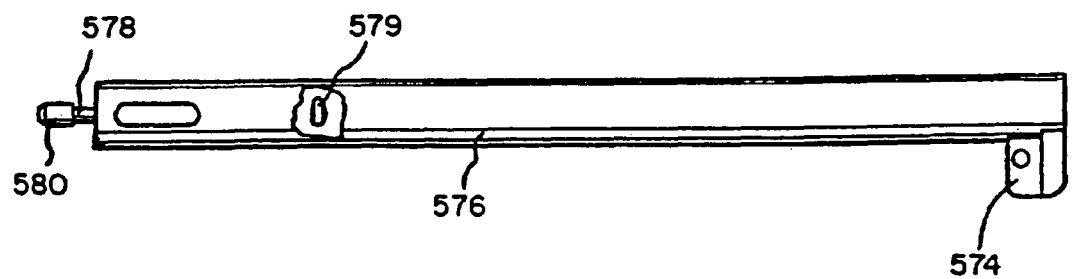
FIG. 31 illustrates a side view of a drive tube in accordance with the first alternative embodiment.

Briefly turning to FIG. 31, a side view of drive tube 576, the distal end of drive tube 576 is provided with an axially mounted protruding stem 578 bearing a push plug 580. Push plug 580 has a chamfered distal tip and is configured and dimensioned to be received between the proximal fingers 468 on channel adaptor 406 (see FIG. 17). As shown in the sectional portion of FIG. 31, the rear wall of drive tube 576 is provided with a safety locking slot 579.

Figure 28A:
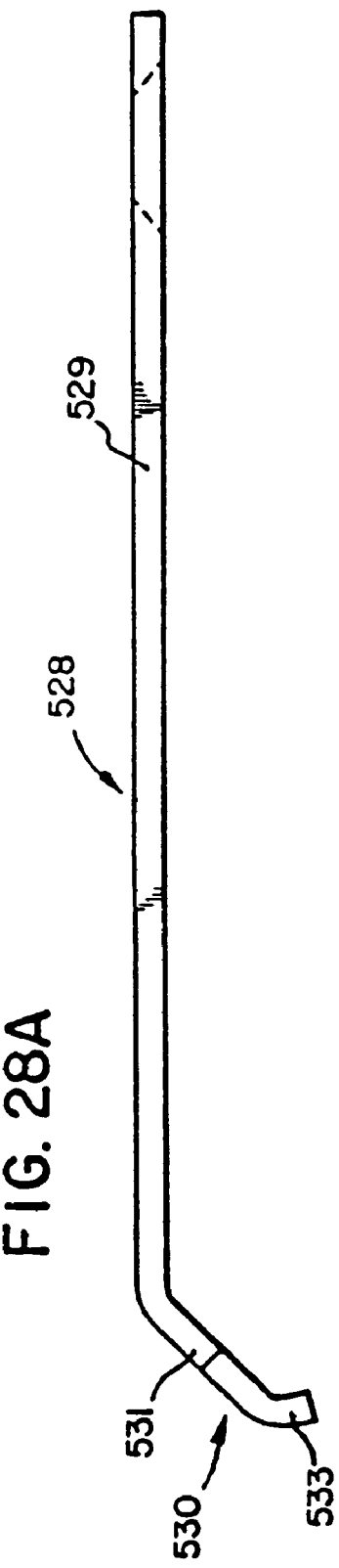
FIGS. 28A and 28B illustrate top and front views, respectively, of a frame leaf spring.
Figure 28B:
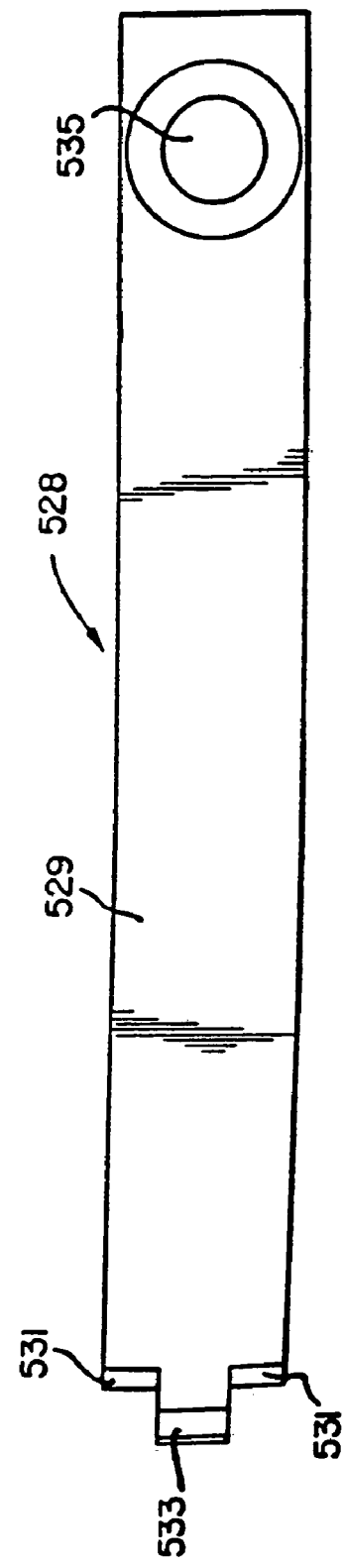
Figure 32A:
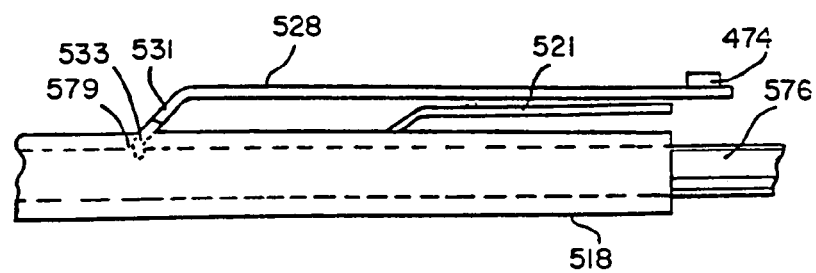
FIGS. 32A and 32B are top plan views of the frame clamp tube, drive tube and leaf spring illustrating proximal and distal frame clamp tube positions.
Figure 32B:
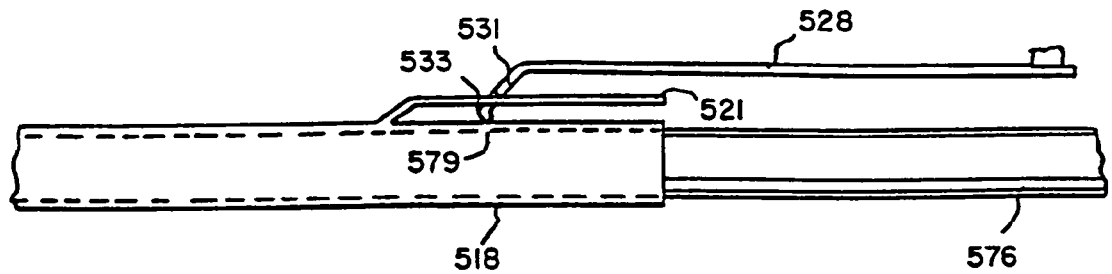

Advantageously, a safety locking mechanism is provided in this embodiment to prevent accidental firing of the instrument. Referring to FIGS. 28A and 28B, a leaf spring 528 is provided having a shank portion 529 and a curved tip 530. Curved tip 530 includes curved tip shoulders 531 of equal width to shank portion 529 extending approximately half the length of curved tip 530. Curved tip 530 further includes a central drive tube locking tip 533 protruding the full length of curved tip 530. Referring again to FIG. 24, the central region 532 outlined in phantom is a further partial sectional view looking beyond the far wall of drive tube 576. This relationship is better illustrated in FIGS. 32A and 32B, which are top plan views showing the frame clamp tube 518 in proximal and distal positions, respectively, relative to leaf spring 528. Leaf spring 528 is mounted to frame 474, as by screw mounting through screw hole 535 (see FIG. 28B), with curved tip 530 extending and biased toward frame clamp tube 518 and drive tube 576. In the proximal positions of tubes 518, 576, drive tube locking pin 533 extends through slot 520 on the far side of frame clamp tube 518 (see FIGS. 27D and 32A) and engages safety locking slot 579 on drive tube 576 (shown in phantom in FIG. 32A). Thus, in the proximal position, leaf spring 528 and locking pin 533 securely lock the drive tube in the proximal position and the instrument cannot be fired. However, leaf spring shoulder portions 531 do not extend into slot 520, but rather ride outside and to either side of slot 520. As frame clamp tube 518 moves from the proximal to the distal position, one of shoulder portions 531 rides onto leaf spring cam 521, thereby forcing leaf spring 528 away from tubes 518, 576 and disengaging locking pin 533 from safety locking slot 579 (see FIG. 32B). The leaf spring remains disengaged from the drive tube while the frame clamp tube is in the distal position, and returns to locking engagement with drive tube 576 whenever frame clamp tube 518 is returned to the proximal position. Advantageously, the force exerted by leaf spring 528 against cam 521 also tends to retain frame clamp tube 518 in the distal position so that the instrument will remain in the clamping position in preparation for firing. In the position shown in FIG. 32B, frame clamping tube 518 is in the distal position to clamp the instrument jaws closed, but drive tube 576 remains in the proximal position. However, because safety locking pin 533 is disengaged from slot 579 (shown in phantom), the outer handle may now be closed to move drive tube 576 distally to fire the instrument.

In order to assemble the frame and endoscopic portions of the instrument constructed in accordance with this embodiment, outer tube 494 is axially aligned with and inserted into sleeve 522 until collet fingers 510, and more specifically annular flanges 416 on the collet fingers, engage collet finger recesses 540. In addition, as outer tube 494 is inserted into sleeve 522, (i) clamp tube snap 564 is inserted into frame clamp tube 518 and mates with corresponding recesses 526 of the frame clamp tube; and (ii) channel adaptor 406 is axially inserted through the frame clamp tube until push plug 580 is seated between channel adaptor fingers 468.

It will be noted that, in this embodiment, endoscopic portion 300 can be rotated relative to frame 301 by exerting rotational force on sleeve 422. As stated, detent pin 501 and detent slots 503 on the outer tube and sleeve, respectively, define distinct rotational positions of the endoscope portion relative to the frame. As the endoscopic portion rotates, collet 402 rotates relative to outer tube 494, clamp tube snap 564 rotates within frame clamp tube 518, and push plug 580 rotates within channel adaptor fingers 468. It will further be noted that in the starting position of the handles illustrated in FIG. 24, springs 519, 577 bias the frame clamp tube and drive tube into their proximal positions. The related mechanical linkages also urge handles 470, 472 into the open positions illustrated. Drive tube locking pin 533 engages drive tube safety locking slot 579 to lock the drive tube in the proximal position and, hence, handle 572 in the open position, until the instrument jaws are clamped closed.

Tissue clamping is effected by closing inner handle 470 against upper frame surface 482. As inner handle 470 pivots about hinge pin 486, pins 516 travel in slots 514 to draw frame clamp tube 518 in the distal direction, overcoming the force of the frame clamp tube spring 519 to advance frame clamp tube 518 to its distal position. Because frame clamp tube 518 engages clamp tube snap 404, movement of frame clamp tube 518 imparts longitudinal motion to clamp tube 327, thereby closing anvil 336 against the tissue engaging surface of cartridge 337. Moving the frame clamp tube to the distal position also causes leaf spring cam 521 on frame clamp tube 518 to engage and urge leaf spring 528 away from drive tube 576, thereby disengaging drive tube locking pin 533 from safety locking slot 579.

Thereafter, the instrument may be fired by closing outer handle 472 against the inner handle and frame. During this motion, sprocket wheel 568, via chain 570, overcomes the force of drive tube spring 577 and imparts distal longitudinal motion to drive tube 576 and, hence, to channel adaptor 406. Of course, distal longitudinal motion of channel adaptor 406 drives channel 329, cams 331 and knife 332 to eject staples from the cartridge and form and incision between the rows of staples placed.

In this embodiment, endoscopic portion 300 may be detached from frame and handle portion 301 by exerting distal force on sleeve 422. As previously stated, during such motion inclined surfaces 414, 436 cooperate to flex the collet fingers inward, thereby releasing the collet from outer tube 494. Collet fingers 410 in turn flex clamp tube snap 464 to disengage the clamp tube snap from the frame clamp tube. Finally, as sufficient withdrawing force is developed, the distally inclined surfaces of channel adaptor fingers 468 cause the channel adaptor fingers 468 to release push plug 580, thereby permitting full disengagement of the endoscopic portion from the frame. Of course, the withdrawing force required to release channel adaptor fingers 468 should be sufficiently great that opening outer handle 472 after firing the instrument does not result in disengagement of the push plug from the channel adaptor.

Advantageously, the double-handle and safety locking pin arrangement of this embodiment prevents accidental firing of the instrument with the jaws in the open position. That is, because the outer firing handle is mounted over the clamping handle and cannot be closed without previously and independently closing the inner clamping handle, it is impossible to fire the instrument until the jaws are fully closed to clamp tissue.

A second alternative embodiment of the present invention is illustrated in FIGS. 33-64. In that embodiment the following features are provided. The cartridge assembly deactivates upon firing and is disposable and detachable from the tube assembly, the anvil assembly positively aligns and interfits with the cartridge assembly, the firing handle is provided with a manual safety and the clamp handle and firing handle interlock to prevent accidental firings. Each of these features is described in greater detail below.

Figure 33:
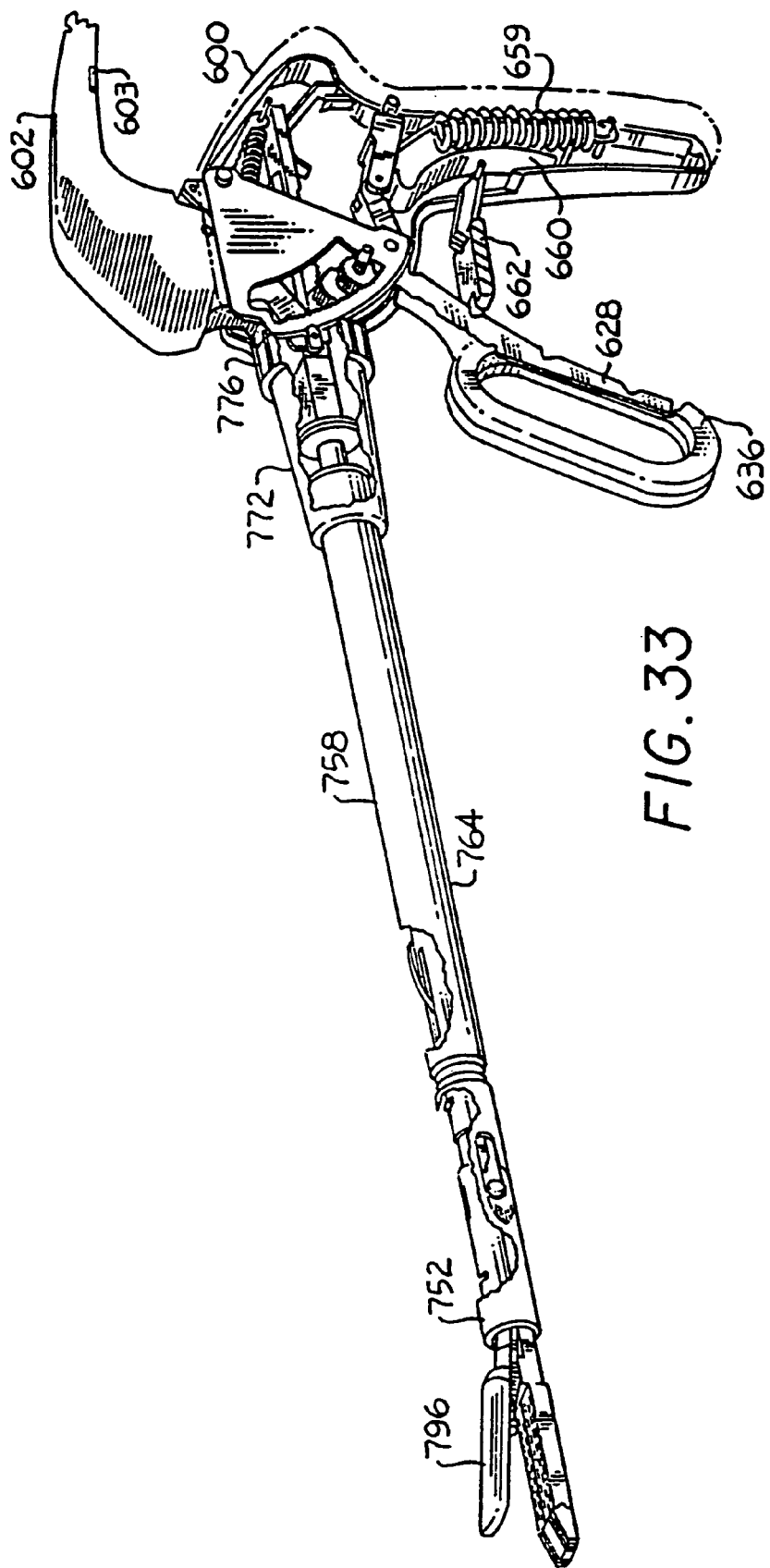
FIG. 33 illustrates a perspective cutaway view of an assembled stapler apparatus in accordance with a second alternative embodiment of the invention.
Figure 34:
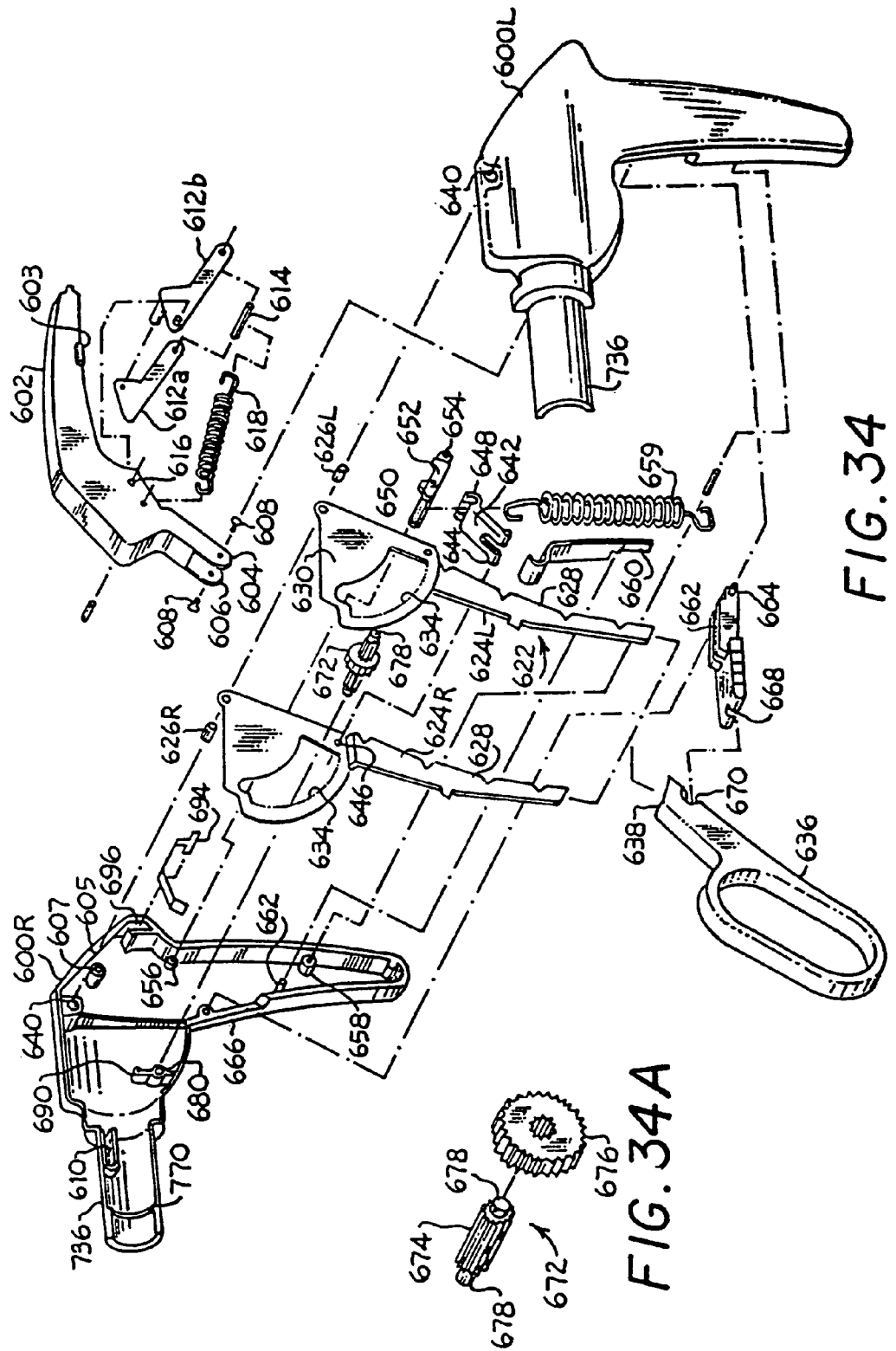

Referring now to FIGS. 33, 34 and 34A, frame 600 has two parts, a left portion 600L and a right portion 600R. These portions are optimally fastened together by means of ultrasonic welding along the peripheral contacting surfaces thereof, although screws, adhesives or other means of joining the two body parts also may be used. The frame 600 is of an overall size and shape convenient for being held in the hand.

A clamp handle 602 is pivotally mounted within the frame 600 for articulated movement between an open and a closed position. At a distal end, the clamp handle 602 is provided with a fork portion 604 having a transversely aligned aperture 606 for receiving clamp handle-to-tube pins 608. These pins 608 interfit in slots 610 in the sidewall of the frame 600 for longitudinal reciprocal movement therein. Link pin assembly 612, comprising a pair of links 612a and b interconnected by pin 614, attaches to clamp handle 602 at transverse aperture 616 and to frame 600 wherein pin 614 fits into and is retained by hole 607 in frame 600. A tensioned clamp spring 618 and clamp spring pin 620 connects clamp handle 602 with pin 614 of link pin assembly 612. This spring 618 assists in articulated movement of clamp handle 602 between the closed and open positions. Projections 603 on vertical sides of clamp handle 602 engage the circumferential edge 605 of frame 600 such that when the clamp handle 602 is pivoted down, it is releasably locked into position by the engagement of projections 603 and edge 605.

Gear handle assembly 622 includes left and right braced gear handles, 624L and 624R respectively, and connecting left and right gear handle pins, 626L and 626R. Left and right braced gear handles 624L and 624R are mirror images of each other and have a shank portion 628 and a web portion 630. Aperture 632 is formed in each web portion 630 having, on one internal surface of the aperture, an arcuate rack 634.

When assembled, shank portions 628 of left and right braced gear handles, 624L and 624R, contact in abutting relationship along an internal surface thereof to form a substantially Y-shaped structure with the web portions 630 being separated and substantially parallel. Firing handle 636 is provided with a slot 638 into which shank portions 628 are inserted and held. Transverse apertures 640 are formed in frame portions 600L and 600R to receive gear handle pins 626L and 626R respectively. The gear handle assembly is thus pivotal within frame 600 about transverse apertures 640.

Gear handle assembly 622 further comprises a gear handle link 642 having transverse projections 644 on a distal end thereof. These projections 644 are adapted to pivot about transverse bores 646 in the web 630 of braced gear handles 624 adjacent arcuate racks 634. Gear handle link 642 is further provided with parallel hooked projections 648 on a proximal end which projections are adapted to engage bar 650 on the distal end of a spring link 652. Transverse projections 654 mounted on the proximal end of spring link 652 interfit with holes 656 formed in the frame portions 600L and 600R. A firing handle return spring 659 is connected in tension within frame 600 from projection 658 to spring link bar 650 to provide a mechanical advantage to return the gear handle assembly to its prefiring position after it has been actuated.

A substantially S-shaped kicker spring 660 is mounted within frame 600 and flexes about pin 662. The spring 660 is deflected rearwardly by retracting gear handle assembly 622 and serves to "kick" the assembly back to the original unretracted position.

A manual safety 662 is provided to lock the firing handle 636 in the unfired position to prevent accidental retraction of the gear handle assembly 622. Safety 662 has transverse projections 664 on a proximal end thereof which projections fit into holes 666 in frame portions 600L and 600R to permit pivotal motion of the safety between an engaged position and a disengaged position. In the engaged position, a groove 668, formed in a distal end of safety 662, frictionally interfits with a mating structure 670 on the firing handle 636 to lock the handle in the extended position. To unlock the firing handle 636, the safety 662 is simply pivoted downward out of engagement.

Referring to FIG. 34A, there is shown a pinion spur gear assembly 672 comprising a pinion gear 674 interfitting with a spur gear 676 resulting in plural driving surfaces. Pinion gear 674 is further provided with projections 678 which interfit with holes 680 in frame portions 600L and 600R to facilitate rotational motion of the pinion spur gear assembly 672 about the transverse axis formed by projections 678.

Figure 38:
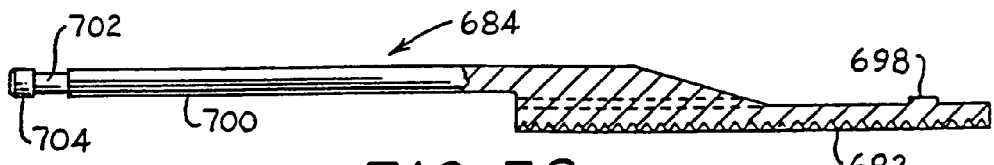
FIGS. 38-40 illustrate a side view in partial cross section, partial top view, and frontal view, respectively, of the rack rod.
Figure 40:
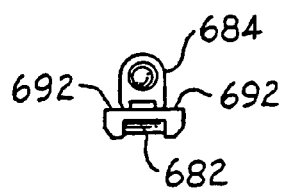
Figure 39:
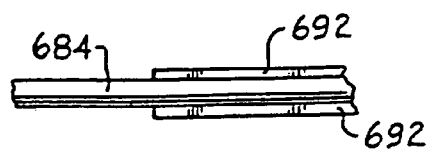
Figure 35B:
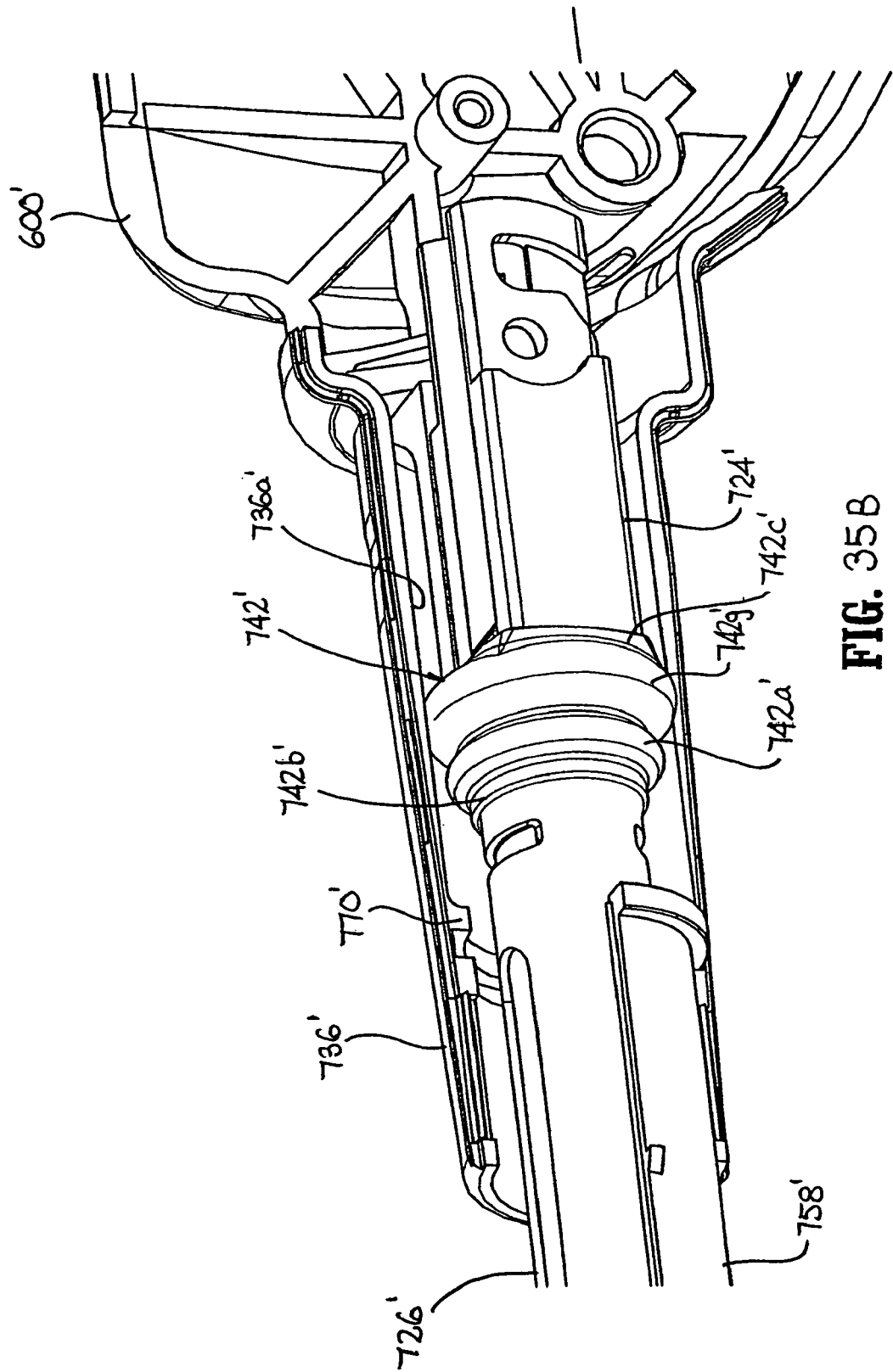
FIG. 35B is a side perspective view of an alternate embodiment of the proximal end of the endoscopic portion and the distal end of the frame with the left portion of the frame removed and the clamp tube or member in its retracted position.
Figure 35C:
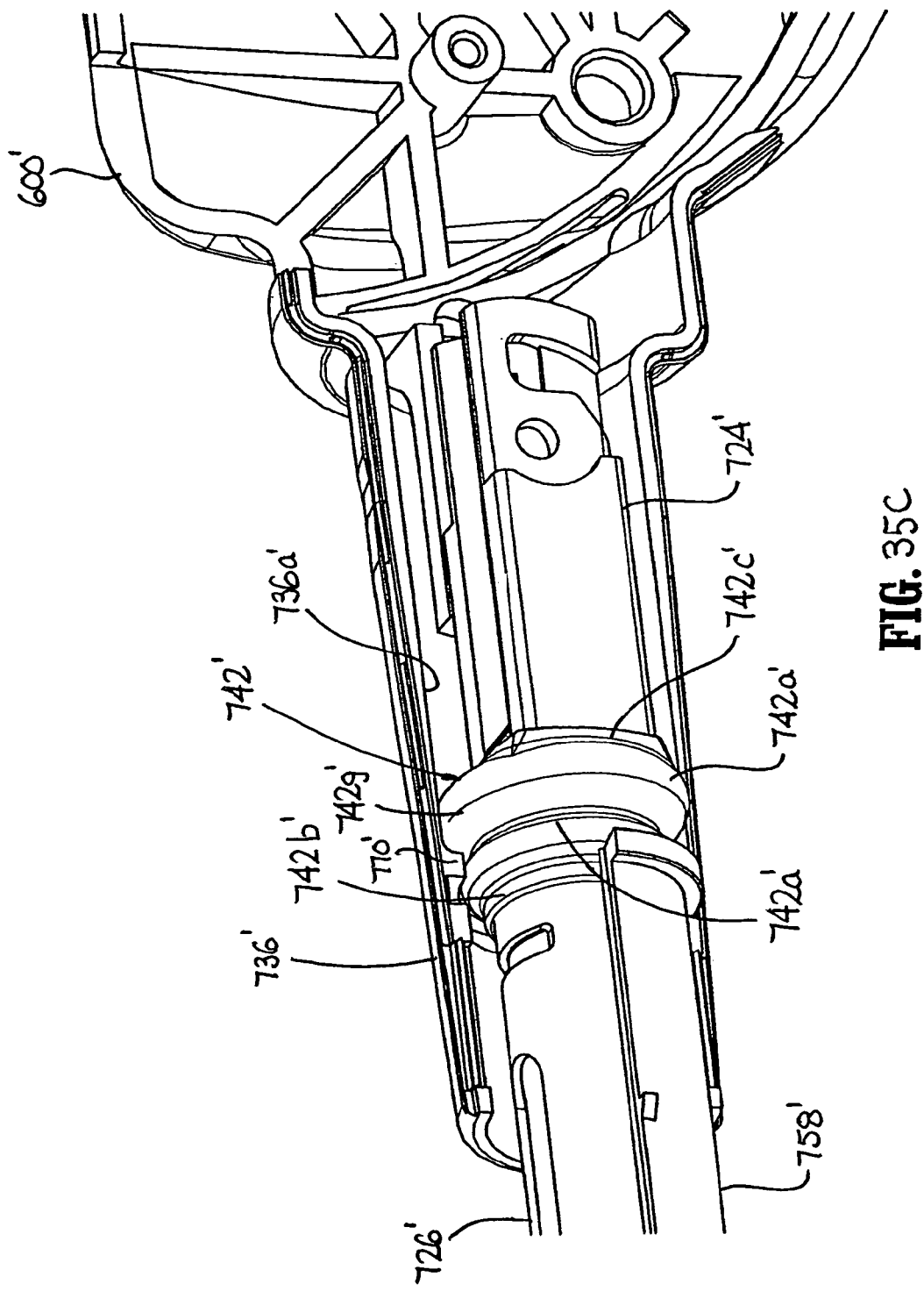
FIG. 35C is the side perspective shown in FIG. 35B with the clamp tube or member moved to its advanced position.
Figure 35D:
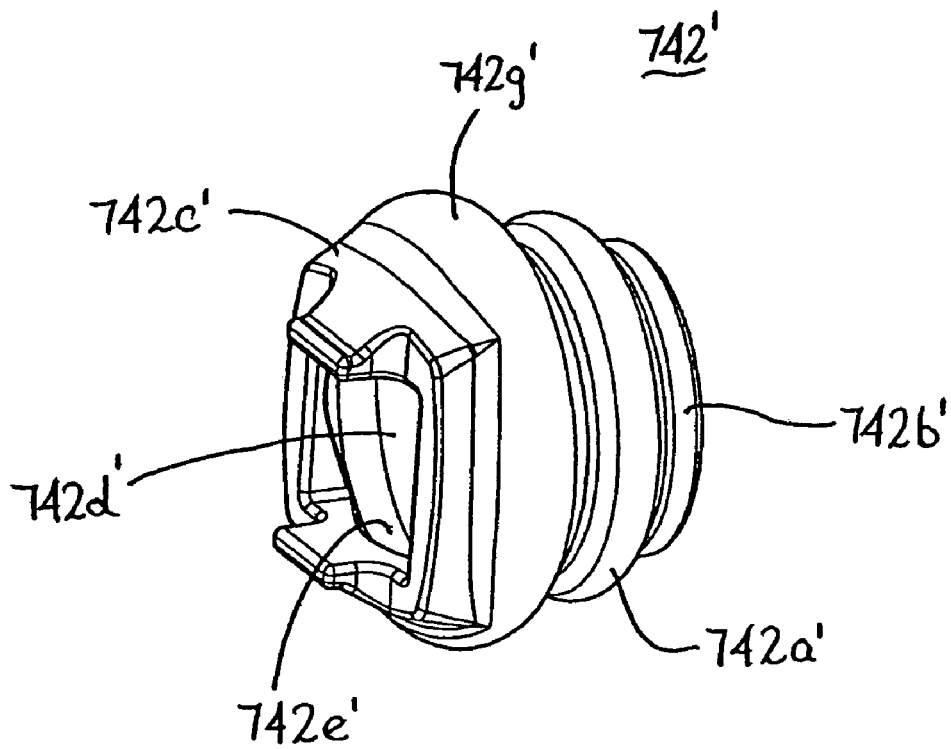
FIG. 35D is a side perspective view from the proximal end of the bellows seal.
Figure 35E:
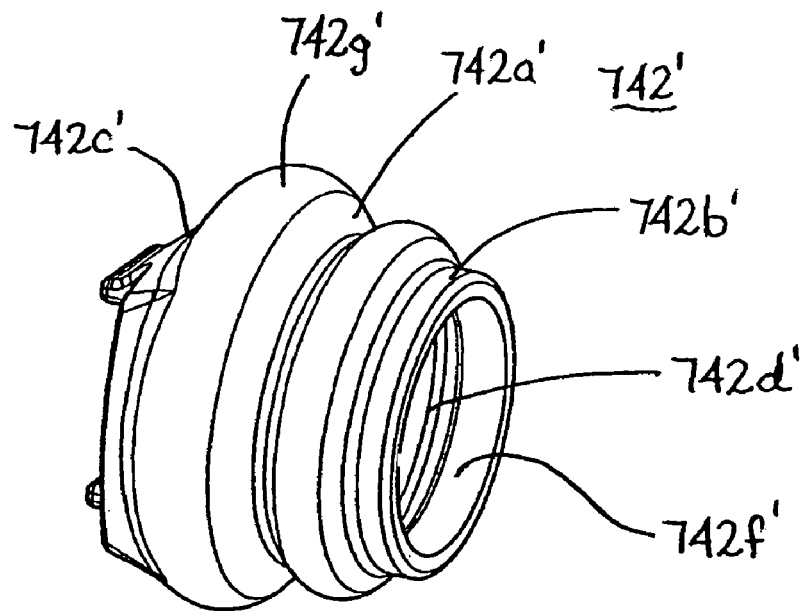
FIG. 35E is a side perspective view from the distal end of the bellows seal.
Figure 44:
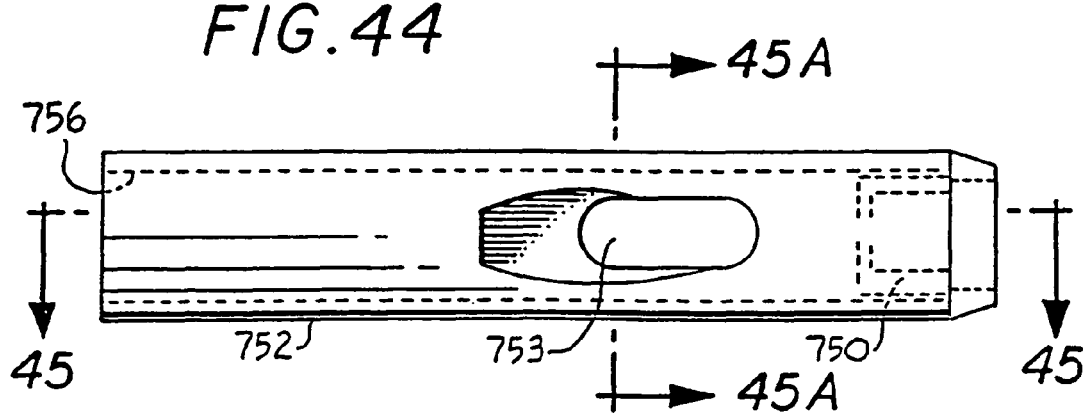
FIGS. 44 and 45 illustrate a top view and a side view in cross-section of the collar tube.
Figure 45:
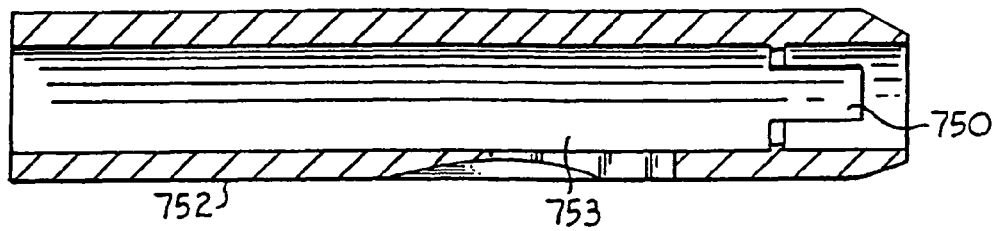
Figure 45A:
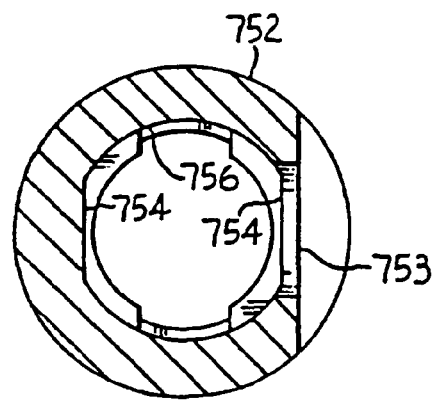
Figure 46:
FIGS. 46-49 illustrate top and side cross-sectional views of the upper and lower half of the cover tube.
Figure 47:
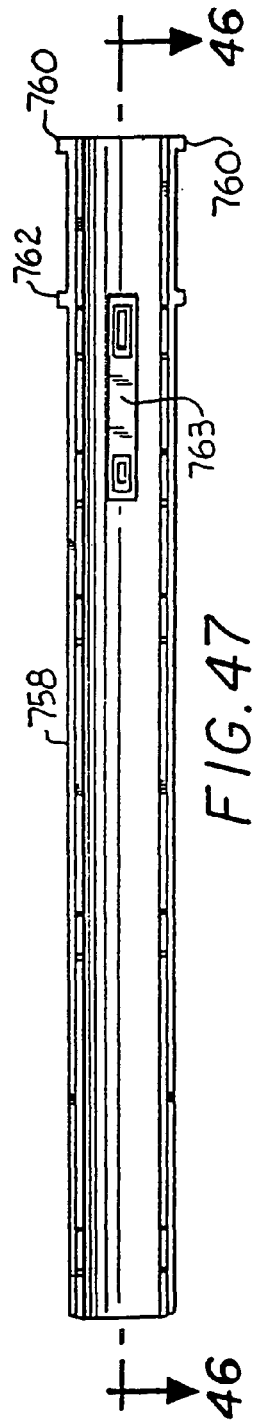
Figure 48:
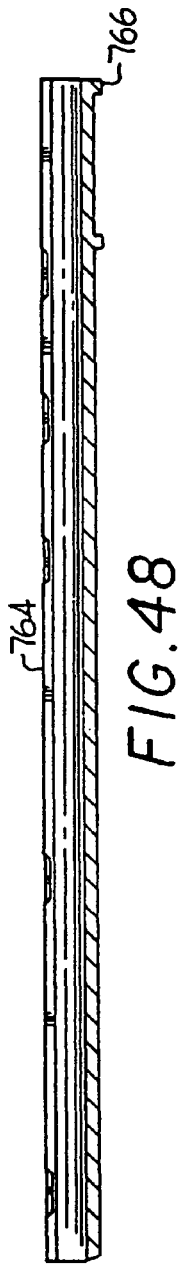
Figure 49:
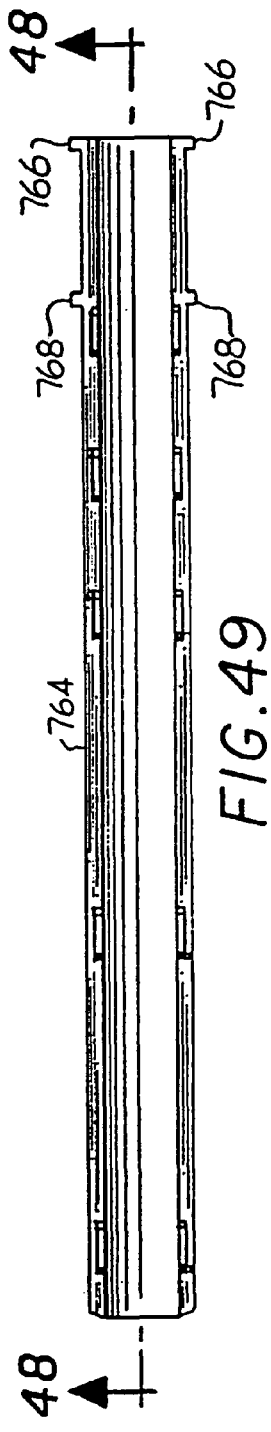

The driving surface formed by the pitch of pinion gear 674 engages arcuate rack 634 such that reciprocal motion of gear handle assembly 622 serves to rotate the pinion spur gear assembly in both clockwise and counterclockwise directions. The driving surface formed by the pitch of spur gear 676 engages a horizontal longitudinal rack 682 formed in the underside of rack rod 684 (FIGS. 38-40). Rotation of spur gear 676 translates through the horizontal longitudinal rack 682, to longitudinal reciprocal motion of the rack rod 684.

Figure 35:
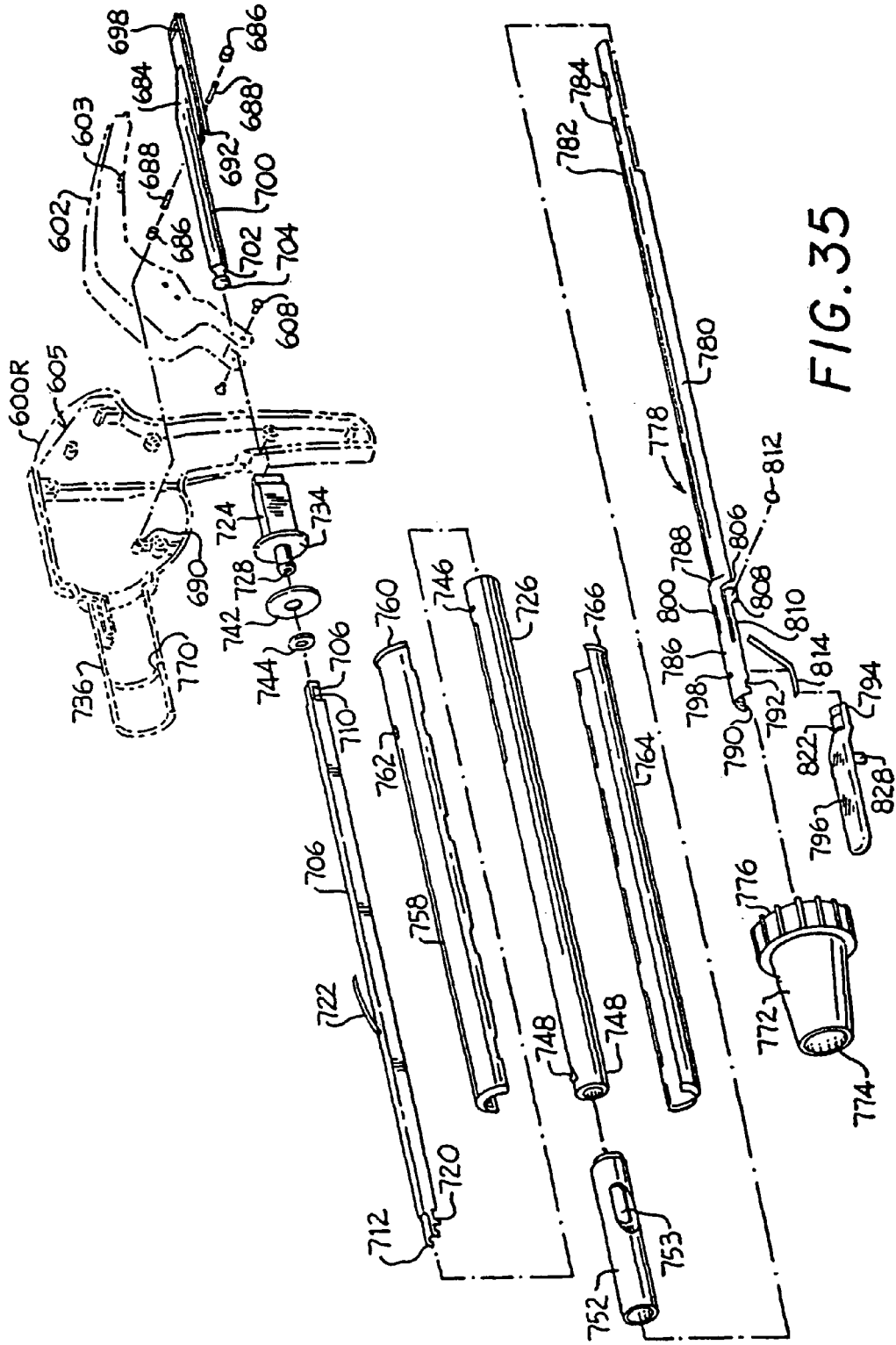

Referring now to FIG. 35 there is shown, in exploded view, the tube assembly 686 of the stapler apparatus in accordance with this second alternative embodiment of the present invention. At a proximal end, rack rod 684 is longitudinally slidable within frame 600 atop spur gear 676. Rollers 686, rotatable fixed in frame portions 600L and 600R by pins 688 engaged in holes 690, abut longitudinal shoulders 692 of the rack rod 682 and serve to prevent the rack rod 682 from disengaging from spur gear 676. Further vertical support for the rack rod is provided by interlock spring 694 (FIG. 34). Interlock spring 694 is formed in a substantially inverted T-shape and mounted transversely in frame 600 with the left and right branches of the I1T11 fixed into corresponding slots 696 of body portions 600L and 600R. The stalk of the "T" arcs forward to slidably engage a proximal end of horizontal longitudinal rack 682 and maintain a vertical force thereon.

Further, interlock spring 694 serves to assist the unique interlock feature between the gear handle assembly 622 and the clamp handle 602. Referring collectively to FIGS. 34 and 35, when clamp handle 602 is extended in the open position, the link pin assembly 612 is pivoted such that a distal end of links 612a and 612b abut the upper proximal surface of rack rod 684 proximate to projection 698. In this position, the link pin assembly 612 abutting projection 698 prevents distal longitudinal motion of the rack rod 684. By providing a vertical force proximate the underside of projection 698, interlock spring 694 prevents the rack rod 684 from pivoting downward to disengage the link pin assembly 612. Similarly, when the clamp handle is closed, link pin assembly 612 pivots about aperture 607 raising the distal ends of links 612a and 612b above projection 698. Thus it is apparent that the gear handle assembly 622 cannot be activated, accidentally or intentionally, when the clamp handle 602 is not closed.

Turning to FIGS. 35 and 38, rack rod 684 is provided with a longitudinal cylindrical shaft 700 having an axially mounted protruding stem 702 bearing a push plug 704. Push plug 704 has a chamfered distal tip and is configured and dimensioned to be received between the proximal fingers 706 on channel 708 (FIG. 50-53).

Channel 708 is an elongated piece having a substantially inverted U-shaped cross-section and which is slidably mounted for reciprocal longitudinal motion. As mentioned above, channel 708 has fingers 706 at a proximal end thereof to receive stem 702. Distal to the fingers 706 is a pair of transverse slots 710 dimensioned and configured to receive push plug 704. At a distal end of channel 708 there is provided fork 712 defining a slot 714 therebetween. Fork 712 has a pair of opposed ramping surfaces 716 and 718 respectively, the purposes of which will be described in greater detail below. Proximal to fork 712 is abutting structure 720 which structure extends below the lowermost dimension of fork 712. Biasing spring 722 is positioned on the upper surface of channel 708 and may be integrally stamped from the channel structure. This spring 722 imparts a downward force on the channel 708 to help maintain its horizontal configuration and to assist in engagement and disengagement of the channel 708 with cam bar adapter 846.

Figure 35A:
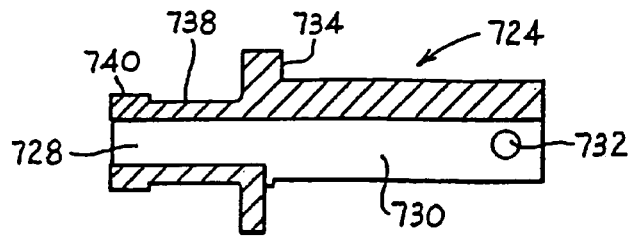

A clamp member or tube 724 is provided to interconnect the clamp handle 602 and an extension tube 726. Referring to FIGS. 35 and 35A, clamp tube 724 has a longitudinal bore 728 communicating with a chamber 730. Transverse aperture 732 is formed in a proximal end of the clamp tube 724 and pivotally connects the fork portion 604 of clamping handle 602 by means of pins 608. Push plug 704 of rack rod 684 passes into the proximal end of chamber 730 and out of the distal end of bore 728 such that fingers 706 and slots 710 of channel 708 engage push plug 704 distal to the clamp tube 724.

A flange 734 is formed circumferentially around the periphery of clamp tube 724 and is dimensioned to slidably fit within the area defined by the walls of the tubular portion 736 of frame portions 600L and 600R. Distal to flange 734 of clamp tube 724, a cylindrical section 738 is formed with a locking flange 740 on a distal end thereof. An outer gas seal 742 is positioned around cylindrical section 738 and adhered to the distal vertical face of flange 734. An inner gas seal 744 is positioned distal to outer gas seal 742 in sealing contact with shaft 700 of rack rod 684 and adhered to the distal vertical face of locking flange 740. Both inner and outer gas seals are fabricated of a resilient substantially gas impermeable foam material such as, for example, a closed cell polyethylene foam like Volara, by Voltek. Other materials of construction are encompassed by the present invention and are within the knowledge of one skilled in the art. Outer seal 742 is maintained in sealing relation with respect to frame 600 by dimensioning the circumference of the outer seal 742 with the inner circumference of the tubular portion 736 of frame 600. In this configuration, clamping tube 724 may move reciprocally longitudinally when driven by the clamp handle 602 while maintaining a substantially sealing relationship between the outer circumference of cylindrical section 738, the inner circumference of outer seal 742, the outer circumference of the outer seal 742 and the inner circumference of the tubular portion 736 of frame 600. Similarly, inner gas seal 744 maintains a substantially sealing relationship between the outer circumference of shaft 700, inner circumference of inner seal 744, the distal vertical surface of locking flange 740 and the proximate vertical surface of inner seal 744.

FIGS. 35B-E illustrate an alternate embodiment of the presently disclosed surgical apparatus wherein outer seal 742 (FIG. 35) has been replaced by a bellows seal 742'. Bellows seal 742' (FIGS. 35D-E) is constructed from a flexible material such as rubber and includes a body 742a' having a distal end 742b' and a proximal end 742c'. Body 742a' defines a throughbore 742d' having a substantially rectangular proximal opening 742e' and a substantially cylindrical distal opening 742f'. Seal 742' is positioned about clamp tube 724' such that a proximal end 742c' of seal 742' engages and seals against clamp tube 724'. Clamp tube 724' extends through proximal opening 742e' of seal 742' to a position to engage clamp handle 602 (FIG. 33) in the manner discussed above. Distal end 742b' is positioned to sealingly engage an outer surface of extension tube 726'. Bellow seal 742' further includes a bellows portion 742g' which is dimensioned to maintain contact, i.e., a slight interference condition, with an internal wall 736a' of tubular portion 736' of frame 600'.

Bellows seal 742' provides a radial seal with tubular portion 736'. As clamp tube 724' is moved from a retracted position (FIG. 35B) to an advanced position (FIG. 35C) within frame 600', distal end 742b' of bellows seal 742' is compressed against a proximal portion of a flange 770' within frame 600'. Compression of seal 742' causes seal 742' to expand outwardly to increase the capacity of the seal. In alternative embodiments, the bellows portion 742g' may be arranged to move from a collapsed condition that does not contact the wall 736a', to an expanded condition in contact with, and providing a seal with wall 736a', flange 770', or some other surface.

Figure 36:
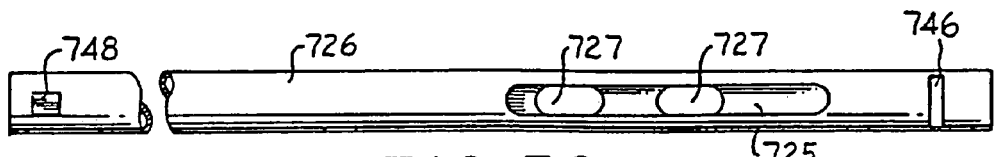
FIGS. 36 and 37 illustrate side and top views of the extension tube.
Figure 37:
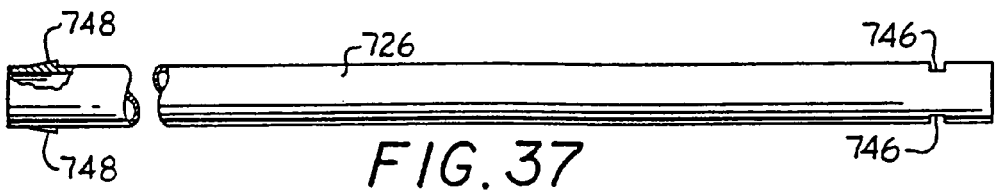

Referring now to FIGS. 35-37 and specifically to FIGS. 36 and 37 there is shown extension tube 726 preferably formed as a single tubular structure so as to provide support to the instrument. A pair of transverse slots 746 are formed in a proximal end of extension tube 726 at a point such that when the extension tube 726 is positioned over cylindrical section 738 of clamp tube 724, transverse slots 746 are positioned in the area between the flange 734 and the locking flange 740. In this position, the proximal end of the extension tube up to the transverse slot is crimped effectively locking the extension tube 726 onto the clamp tube 724 while allowing it to freely rotate. An elongated longitudinal aperture 725 is formed in the upper surface of extension tube 726 at a point near the proximal end thereof. A pair of smaller apertures 727 are provided radially apart from aperture 725 to provide access thereto.

At the distal end of extension tube 726 there is provided a pair of projections 748 which slope outward from the distal end. These projections 748 engage and interlock with slots 750 formed in the internal proximal surface of collar tube 752 (see FIGS. 44 and 45). At its distal end, collar tube 752 is formed with a cross-section having one set of opposed substantially parallel walls 754 and a top arcuate camming surface 756. The arcuate camming surface is described in greater detail below. One side of collar tube 752 is provided with a longitudinal slot 753 for receiving cartridge releasing structure.

FIGS. 46-49 show the upper and lower cover tube structure which surrounds extension tube 726. Upper cover tube half 758 is substantially semi-circular in cross-section having a circumferential flange portion 760 on a proximal end thereof. Set in from the proximal end is a projection 762. Extending from the internal surface is a projecting boss structure 763 which interfits within longitudinal aperture 725 in extension tube 726. This aperture is dimensioned to allow for unrestricted longitudinal motion of extension tube 726.

Lower cover tube half 764 is substantially a mirror image of upper cover tube 758 without the boss structure 763 and includes a flange portion 766 on a proximal end and projection 768 set in from the end. The distal ends of both halfs are chamfered.

Upper and lower cover tube halfs 758 and 764 are joined together, preferably by means of adhesives or ultrasonic welding. Other joining methods are also envisaged and are within the skill of those in the art. When joined, the complete circumferential flange made up of upper and lower portions, 760 and 766 respectively, fit into a circumferential groove 770 formed in the inner surface of the tubular portion 736 of frame 600. Once in position within groove 770, the cover tube is free to rotate about the longitudinal axis relative to the frame 600. The cover tube, however, cannot move longitudinally relative to the body 600.

Referring again to FIG. 35, rotation knob 772 is dimensioned to slide over the cover tube structure as shown and interlock with projections 762 and 768 at a point distal to the tubular portion 736 of frame 600. The rotation knob 772 is in the form of an abbreviated frustoconical structure having a bore 774 therethrough dimensioned to receive the cover tube structure. At a proximal end thereof, knurling 776 may be provided to facilitate rotation. Because of the interlocking structure of the tubes, rotation of the rotation knob 772 effects rotation of the tube assembly.

A further element of the tube assembly is support 778 (FIGS. 41-43). Support 778 has a central channel portion 780 dimensioned to slidably receive channel 708 for longitudinal reciprocal motion therein. A mounting portion 782 is formed at a proximal end and is provided with attaching slots 784 which are fixed to projecting boss structure 763 of the upper cover tube half 758. Access to the boss structure 763 to effect secure attachment of support 778 is provided through apertures 727 of the extension tube 726. This configuration allows the support 778 to rotate freely with the cover tube while maintaining a fixed longitudinal position with respect to extension tube 726.

At the distal end of support 778 there is provided a mounting and release structure as will be described below. Semi-circular portion 786 is tapered at 788 to attach to channel portion 780. Camming surfaces 790 are formed in the distal end of semi-circular portion 780. A transverse slot 792 is formed proximal to camming surfaces 790 for receiving projections 794 of anvil 796. A transverse crimp 798 is made in the upper surface of semi-circular portion 780 to form a transverse strap for receiving and pivotally holding leaf spring 714 of anvil 796.

Biasing spring 800 is also formed in the upper surface of semi-circular portion 780 and extends inwardly to maintain the channel 708 in the longitudinal horizontal plane as it passes through support 778.

An L-shaped slot 802 is formed in the side wall of semi-circular portion 780 as shown in FIG. 43. This slot 802 forms release catch 804, comprising a rectangular engaging structure 806 having a ramped forward end 808 and a flexible attaching arm 810 which allows engaging structure 806 to be biased inwardly. Release button 812 is positioned on engaging structure 806 and assists in biasing the flexible attaching arm 810 a predetermined distance inward of the semi-circular portion 780. When assembled, semi-circular portion 780 slidably fits within collar tube 752 with release button 812 being accessible through longitudinal slot 753.

Figure 54:
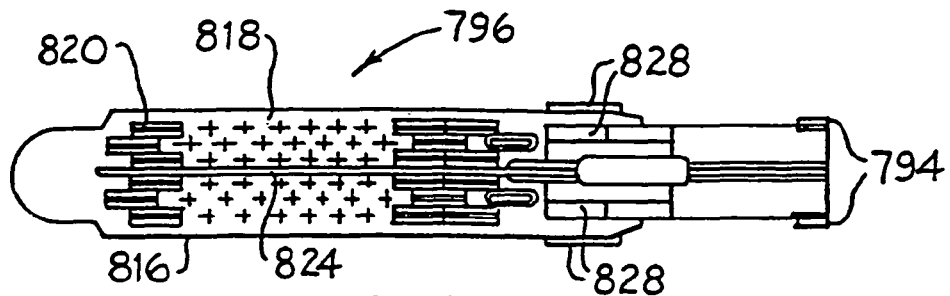
FIGS. 54-56 illustrate top, bottom and side views of the anvil.
Figure 55:
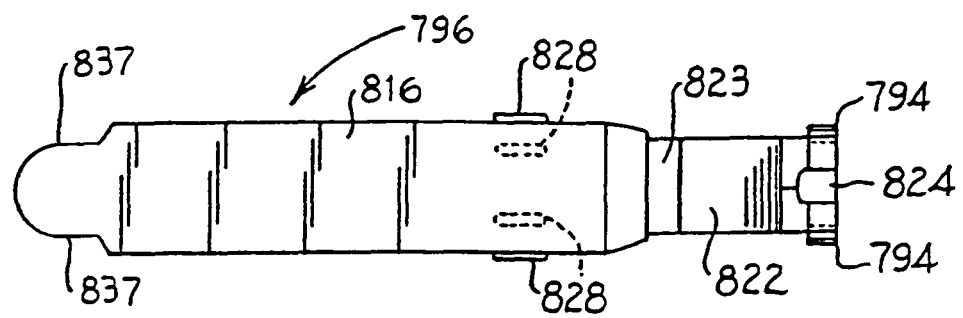
Figure 56:
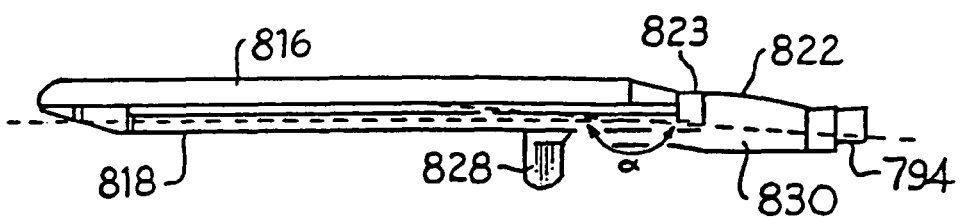

Referring to FIGS. 54-56, anvil 796 is an elongated piece which is pivotally mounted in relation to support 778 by means of leaf spring 814. At its distal end, anvil 796 has an anvil plate 816 with a tissue contacting surface 818 having staple forming depressions 820 (See FIG. 54). At its proximal end, anvil 796 is provided with an upper camming surface 822 and locking surface 823 which surfaces are engagable with corresponding top arcuate camming surface 756. Transverse projections 794 are formed at the proximal end of anvil 796 and provide a pivot point about which the anvil 796 may be rotated between an open and closed position by the interaction of camming surface 822, locking surface 823 and top arcuate camming surface 756 of collar tube 752. Preferably, the radius of curvature of the top arcuate camming surface 756 is shorter than the radius of curvature of camming surface 822 and equal to the radius of curvature of locking surface 823. This configuration prevents flexing of the camming surface 756 of collar tube 752 and lateral movement of the anvil as it is being cammed closed.

Leaf spring 814 is fixed in slot 824 at the proximal end of anvil 796. The angular orientation of the leaf spring 814 is such that, upon insertion of the anvil 796 into the semi-circular portion 786 of support 778, leaf spring 814 passes through the strap formed by transverse crimp 798 and maintains anvil 796 oriented in the open position with projections 794 disposed in transverse slots 792 in the support 778.

Anvil plate 816 also has a longitudinal center groove 824 to permit passage of a knife 826. ~nvil 796 provides one of the jaws of the instrument for clamping and securing the body tissue to be fastened. Preferably, anvil 796 is provided with one or more tissue stops 828 to help prevent over-insertion of tissue into the jaws. In a particularly advantageous embodiment shown in FIGS. 55-56 the anvil is provided with four tissue stops, two of which are disposed on the outer vertical surface of anvil plate 816 with the remaining two internally transversely positioned. This unique configuration allows for more accurate longitudinal alignment of the jaws and prevents twisting of the anvil upon closure. Anvil 796 is further provided with parallel aligning surfaces 830 positioned below camming surface 822. These aligning surfaces are dimensioned to fit within projections 834 on cartridge housing 832 upon closure of the anvil 796. The engagement of the aligning surfaces 822 and the corresponding projections 834 of cartridge housing 832 serves to more accurately and securely align anvil 796 and cartridge housing 832 upon closure. Further visual confirmation of alignment is facilitated by a pair of parallel longitudinal indentations 837 formed in the distal end of anvil 796. These indentations 837 allow the surgeon to view the closed structure of the anvil 796 and cartridge assembly 836 to confirm accurate longitudinal alignment thereof.

Further, as shown in FIG. 56, the horizontal plane formed by tissue contacting surface 818 intersects the horizontal plane formed by the camming portion of the proximal end of anvil 796 at an obtuse angle I1$a$/1. This angular orientation pre-cambers the anvil 796 and balances the closure force applied by the anvil 796 to the captured tissue.

As discussed above, a wide variety of staples and fasteners are contemplated for use with the present apparatus. In a preferred embodiment for use with titanium fasteners, it has been found that forming of the fasteners in the staple forming depressions 820 is facilitated by applying a hard, relatively smooth surface on the staple forming portion of the anvil 796. The preferred method of application of this surface is by electroless plating, with the surface being formed of a metallic alloy such as, for example, nickel, gold, silver, titanium nitride or chromium. Where nickel is used, the applied surface is preferably in the range of 100 p-2000 p in thickness with an optimum thickness of between 200 p-500 p. Ranges for other alloys may vary depending upon their inherent characteristics.

Where nickel is to be applied, the preferred method is an electroless plating method including the steps of: eletrocleaning the anvil in a cyanide-containing cleaner, reversing polarity at predetermined intervals, preferably about every 10-15 seconds, at a current of about 50 amps/ft2; rinsing thoroughly; rinsing in a solution containing a strong acid, preferably 20% HCL, dipping several times; immersing the anvil in a NiCL strike tank for plating, preferably for two to four minutes at a current of about 50 amps/ft2; rinsing; and immersing the anvil in an electroless Ni bath, preferably Enthone 418 or 431, for a time sufficient to achieve the desired plating thickness. For example, at a deposition rate of 0.0005 in/hr, a time of between 30 to 40 minutes would be required to achieve a thickness of about 300 p 2 50 p. Other coating procedures are also contemplated including vapor deposition, etc. and are encompassed by the present invention.

Turning now to FIGS. 57-64, there is shown a unique replaceable cartridge assembly 836 in accordance with the present invention. The cartridge assembly 836 includes: a cartridge housing 832; a cartridge 838 having a plurality of pushers 840 and staples 842 disposed in longitudinal arrangement therein; and a plurality of cam bars 844 removably disposed in a cam bar adapter 846 and a knife 826 mounted in the cam bar adapter 846.

Figure 62:
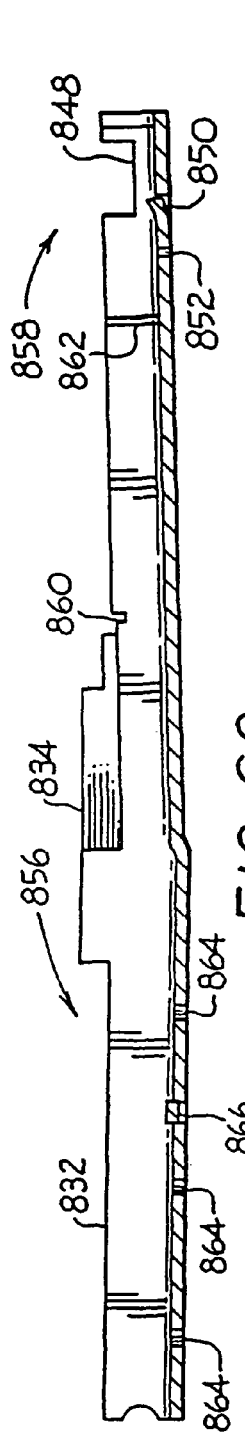
FIGS. 62-64 illustrate side and top views of the cartridge housing.
Figure 63:
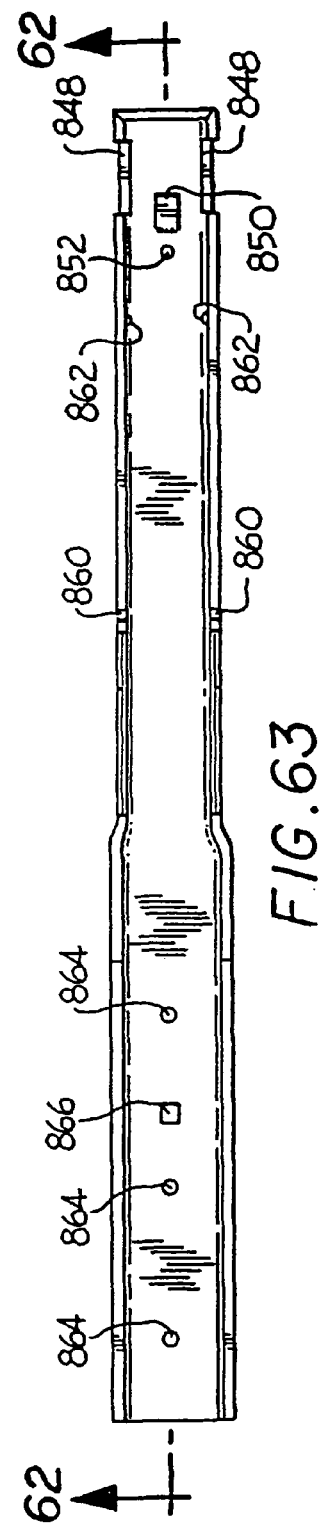
Figure 64:
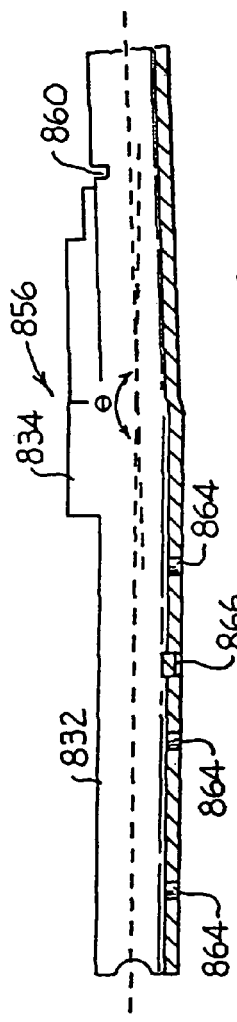

Referring specifically to FIGS. 62-64, the proximal end of cartridge housing 832 comprises a substantially elongate channel of semi-circular cross-section having a forward and rearward portion 856 and 858 respectively. A transverse locking slot 848 is formed in rearward portion 858 and serves to engage and retain engaging structure 806 of support 778. Upon insertion into collar tube 752, the ramped forward end 808 of engaging structure 806 is biased inward by the rearward portion 858 of cartridge housing 832 until the engaging structure 806 is totally within and retained by locking slot 848.

Rearward projection 850 is formed in the base of cartridge housing 832. The function of this projection 850 will be described in greater detail below. Forward of the projection 850 is a bore 852 which receives shear pin 854 formed on cam bar adapter 846. A pair of crimps 862 is provided in opposing sidewalls of the rearward portion of the proximal end of the cartridge housing. These crimps 862 provide a friction fit with cam bar adapter 846.

The forward portion 856 of the proximal end of cartridge housing 832 has projections 834 which, upon closure of the cartridge assembly 836 and anvil 796, contact and align on anvil aligning surfaces 830 as described above. A transverse slot 860 is positioned rearward of projections 834 as shown in FIGS. 62 and 64. This slot serves to receive and retain projections 794 of anvil 796 upon closure of the anvil upon the cartridge assembly 836.

The distal end of the cartridge housing 832 comprises a channel structure of substantially rectangular cross-section. This distal end constitutes the cartridge receiving portion and is dimensioned to receive cartridge 838 therein. Bores 864 and projection 866 serve to engage pins and bores respective in the cartridge 838 so as to align and retain the cartridge 838 within the cartridge receiving portion of the cartridge housing 832.

Referring to FIG. 64, the cartridge receiving portion in the distal end of cartridge housing 832 and the proximal end of cartridge housing 832 are joined at an obtuse angle 0 defined by the intersection of the horizontal planes of both the proximal and distal ends of the cartridge housing 832. This angular orientation serves to pre-camber the cartridge assembly and facilitates accurate closure and alignment of the jaw elements as well as more secure retention of subject tissue.

The cartridge 838 is substantially the same as the cartridge 137 described above and includes longitudinal groove structure 868 for receiving and guiding knife 826 and a plurality of pushers 840 abutting staples 842. The staples 842 are advantageously arranged in six longitudinal rows with three rows positioned on either side of groove structure 868.

Figure 57:
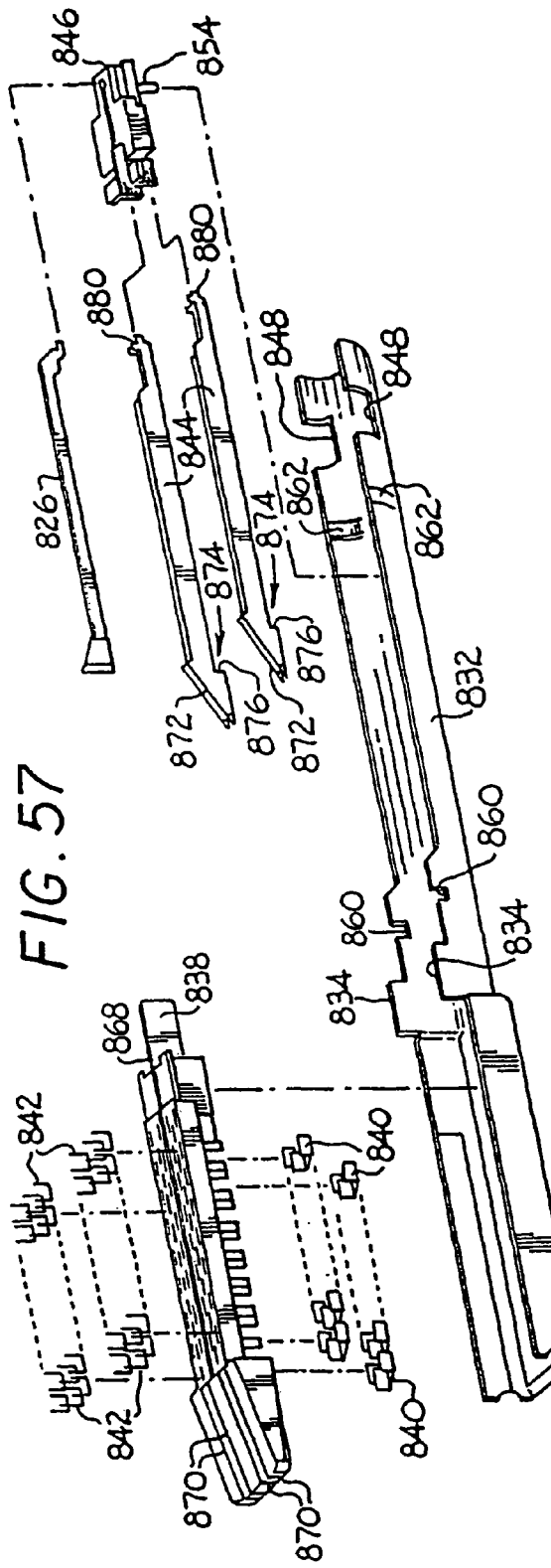
FIGS. 57 and 57A illustrate an exploded perspective and assembled perspective views of the cartridge assembly.
Figure 57A:
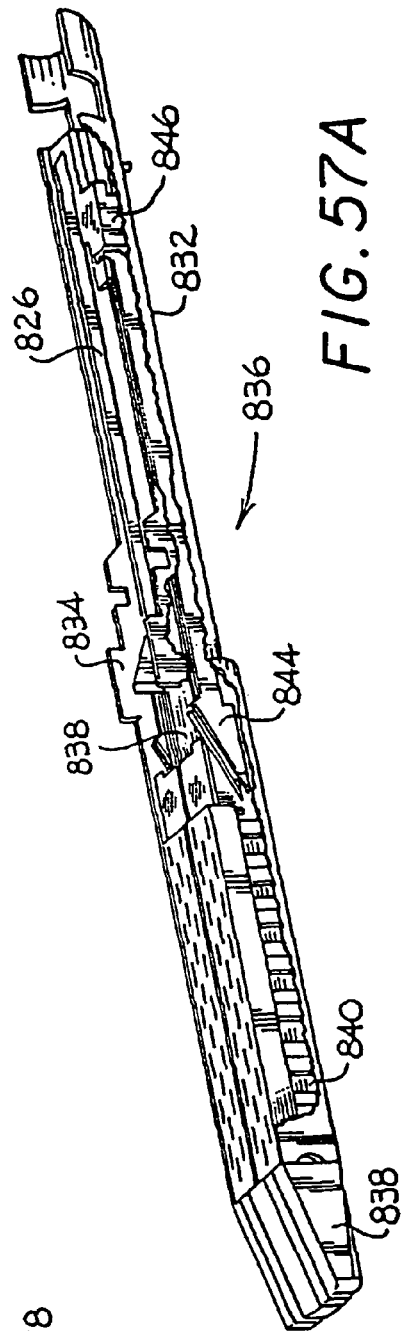
Figure 58:
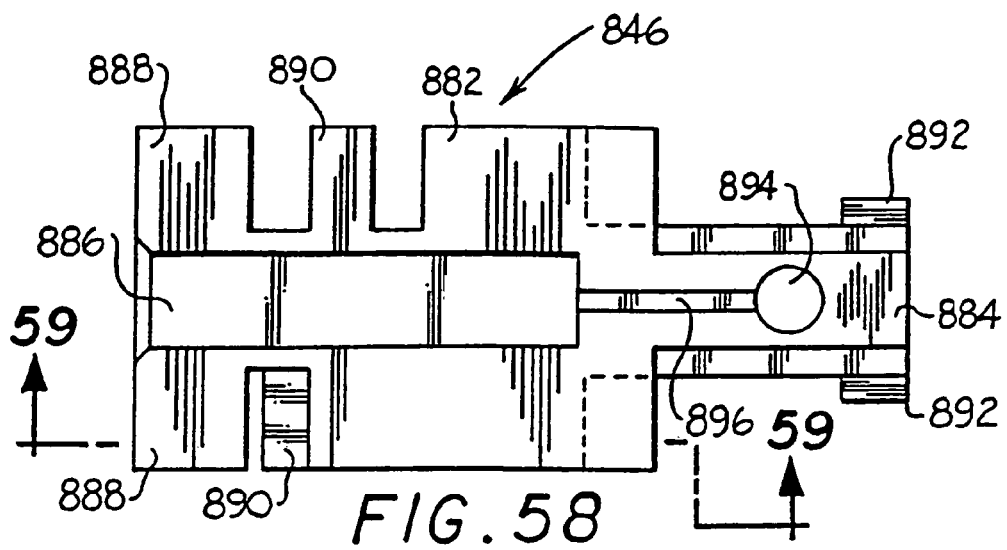
FIGS. 58-61 illustrate top, side and frontal views of the cam bar adapter.
Figure 59:
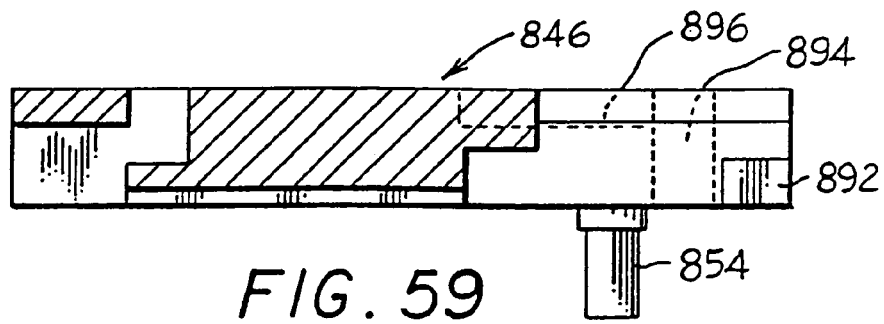
Figure 60:
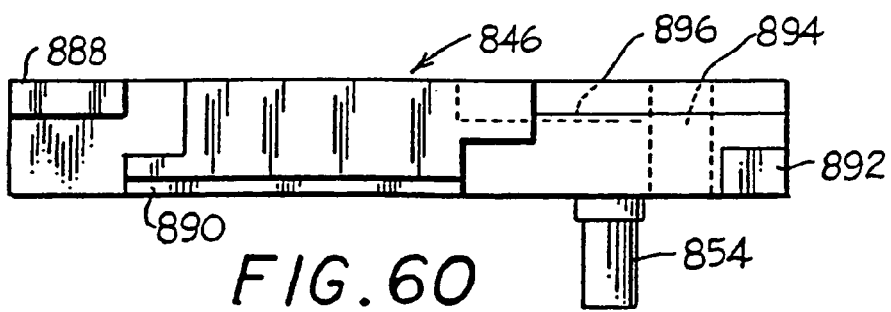
Figure 61:
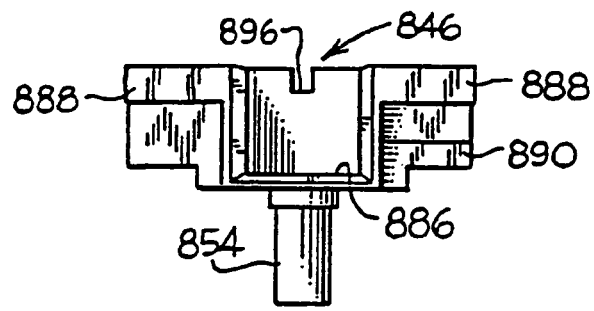

Two pairs of longitudinal slots 870 formed in the cartridge housing are adapted to receive a pair of double cam bars 844 therein. Each pair of cam bars serving to drive three corresponding longitudinal rows of staples. Further, the two pairs of longitudinal slots 870 extend to the end of cartridge 838 as shown in FIGS. 57 and 57A.

Cam bars 844 are provided with a cam surface 872 in an upper distal end thereof and an overhanging ledge 874 with vertical surface 876 in a lower distal end. This overhanging ledge 874 is dimensioned to extend into the longitudinal slots 870 to a point wherein the vertical surface 876 of the overhanging ledge 874 drops down and abuts the forward edge 878 of the cartridge retaining portion of the cartridge housing when the cam bars 844 move to their distal fired position. At their proximal end, cam bars 844 are provided with hook structure 880 for releasably engaging cam bar adapter 846.

Referring now to FIGS. 58-61 there is shown multiple views of the unique cam bar adapter 846 in accordance with one embodiment of the present invention. The cam bar adapter 846 comprises a forward section 882 and a rearward section 884. The forward section 882 is substantially rectangular in shape and has a central longitudinal groove 886 formed therein and dimensioned to receive the longitudinal groove structure 868 therein when the cam bar adapter is urged to its forwardmost position. Flanges 888 and shelves 890 serve to removably retain the proximal end of cam bars 844.

The rearward section 884 is rectangular in shape with projections 892 formed in the proximal end thereof. The rearward section is dimensioned to be receivable within slot 714 of fork 712 in channel 708. The projections 892 are dimensioned to engage ramping surface 716 to allow the fork 712 to ride up and over the projections 892 when the fork 712 is moved in the distal direction.

Vertical bore 894 and longitudinal groove 896 are formed in the rearward section 884 and serve to retain and hold shank 898 of knife 826. Shear pin 854 is integrally formed with cam bar adapter 845 on a bottom surface thereof and, in the prefiring position, is aligned with and receivable into bore 852. Also, in this prefiring position, the rearward section 884 of the cam bar adapter 846 is disposed over rearward projection 850 to effectively shield engagement of abutting structure 720 with projection 850.

It is envisioned that the surgical apparatus shown in FIGS. 33-64 can be dimensioned to drive longitudinal rows of staples having a variety of lengths, e.g., 15 mm, 30 mm, 45 mm, 60 mm, etc. For example, to provide a shorter or longer actuation stroke of channel 708, the diameter of spur gear 676 and rack 683 can be selectively adjusted to effect the desired stroke length.

FIGS. 65-69 illustrate an embodiment of the cartridge assembly and anvil member of the present invention which permits tubular structures within the body to be ligated and/or divided. Both the cartridge assembly and the anvil member of this embodiment are clamped and actuated by substantially the same frame and tubular structure as that described above with respect to the second alternative embodiment and share substantially the same structure as the cartridge and anvil members shown in other embodiments herein (see FIGS. 12-14, 54-56 and 57) with the exception of structure located on the distal ends of both the anvil member and the cartridge assembly.

Figure 65:
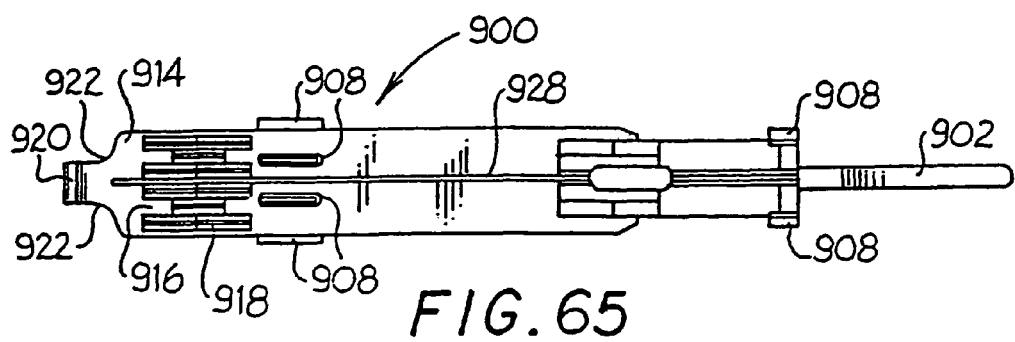
FIGS. 65-67 illustrate top, bottom and side views of an anvil member in accordance with an alternate embodiment of the present invention for use in ligating tubular tissue.
Figure 66:
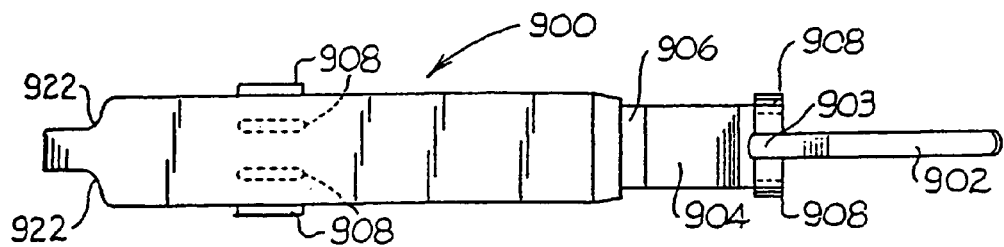
Figure 67:
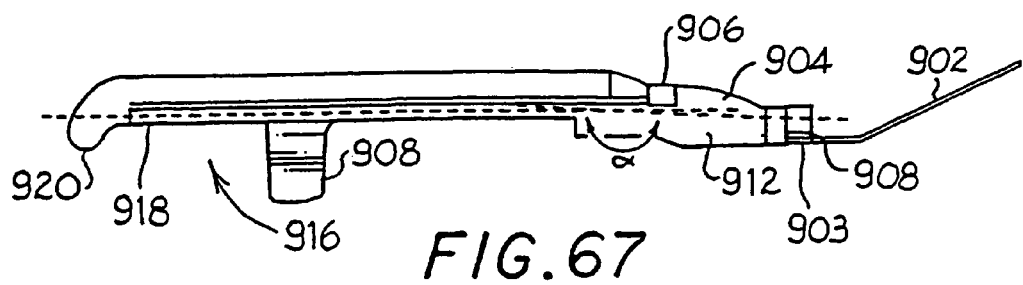

Referring to FIGS. 65-67, anvil 900 is an elongated piece which is pivotally mounted in relation to support 778 by means of leaf spring 902. This leaf spring 902 is fixed in slot 903 at the proximal end of anvil 900 and, when assembled, is retained in the strap formed by transverse crimp 798 in support 778. At its proximal end, anvil 900 is provided with an upper camming surface 904 and a locking surface 906 which surfaces are engagable with corresponding top arcuate camming surface 756 of collar tube 752. Transverse projections 908 are formed at the proximal end of anvil 900 and provide a pivot point about which the anvil 900 may be rotated between an open and closed position by the interaction of camming surface 904, locking surface 906 and top arcuate camming surface 756 of collar tube 752. As in embodiments previously described, the radius of curvature of the top arcuate camming surface 756 of collar tube 752 is shorter than the radius of curvature of camming surface 904 and equal to the radius of curvature of locking surface 906.

Anvil 900 also has tissue stops 908 to prevent overinsertion of tissue into the instrument. Anvil 900 has parallel aligning surfaces 912 positioned below camming surface 904. These aligning surfaces are dimensioned to fit within projections 834 on cartridge housing 832 upon closure of anvil 900.

At its distal end, anvil 900 has an anvil plate 914 with an abbreviated tissue contacting surface 916 having staple forming depressions 918 and an arcuate tissue capturing portion 920. This tissue capturing portion is advantageously designed in a blunted hook configuration as shown in FIG. 67 in order to assist in the capture and proximation of tubular tissue such as, for example, blood vessels, ducts, etc. without unnecessary damage to surrounding tissue. In a particularly preferred embodiment, this arcuate tissue capturing portion is provided with longitudinal tapered surfaces 922. These surfaces fit within mating surfaces 924 in the cartridge assembly 910 and serve to provide the surgeon with a better field of view of the tissue ligation site. Upon closure, surfaces 922 and 924 also give visual confirmation of correct longitudinal alignment. Where captured tissue is to be ligated and divided, a knife 826 is provided and travels in longitudinal groove 928 formed in the anvil plate 914.

Figures 68, 69:
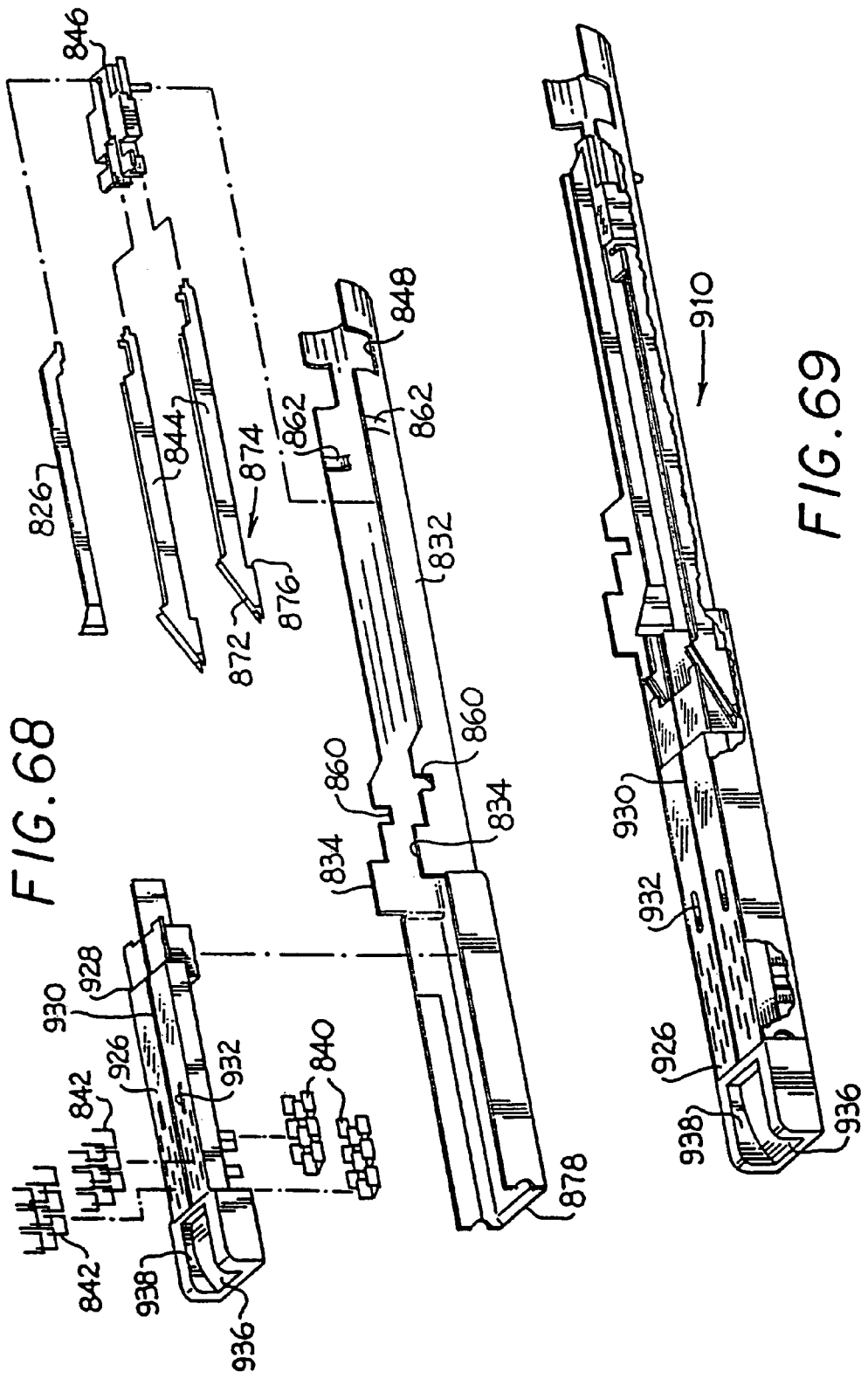
FIGS. 68-69 illustrate an exploded perspective and assembled perspective view of a cartridge assembly in accordance with an alternate embodiment of the present invention for use in ligating tubular tissue.
Figure 70:
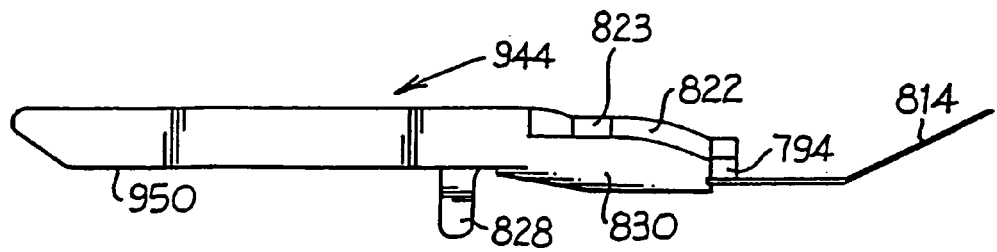
FIGS. 70 and 71 illustrate a side view of clamping jaws in accordance with an alternate embodiment of the jaw members of the present invention.
Figure 71:
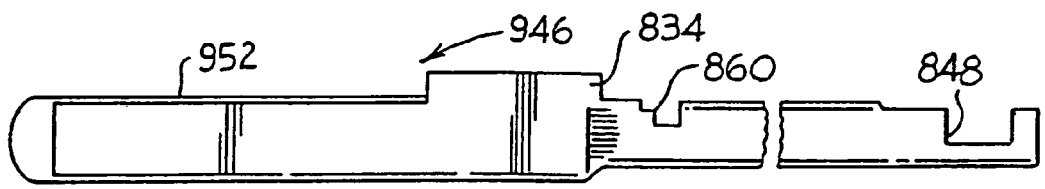
Figure 72:
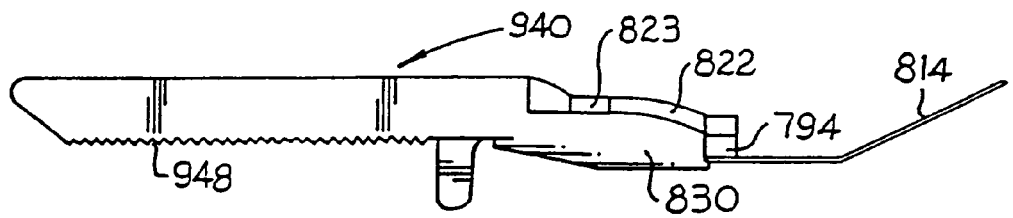
FIGS. 72 and 73 illustrate a side view of gripping jaws in accordance with an alternate embodiment of the jaw member.
Figure 73:
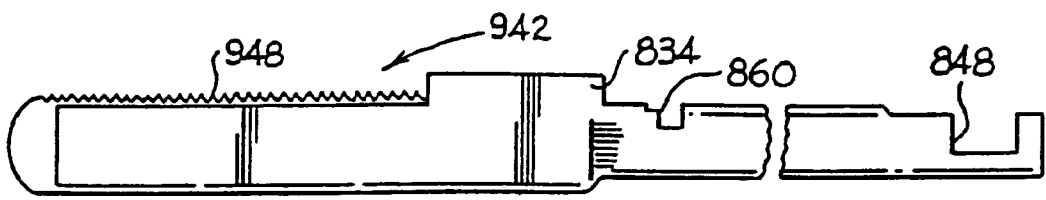

FIGS. 68 and 69 illustrate a cartridge assembly 910 in accordance with an embodiment of the present invention for use in grasping, ligating and/or dividing tubular tissue. The cartridge assembly 910 is substantially similar to the other cartridge assemblies described above and includes: a cartridge housing 832; a cartridge 928 having a plurality of pushers 840 and staples 842 disposed in longitudinal arrangement therein; a plurality of cam bars 844 removably disposed in a cam bar adapter 846 and, where dividing is to be effected, a knife 826 mounted to the cam bar adapter 846.

The proximal end of cartridge assembly 910 is substantially the same as that described above with respect to cartridge assembly 836 and is engagable with support 778 in substantially the same manner. Similarly, the distal end of cartridge assembly 910 utilizes the same channel structure of substantially rectangular cross-section.

Cartridge 928 differs somewhat from previous embodiments and includes a plurality of pushers 840 abutting staples 842 arranged in relatively abbreviated longitudinal rows in a tissue receiving surface 926 of cartridge 928. Where a knife 826 is to be used to divide captured, ligated tissue, longitudinal groove structure 930 is provided for receiving and guiding knife 826. In a preferred embodiment, the staples 842 are arranged in six longitudinal rows with three rows positioned on either side of groove structure 930. Bores 932 are provided in the upper surface of cartridge 928 to receive the innermost tissue stops 908.

For typical tubular structure such as blood vessels and ducts, the tissue receiving surface 926 is abbreviated and utilizes fewer staples 842 than previously discussed embodiments. Preferably, the tissue receiving surface 926 is dimensioned to provide sufficient staples to ligate the intended tubular tissue without excess staples being ejected at the site of the tissue ligation.

Two pairs of longitudinal slots 934 formed in cartridge 928 are adapted to receive a pair of double cam bars 844 therein. In this embodiment, each pair of cam bars serves to drive three corresponding longitudinal rows of staples.

The distal end of cartridge 928 has an anvil mating surface 924 formed therein to receive arcuate tissue capturing portion 920 of anvil 900 when the cartridge assembly and anvil are closed. This mating surface comprises an arcuate ramp 936, corresponding in shape to the arcuate tissue capturing portion 920 of the anvil 900, and tapered vertical side walls 938, corresponding to tapered surfaces 922 of anvil 900. These surfaces, 920, 936, 938 and 922 engage upon closure to accurately and positively capture tubular structure for ligating and/or dividing. The operation of cam bars 844 and knife 826 is substantially the same as that described above with respect to FIGS. 57-64.

Further alternative embodiments are contemplated in which all or part of the instrument would be disposable. Where the entire instrument constitutes a single use, disposable instrument, the endoscopic portion preferably would be integral with the frame and as much of the instrument as possible would be constructed of plastic. In other contemplated embodiments the cartridge, knife and possibly the anvil might be disposable, alone or as a unit. It is also contemplated, for example, that a replaceable cartridge assembly could be provided which includes the knife and possibly the cam bars.

It is also preferred in all embodiments to include a sealing member within the housing in order to effect an internal seal within the housing. Of course, such a sealing member, not here illustrated, must permit longitudinal movement of the clamping and firing elements.

Suitable materials for use in constructing the instrument in accordance with the invention include stainless steel, titanium, aluminum and plastic. Where disposability of all or part of the instrument is desired, plastic is the material of choice for economic reasons. Plastic is also preferred, where possible, in order to minimize the overall weight of the instrument. Of course, certain parts, such as the anvil, have performance requirements which dictate the material used. In the case of the anvil, the need for high strength and accurately shaped depressions to deform the staples typically requires use of a metal, such as stainless steel. Similarly, the knife requires a fine cutting edge and typically is also made from stainless steel. The staples used with the present invention may be non-absorbable plastic or metal or an absorbable synthetic material, such as a copolymer of polyglycolic acid. Of course, the foregoing identification of materials is exemplary only, and numerous variations, substitutions and changes in material will occur to those of ordinary skill in the art.

Operation of the Instrument

In use, the endoscopic portion of the instrument is inserted into the body, preferably through an endoscopic tube. It is further preferred that the endoscopic tube apparatus be capable of maintaining a sealed pneumoperitoneum, with the internal sealing member of the housing further maintaining this seal despite introduction of the instrument in accordance with the invention into the endoscopic tube. As a practical matter, the jaws of the instrument are closed for insertion into the endoscopic tube, either by pinching the anvil and cartridge prior to insertion or by closing the clamping mechanism prior to insertion.

After insertion into the endoscopic tube, the endoscopic portion may be rotated in order to appropriately orient the instrument at the stapling site. Rotation of the endoscopic portion relative to the body may be attained by rotating the instrument, as a whole, by rotating the endoscopic portion relative to the frame using finger wheel 123 (see FIG. 1) or sleeve 522 (see FIG. 17), or rotation knob 772 (see FIG. 33), or any combination thereof.

Referring additionally now to FIGS. 15A and 15B, with the instruments properly oriented so that the tissue to be fastened 201, 202 is disposed between the open jaws of the instrument, i-e., between the tissue contacting surfaces of anvil member 136, 336 and cartridge 137, 337, the jaws are closed to clamp the tissue. In the first embodiment, the surgeon presses down on toggle lever 104, thereby sliding collar 127 distally, via collar shaft 125, collar pivot wheel 115, collar pivot holder 112, and collar moving pivot 111. As collar 127 moves distally in the direction of arrow A from a first position where the camming edge 127B at the distal end of collar 127 is proximal to hinge 136C (FIG. 15A), to a second position where the camming surface 127B is distal to the hinge 136C (FIG. 15B), the camming edge 127B contacts the upper surface of the anvil arms 136B, thereby forcing anvil member 136 to rotate in the direction of arrow B until the fastener forming surface 136E is brought into close cooperative alignment with the cartridge assembly, i.e., the slots 137A are aligned with staple forming depressions 136D. FIG. 15B illustrates the instrument with the jaws in a closed position. In the second embodiment described above, the same result is obtained by closing inner handle 470 to impart longitudinal motion to frame clamping tube 518 and clamping tube 337, thereby close anvil 336 against cartridge 337. It is contemplated that achieving proper instrument placement may require multiple attempts to clamp the tissue prior to firing the instrument.

After closing the instrument jaws, the instrument is ready to be fired. To fire the instrument in the first embodiment, the surgeon presses push button 117, whereby the knife 132 and cam bars 131 are driven longitudinally through the cartridge via cam bar channel 129, channel pivot 122, channel pin holder 121, and firing support shaft 117. As explained above, as the cam bars 131 are driven longitudinally through the cartridge, the staple drive members 139 push staples 138 through the body tissue against anvil 136, where the staples 138 are crimped. In the second described embodiment, outer handle 472 is closed to impart longitudinal motion to drive tube 576, channel 329, cams 331 and knife 332 to fire the staples and make an incision.

Referring to FIGS. 33-35, in use, the endoscopic portion of the second alternate embodiment of the invention is inserted into the patient, preferably through an endoscopic tube which can safely and effectively maintain a sealed relationship with the endoscopic portion of the instrument. As in the previously discussed embodiments, the jaws of the instrument are closed for insertion into the endoscopic tube, either by pinching the anvil 796 and cartridge assembly 836 together prior to insertion or by closing the clamping mechanism prior to insertion.

Once inserted into the body cavity, the anvil 796 and cartridge assembly 836 are returned to their first open position (see FIG. 33). By manipulating rotation knob 772 and the instrument, the jaws are oriented to capture the object tissue. Tissue stops 828 in anvil 796 serve to prevent overinsertion of the tissue within the jaws. Once the surgeon is satisfied with the placement of the tissue within the jaws, clamp handle 602 is pivoted downward until it locks in place within frame 600. This pivotal motion forces clamp tube 724, extension tube 726, and collar tube 752 to move longitudinally distal from frame 600. This distal longitudinal movement causes top arcuate camming surface 756 to cam on camming surface 822 forcing anvil 796 to pivot such that: projections 794 move into transverse slot 860; aligning surfaces 830 fit within projections 834; and tissue stops 828 interfit with cartridge assembly 836. Similarly, the pivotal motion of the clamp handle 602 serves to rotate and disengage the link pin assembly 612 from projection 698 on rack rod 684, freeing the rack rod for actuation by the gear handle assembly 622.

When the surgeon is ready to emplace the staples and cut tissue, manual safety 662 is disengaged from firing handle 636 and the firing handle is retracted to proximate the frame 600. This retraction causes arcuate rack 734 to impart counterclockwise rotation on pinion spur gear assembly 672. The counterclockwise motion of the pinion spur gear assembly 672 is translated to distal longitudinal motion by horizontal rack 682. Shaft 700, attached to the proximal end of channel 708 is driven distally causing camming surface 716 of forks 712 to ride up and over projection 892 of the cam bar adapter 845 and drive the cam bar adapter in a distal direction. Shear pin 854 is severed and the cam bars 844 and knife 826 are driven longitudinally through cartridge 838 to sequentially drive and form staples 842 and cut tissue.

At the distal extreme of the longitudinal stroke, the overhanging ledges 874 of cam bars 844 drop over edge 878 of cartridge housing 832 thus abutting vertical surface 876 with edge 878.

After firing, the firing handle 636 is released and returns to its original position with the help of kicker spring 660 and firing handle return spring 659. The return motion of gear handle assembly 622 causes arcuate rack 634 to impart a clockwise rotational motion to the pinion spur gear assembly 672. This clockwise rotational motion is translated to proximal longitudinal motion of shaft 700 by the horizontal rack 682 of rack rod 684. Cam bars 844 are pulled out of cam bar adapter 846 and remain in position in the longitudinal slots 850 of the cartridge 838. The cam bar adapter, with knife 826 attached, moves proximally within cartridge housing 832 until the outer edges of cam bar adapter 846 impinge on crimps 862. At that point, forks 712 of channel 708 are clear of biasing spring 800 in support 778.

The cam bar adapter 846 is held in place by crimps 862 while camming surface 718 of fork 712 causes the fork to ride up and disengage with projection 892 of the cam bar adapter. Channel 708 continues to move in the proximal direction until abutting structure 720 is positioned proximally to rearward projection 850 formed in the floor of cartridge housing 832. At this point, the entire cartridge assembly 836 is deactivated.

In the event that the surgeon should accidentally attempt to again retract the firing handle 636 without replacing the deactivated cartridge with a new unfired cartridge, the resulting distal longitudinal motion of the channel 708 moves abutting structure 720 into contact with rearward projection 850 effectively preventing further movement of forks 712 toward cam bar adapter 846.

After firing, clamp handle 602 is raised with the assistance of clamp spring 618 which action retracts clamp tube 724, extension tube 726 and collar tube 752. This retraction causes leaf spring 814 to move anvil 796 out of engagement of transverse slot 860 and pivot anvil 796 upward. Similarly, raising of clamp handle 602 causes link pin assembly 612 to reengage projection 698 on rack rod 684. In this engaged position, the rack rod 684 is prevented from moving in the distal longitudinal direction in response to an attempted retraction of the gear handle assembly 622.

In order to replace the cartridge assembly, the instrument is withdrawn from the patient. Release button 812 is depressed, biasing engaging structure 806 out of transverse locking slot 848. The cartridge assembly is released and may be removed by pulling it distally out of collar tube 752.

To reinsert a new cartridge assembly, the proximal end of the cartridge assembly is inserted into collar tube 752 until engaging structure 806 locks into transverse locking slot 848. The instrument is now ready for reinsertion and continued use.

Operation of the instrument with the ligating and dividing cartridge and anvil assembly shown in FIGS. 65-69 is substantially similar to that described above. Tubular tissue to be ligated and/or divided is captured within the anvil 900 and the cartridge assembly 910 such that the tissue is transversely oriented distal to tissue stops 908 and proximal from arcuate tissue capturing portion 920 of anvil 900. The cartridge assembly 910 and anvil 900 are approximated, effectively interlocking surfaces 920, 936, 938 and 922. The staples 840 are fired, ligating the tissue and, where desired, knife 826 divides the ligated tissue. Opening, removal and replacement of the deactivated cartridge are effected in substantially the same way as described above with respect to the second alternative embodiment.

Referring to FIGS. 70-73, it is contemplated that the anvil/cartridge assembly of the present invention could be replaced with other interacting jaw members such as, for example, a pair of gripping jaw members, 940 and 942 respectively, for holding and dissecting tissue as well as clamping jaw members, 944 and 946 respectively, for clamping off tissue or portions thereof. These interacting jaw members may include serrated portions 948 to improve gripping/holding ability. Alternatively, the interacting jaw members may be provided with tissue contacting surfaces 950 and 952 respectively, which prevent or minimize trauma to held or clamped tissue.

These interacting jaw members would be mounted in substantially the same way as the anvil/cartridge assembly described herein with the exception that staples and/or knives need not be driven to join and/or divide tissue.

It will be understood that various modifications can be made to the various embodiments of the present invention herein disclosed without departing from the spirit and scope thereof. For example, various sizes of the instrument are contemplated, as well as various types of construction materials. Also, various modifications may be made in the configuration of the parts. For example, in the first embodiment the elongated slot for allowing access to the thumbwheel may be placed alternatively in the left body portion or right body portion. Therefore the above description should not be construed as limiting the invention but merely as exemplifications of preferred embodiments thereof. Those skilled in the art will envision other modifications within the scope and spirit of the present invention as defined by the claims appended hereto.

What is claimed is:

1. A surgical apparatus for laparoscopic or endoscopic procedures comprising:
   a frame;
   an endoscopic portion defining a longitudinal axis and extending distally from the frame; a tool assembly supported on the distal end of the endoscopic portion, the tool assembly including a first jaw pivotably supported in relation to a second jaw, wherein the first jaw is movable in relation to the second jaw between open and closed positions;
   a first mechanism extending between the tool assembly and the frame, the first mechanism including a clamp tube positioned at least partially within the frame, the clamp tube being movable from a retracted position to an advanced position to move the first jaw in relation to the second jaw from the open position to the closed position;
   a second mechanism extending between the frame and the tool assembly, the second mechanism including an extension tube, the extension tube being movable from a retracted position to an advanced position to actuate the tool assembly; and
   a bellows seal having a distal end and a proximal end and a central bellows portion, the bellows seal defining a throughbore, the distal end of the bellows seal being positioned to sealingly engage an outer surface of the extension tube and the proximal end of the bellows seal being positioned to sealingly engage the clamp tube, wherein as the clamp tube is moved from the retracted position to the advanced position, the bellows seal is compressed and expanded outwardly to seal against an internal surface of the frame.

2. A surgical apparatus according to claim 1, wherein the frame includes an internal flange which is positioned to engage the bellows seal as the clamp tube is moved from its retracted position to its advanced position.

3. A surgical apparatus according to claim 1, wherein the bellows seal is in a slight interference condition with the internal surface of the frame to provide a seal with the frame when the clamp tube is in its retracted position, and wherein movement of the clamp tube towards its advanced position increases the capacity of the seal.

4. A surgical apparatus according to claim 1, wherein the first jaw includes an anvil member and the second jaw includes a cartridge assembly.

5. A surgical apparatus according to claim 4, wherein the cartridge assembly includes a plurality of staples.

6. A surgical apparatus according to claim 1, wherein the frame supports a clamp handle which is operably associated with the first mechanism.

7. A surgical apparatus according to claim 6, wherein the frame supports a handle assembly which is operably associated with the second mechanism.

8. A surgical apparatus according to claim 1, wherein the clamp tube is configured to engage an external surface of the anvil member to move the anvil member and the cartridge assembly from the open position to the closed position.

9. A surgical apparatus according to claim 1, wherein the endoscopic portion is rotatably supported on the frame.

10. A surgical apparatus for laparoscopic or endoscopic procedures comprising:
    a frame;
    an endoscopic portion defining a longitudinal axis and extending distally from the frame; a tool assembly supported on the distal end of the endoscopic portion, the tool assembly including a first jaw pivotably supported in relation to a second jaw, wherein the first jaw is movable in relation to the second jaw between open and closed positions;
    a first mechanism extending between the tool assembly and the frame, the first mechanism including a clamp tube positioned at least partially within the frame, the clamp tube being movable from a retracted position to an advanced position to move the first jaw in relation to the second jaw from the open position to the closed position;
    a second mechanism extending between the frame and the tool assembly, the second mechanism including an extension tube, the extension tube being movable from a retracted position to an advanced position to actuate the tool assembly; and
    a bellows seal having a distal end and a proximal end and a central bellows portion, the bellows seal defining a throughbore, the distal end of the bellows seal being positioned to sealingly engage an outer surface of the extension tube and the proximal end of the bellows seal being positioned to sealingly engage the clamp tube, wherein as the clamp tube is moved from the retracted position to the advanced position, the bellows seal is compressed and expanded outwardly to seal against an internal surface of the frame,
    wherein the bellows seal does not engage the internal surface of the frame until the clamp tube is moved towards its advanced position.

11. A surgical apparatus according to claim 10, wherein the frame includes an internal flange which is positioned to engage the bellows seal as the clamp tube is moved from its retracted position to its advanced position.

12. A surgical apparatus according to claim 1, wherein the bellows seal is in a slight interference condition with the internal surface of the frame to provide a seal with the frame when the clamp tube is in its retracted position, and wherein movement of the clamp tube towards its advanced position increases the capacity of the seal.

13. A surgical apparatus for laparoscopic or endoscopic procedures comprising:
   a frame;
   an endoscopic portion defining a longitudinal axis and extending distally from the frame;
   a tool assembly supported on the distal end of the endoscopic portion, the tool assembly including a first jaw pivotably supported in relation to a second jaw, wherein the first jaw is movable in relation to the second jaw between open and closed positions;
   a first mechanism extending between the tool assembly and the frame, the first mechanism including a clamp tube positioned at least partially within the frame, the clamp tube being movable from a retracted position to an advanced position to move the first jaw in relation to the second jaw from the open position to the closed position;
   a second mechanism extending between the frame and the tool assembly, the second mechanism including an extension tube, the extension tube being movable from a retracted position to an advanced position to actuate the tool assembly; and
   a bellows seal having a distal end and a proximal end and a central bellows portion, the bellows seal defining a throughbore, the distal end of the bellows seal being positioned to sealingly engage an outer surface of the extension tube and the proximal end of the bellows seal being positioned to sealingly engage the clamp tube, wherein as the clamp tube is moved from the retracted position to the advanced position, the bellows seal is positioned and configured to be compressed longitudinally and expanded outwardly to seal against an internal surface of the frame.

14. A surgical apparatus according to claim 13, wherein the frame includes an internal flange which is positioned to engage the bellows seal as the clamp tube is moved from its retracted position to its advanced position.

15. A surgical apparatus according to claim 13, wherein the bellows seal does not engage the internal surface of the frame until the clamp tube is moved towards its advanced position.

16. A surgical apparatus according to claim 13, wherein the bellows seal is in a light interference condition with the internal surface of the frame to provide a seal with the frame when the clamp tube is in its retracted position, and wherein movement of the clamp tube towards its advanced position increases the capacity of the seal.

17. A surgical apparatus according to claim 1, wherein the first jaw includes an anvil member and the second jaw includes a cartridge assembly.

18. A surgical apparatus according to claim 4, wherein the cartridge assembly includes a plurality of staples.

19. A surgical apparatus according to claim 1, wherein the frame supports a clamp handle which is operably associated with the first mechanism.

20. A surgical apparatus according to claim 6, wherein the frame supports a handle assembly which is operably associated with the second mechanism.

21. A surgical apparatus according to claim 1, wherein the clamp tube is configured to engage an external surface of the anvil member to move the anvil member and the cartridge assembly from the open position to the closed position.

22. A surgical apparatus according to claim 1, wherein the endoscopic portion is rotatably supported on the frame.

* * * * *